(12) United States Patent
Bryant-Greenwood et al.

(10) Patent No.: US 12,303,233 B2
(45) Date of Patent: *May 20, 2025

(54) DEVICES, SYSTEMS, AND METHODS FOR VIRTUAL STAINING

(71) Applicant: Genetic Innovations, Inc., Honolulu, HI (US)

(72) Inventors: Peter Bryant-Greenwood, Honolulu, HI (US); Kevin P. Rosenblatt, Houston, TX (US); Jeffrey N. Yu, Honolulu, HI (US)

(73) Assignee: Genetic Innovations, Inc., Honolulu, HI (US)

(*) Notice: Subject to any disclaimer, the term of this patent is extended or adjusted under 35 U.S.C. 154(b) by 44 days.

This patent is subject to a terminal disclaimer.

(21) Appl. No.: 18/331,108

(22) Filed: Jun. 7, 2023

(65) Prior Publication Data
US 2023/0404406 A1 Dec. 21, 2023

Related U.S. Application Data

(63) Continuation of application No. 16/911,098, filed on Jun. 24, 2020, now Pat. No. 11,684,264, which is a
(Continued)

(51) Int. Cl.
*A61B 5/00* (2006.01)
*G06T 5/00* (2024.01)
(Continued)

(52) U.S. Cl.
CPC .............. *A61B 5/0059* (2013.01); *G06T 5/90* (2024.01); *G06T 7/0012* (2013.01); *G06T 7/90* (2017.01);
(Continued)

(58) Field of Classification Search
CPC ... A61B 2576/00; A61B 5/0059; A61B 5/055; G01R 33/5608; G06T 2207/10024;
(Continued)

(56) References Cited

U.S. PATENT DOCUMENTS 5,991,028 A 11/1999 Cabib et al.
6,160,618 A 12/2000 Garner
(Continued)

FOREIGN PATENT DOCUMENTS

WO WO 2006/091221 8/2006
WO WO 2010/061319 6/2010
(Continued)

OTHER PUBLICATIONS

Ferris, Daron G. et al., "Multimodal Hyperspectral Imaging for the Noninvasive Diagnosis of Cervical Neoplasia," J. of Lower Gential Tract Disease, vol. 5, No. 2, 2001, pp. 65-72.
(Continued)

*Primary Examiner* — Michael T Rozanski
(74) *Attorney, Agent, or Firm* — Perkins Coie LLP

(57) ABSTRACT

The disclosure herein provides methods, systems, and devices for virtually staining biological tissue for enhanced visualization without use of an actual dye or tag by detecting how each pixel of an unstained tissue image changes in waveform after staining with a certain dye(s) and/or tag(s) or other transformation under a certain electromagnetic radiation source, developing a virtual staining transform based on such detection, and applying such virtual staining transform to an unstained biological tissue to virtually stain the tissue.

20 Claims, 41 Drawing Sheets

Related U.S. Application Data continuation of application No. 14/224,903, filed on Mar. 25, 2014, now Pat. No. 10,729,325, which is a continuation of application No. 13/843,588, filed on Mar. 15, 2013, now Pat. No. 8,725,237.

(60) Provisional application No. 61/656,930, filed on Jun. 7, 2012, provisional application No. 61/612,925, filed on Mar. 19, 2012.

(51) Int. Cl.
| | |
|---|---|
| G06T 5/90 | (2024.01) |
| G06T 7/00 | (2017.01) |
| G06T 7/90 | (2017.01) |
| A61B 5/055 | (2006.01) |
| G01R 33/56 | (2006.01) |

(52) U.S. Cl.
CPC ........... A61B 5/055 (2013.01); A61B 2576/00 (2013.01); G01R 33/5608 (2013.01); G06T 2207/10024 (2013.01); G06T 2207/10056 (2013.01); G06T 2207/30024 (2013.01)

(58) Field of Classification Search
CPC . G06T 2207/10056; G06T 2207/30024; G06T 5/90; G06T 7/0012; G06T 7/90; G16H 30/40; Y02A 90/10
See application file for complete search history.

(56) References Cited

U.S. PATENT DOCUMENTS

| | | | |
|---|---|---|---|
| 6,198,532 B1 | 3/2001 | Cabib et al. | |
| 6,337,472 B1 | 1/2002 | Garner et al. | |
| 7,945,077 B2 | 5/2011 | Demos | |
| 8,320,996 B2 | 11/2012 | Panasyuk et al. | |
| 8,705,833 B2 | 4/2014 | Yag et al. | |
| 8,725,237 B2 | 5/2014 | Bryant-Greenwood | |
| 8,977,017 B2 | 3/2015 | Otsuka et al. | |
| 10,729,325 B2 * | 8/2020 | Bryant-Greenwood | G06T 7/0012 |
| 11,684,264 B2 * | 6/2023 | Bryant-Greenwood | G06T 7/90 600/407 |
| 2001/0017938 A1 | 8/2001 | Kerschmann et al. | |
| 2003/0118222 A1 | 6/2003 | Foran et al. | |
| 2004/0085443 A1 | 5/2004 | Kallioniemi et al. | |
| 2008/0082458 A1 | 4/2008 | Airoldi et al. | |
| 2008/0102487 A1 | 5/2008 | Yao et al. | |
| 2008/0273788 A1 | 11/2008 | Soenksen et al. | |
| 2009/0245610 A1 | 10/2009 | Can et al. | |
| 2010/0056928 A1 | 3/2010 | Zuzak et al. | |
| 2010/0128988 A1 | 5/2010 | Kincaid | |
| 2010/0195903 A1 | 8/2010 | Tani | |
| 2011/0074944 A1 | 3/2011 | Can et al. | |
| 2011/0109735 A1 | 5/2011 | Otsuka | |
| 2012/0147002 A1 | 6/2012 | Young et al. | |
| 2012/0269417 A1 | 6/2012 | Young et al. | |
| 2013/0071002 A1 | 3/2013 | Otsuka | |
| 2013/0317369 A1 | 11/2013 | Bryant-Greenwood | |
| 2014/0021813 A1 | 8/2014 | Bryant-Greenwood et al. | |
| 2014/0252200 A1 | 9/2014 | Garsha et al. | |

FOREIGN PATENT DOCUMENTS

| | | |
|---|---|---|
| WO | WO 2011/163624 | 12/2011 |
| WO | WO 2013/142366 | 9/2013 |
| WO | WO 2019/046774 | 3/2019 |

OTHER PUBLICATIONS

Folkman, Mark et al., "EO-1/Hyperion Hyperspectral Imager Design, Development, Characterization, and Calibration," SPIE, vol. 4151, 2000, 12 pages.
Geho, David et al., "Pegylated, Steptavidin-Conjugated Quantum Dots are EffectiveDetection Elements for Reverse-Phase Protein Microarrays," Bioconjugate Chem. Vol. 16, No. 3, 2005, pp. 559-566.
Huebschman, Michael L. et al., "Hyperspectral Microscopy Imaging to AnalyzePathology Samples with Multi-colors Reduces Time and Cost," Proc. SPIE vol. 7182, 71821F, 2009, 10 pages.
Bautista, et al., "Digital simulation of staining in histopathology multispectral images:enhancement and linear transformation of spectral transmittance," Journal of Biomedical Optics, 17(5), 056013 (May 2012).
Bautista, et al., "Digital Staining of Unstained Pathological Tissue Samples through Spectral Transmittance Classification," Optical Review, vol. 12, No. 1 (2005) pp. 1-8.
Bautista, et al., "Digital Staining for Histopathology Multispectral Images by the Combined Application of Spectral Enhancement and Spectral Transformation," 33rd Annual International Conference of the IEEE EMBS, Aug. 30,-Sep. 3, 2011, in 4 pages.
Extended European Search Report in EP 13764197.3 dated Dec. 19, 2014 in 11 pages.
International Search Report and Written Opinion of the International Search Authority in PCT/US2013/032389, dated Jul. 8, 2013, 13 pages.
Memarsadeghi, Nargess et al., "NASA Computational Case Study, Hyperspectral DataProcessing: Cryospheric Change Detection," Computing in Science and Engineering, vol. 14, No. 4, 2012, pp. 92-97, 11 pages.
Shippert, Peg, "Introduction to Hyperspectral Image Analysis," Online J. of Space Commun, Issue 3, 2003, 13 pages.
International Search Report and Written Opinion of the International Search Authority in PCT/US2018/049185, dated Nov. 2, 2018, 4 pages.
Bautista, Pinky et al., "Digital simulation of staining in histopathology multispectral images:enhancement and linear transformation of spectral transmittance,"vol. 17, No. 5, 2012, pp. 1-11.
Bai et al., "Label-free virtual HER2 immunohistochemical staining of breast tissue using deep learning," pp. 1-26.

* cited by examiner

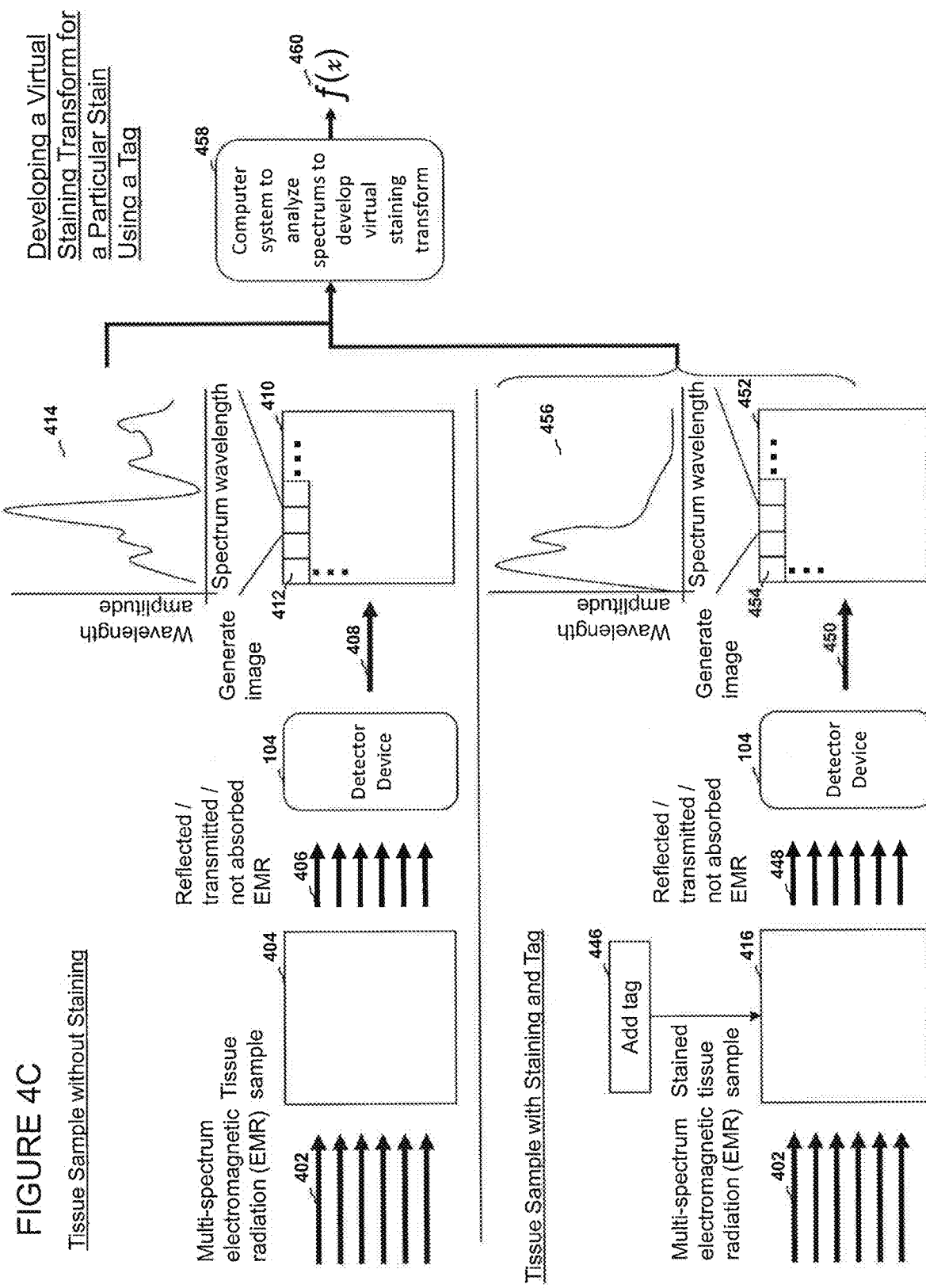

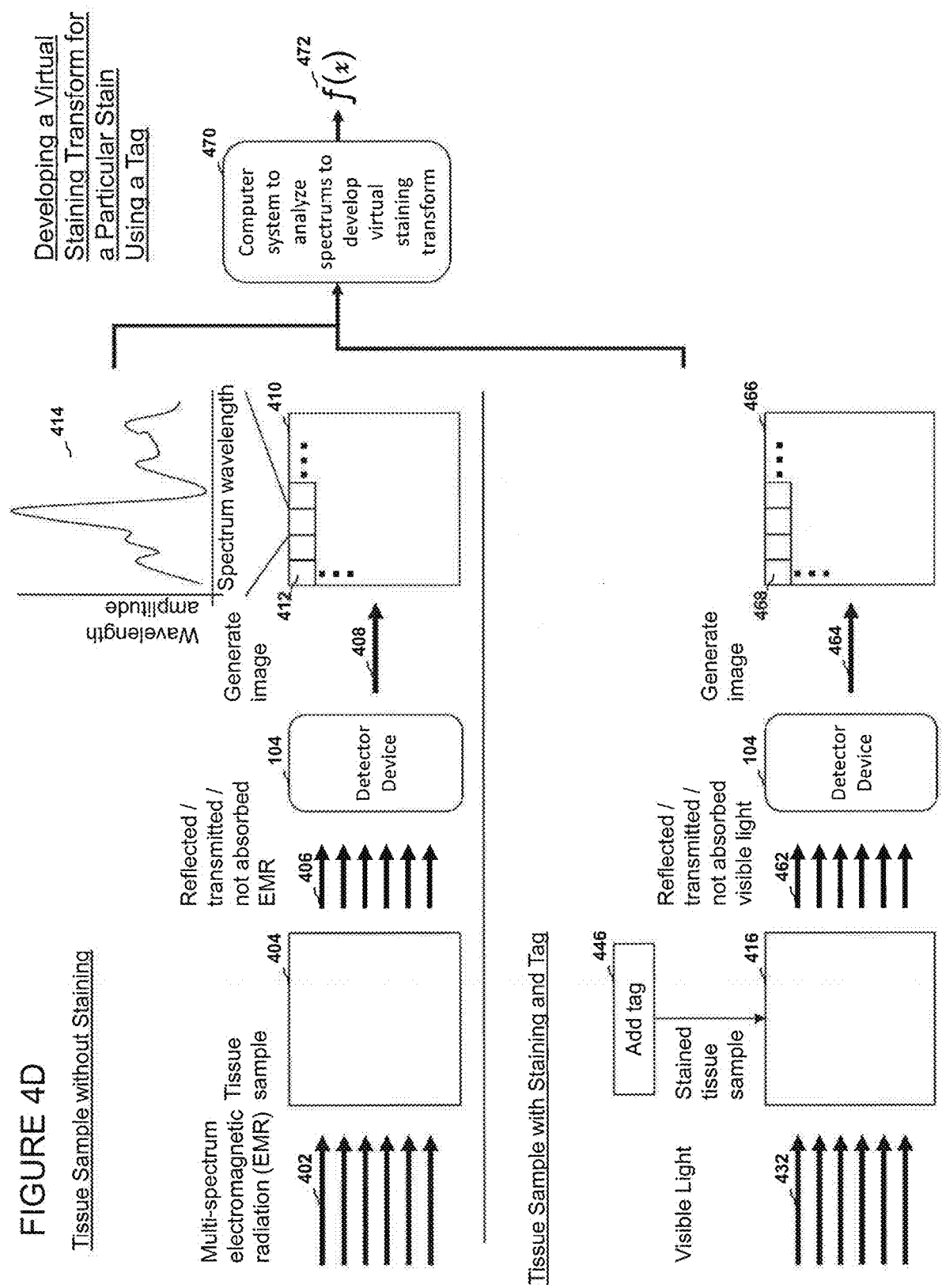

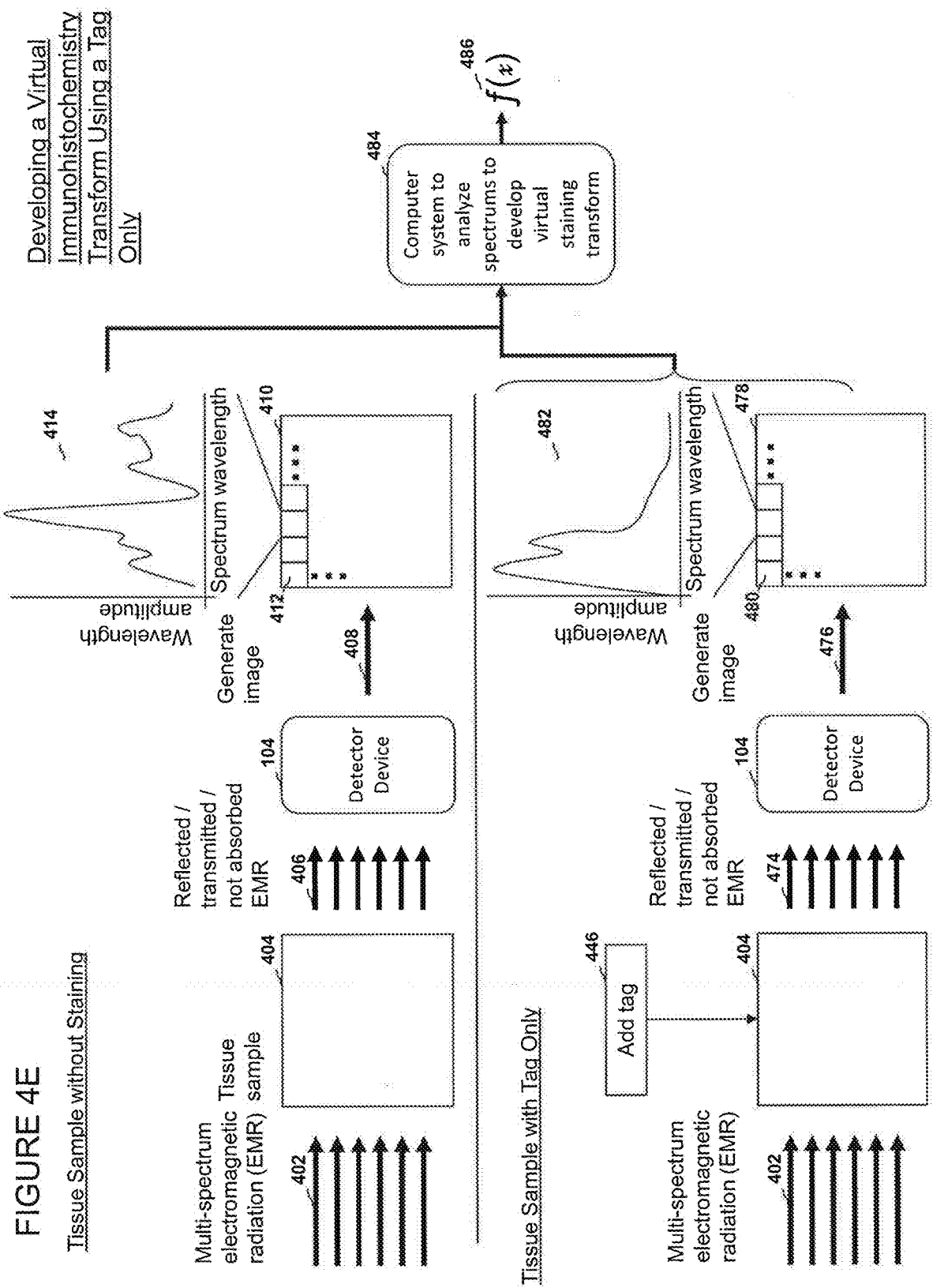

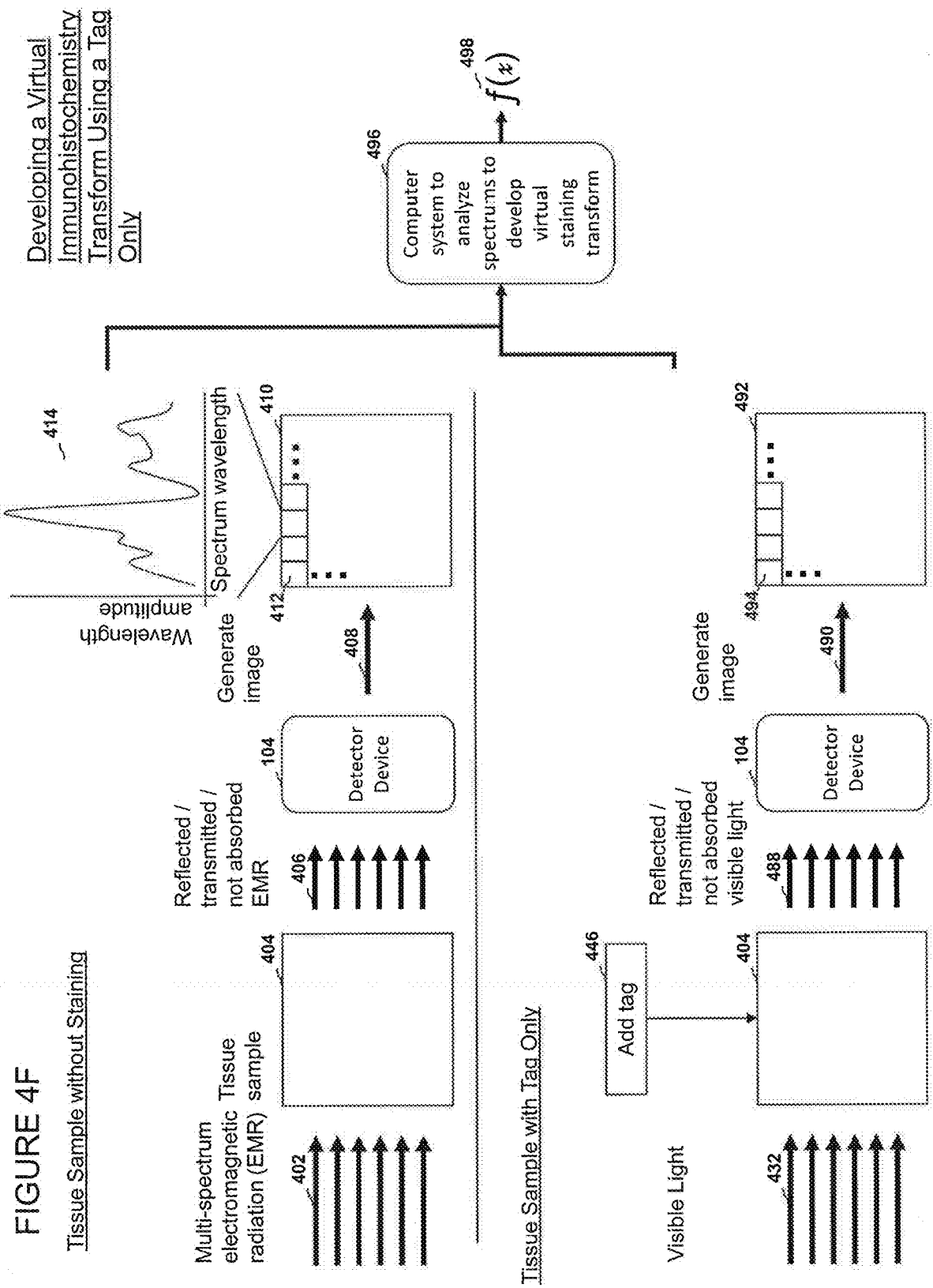

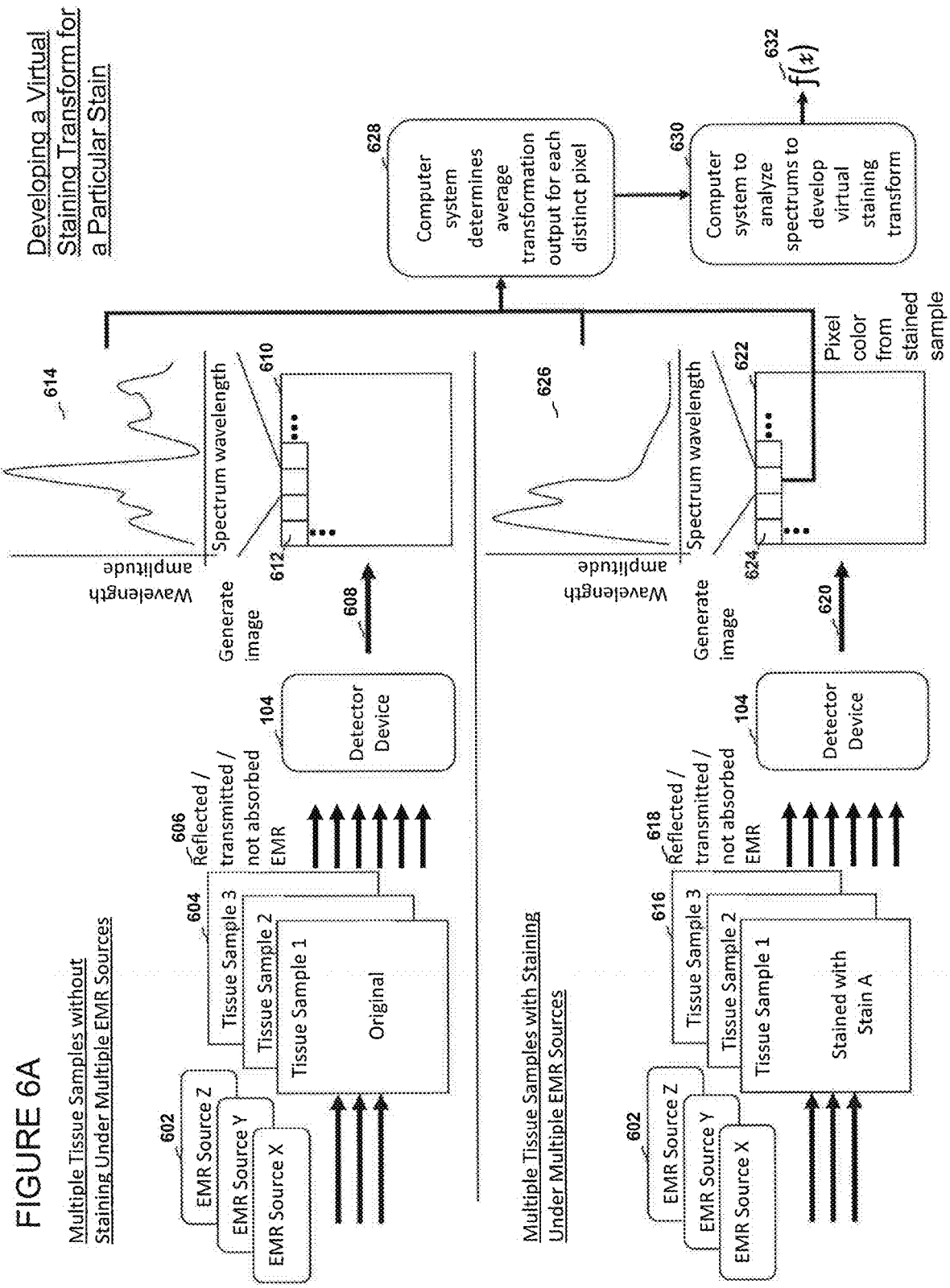

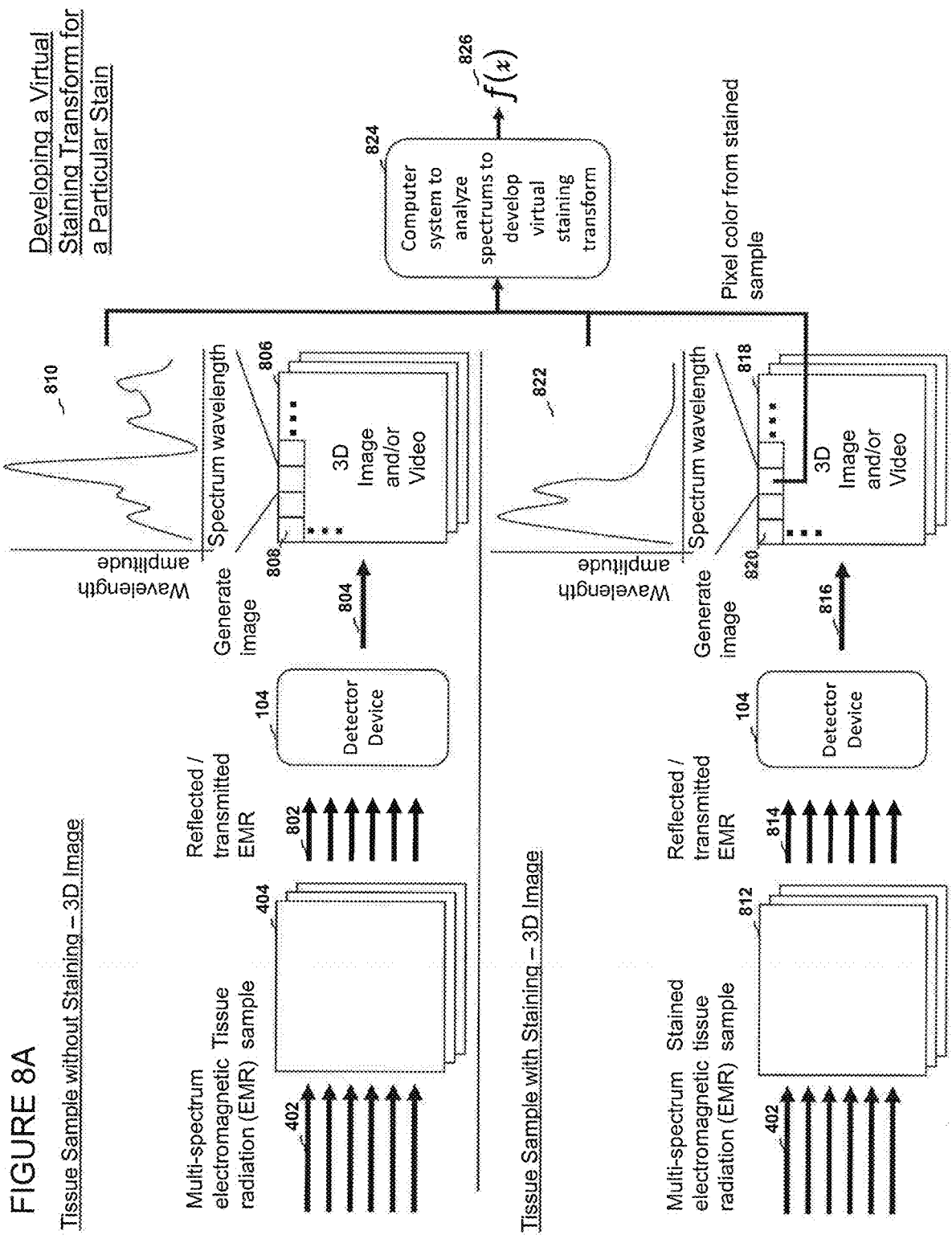

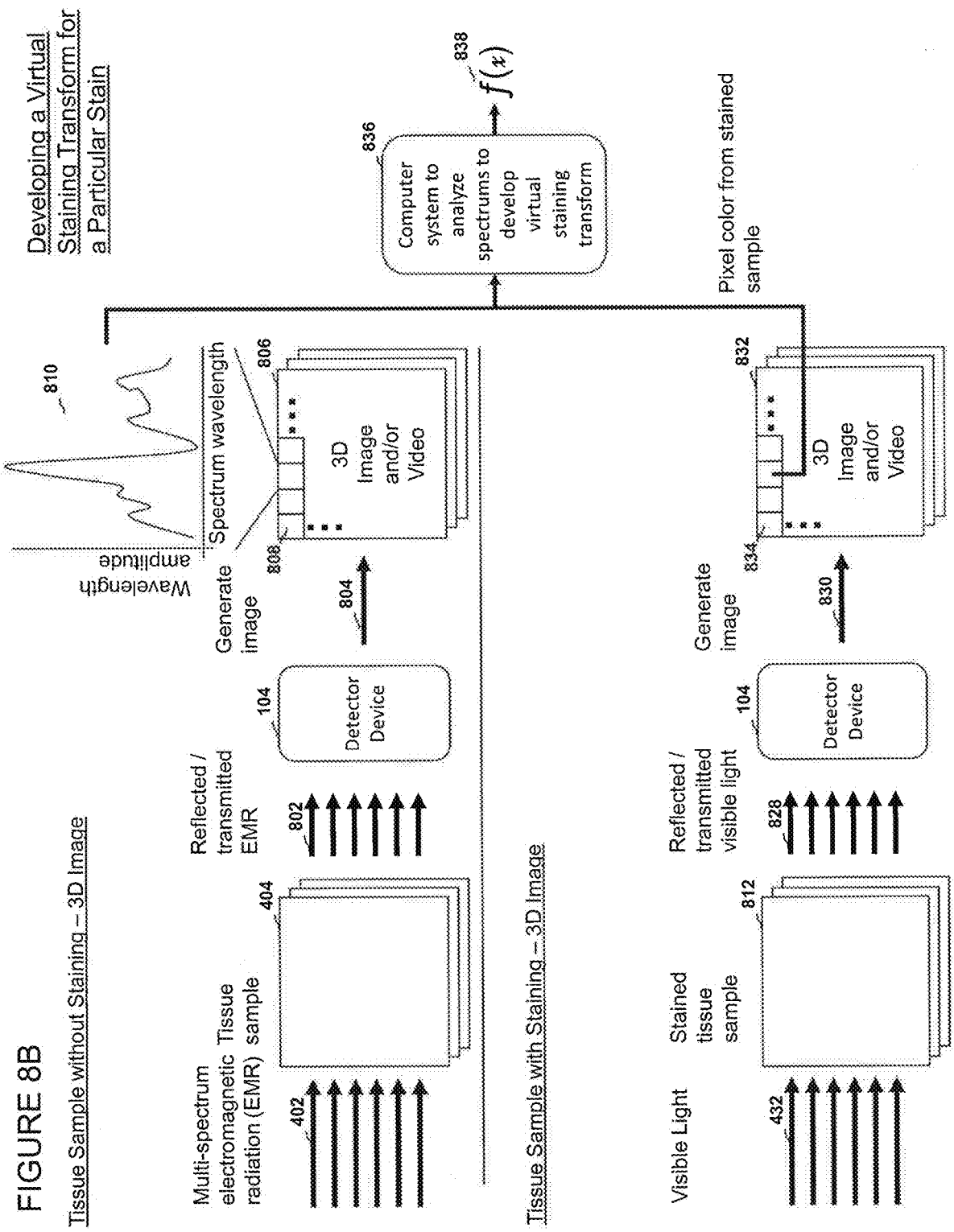

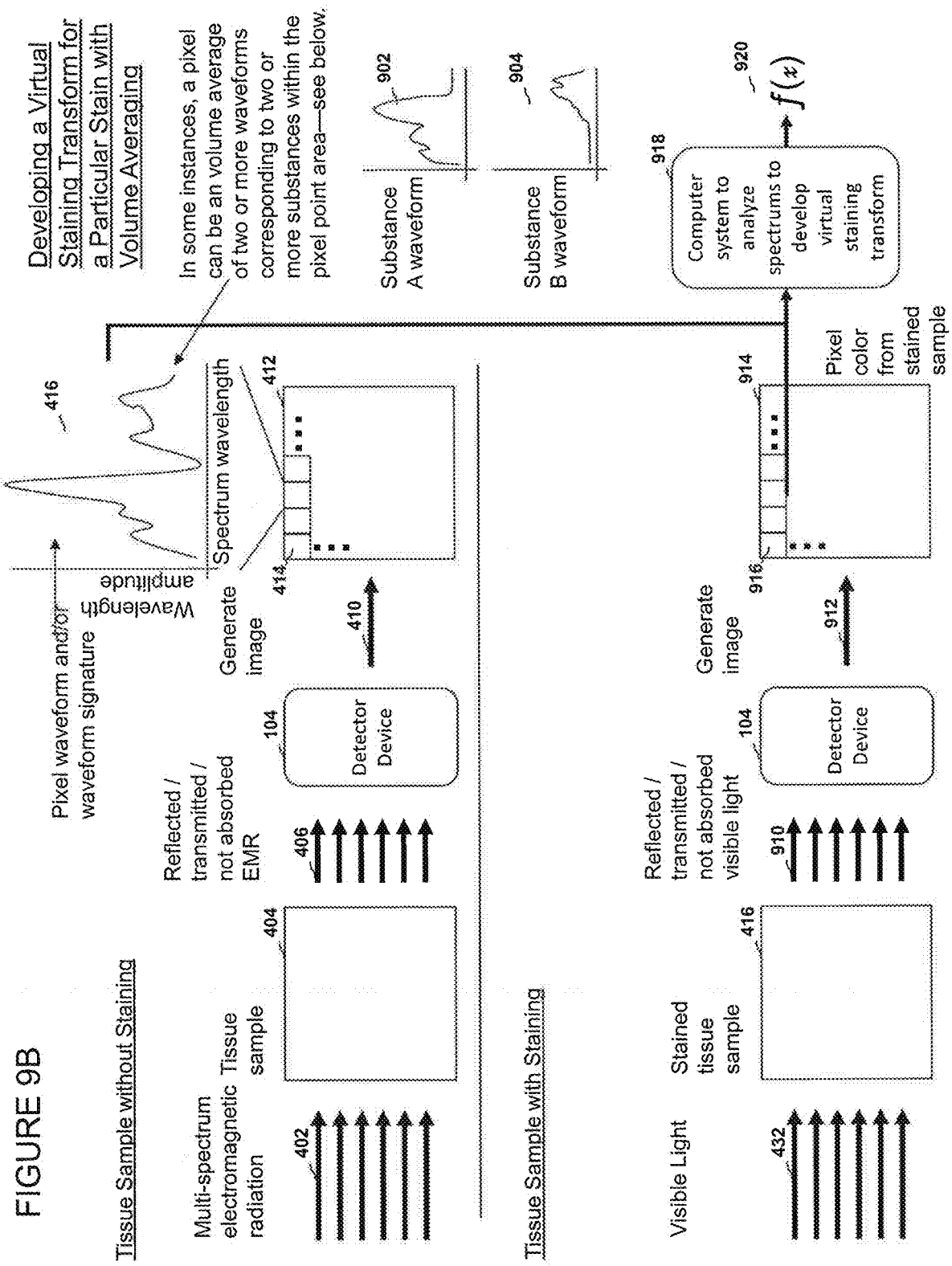

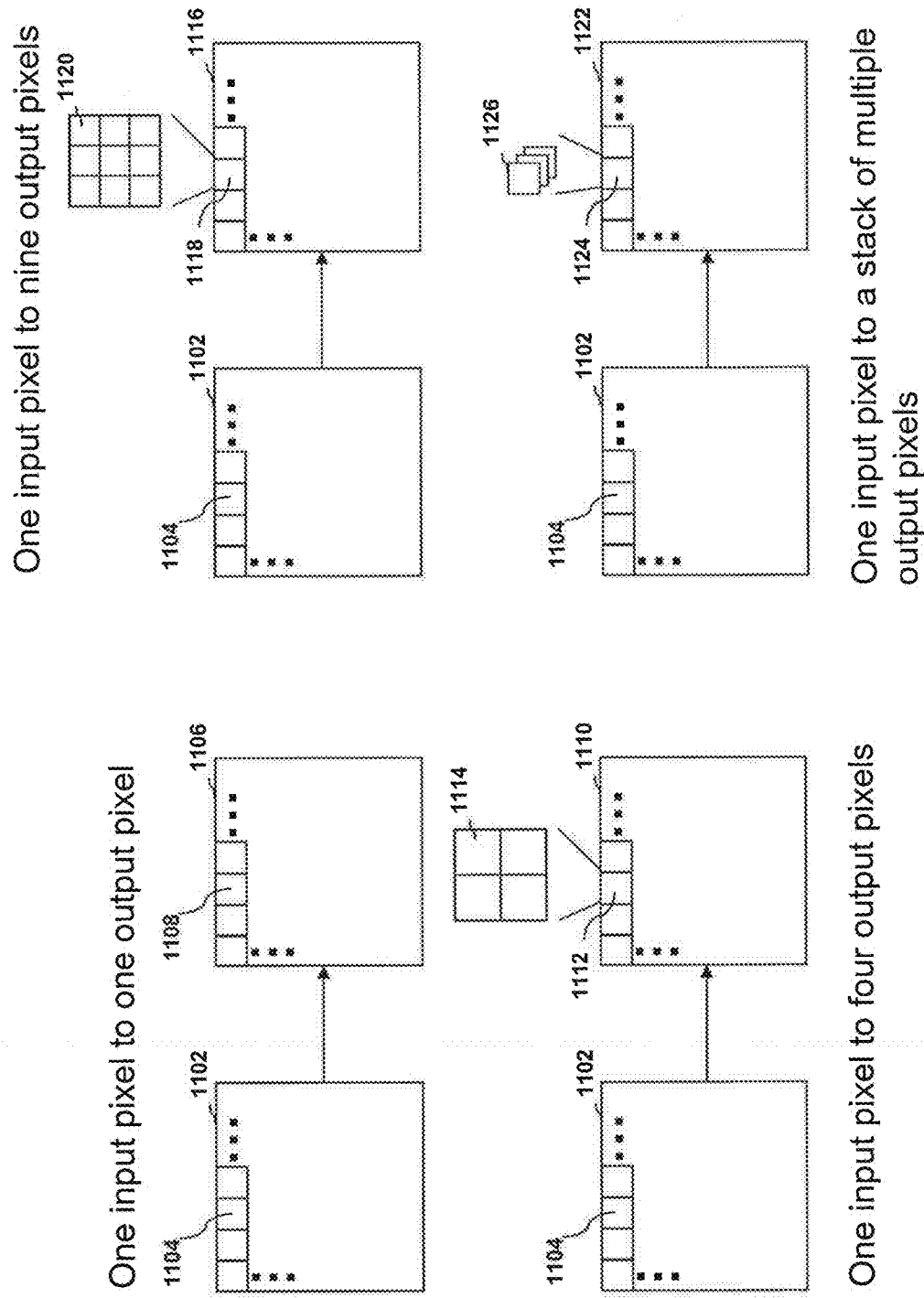

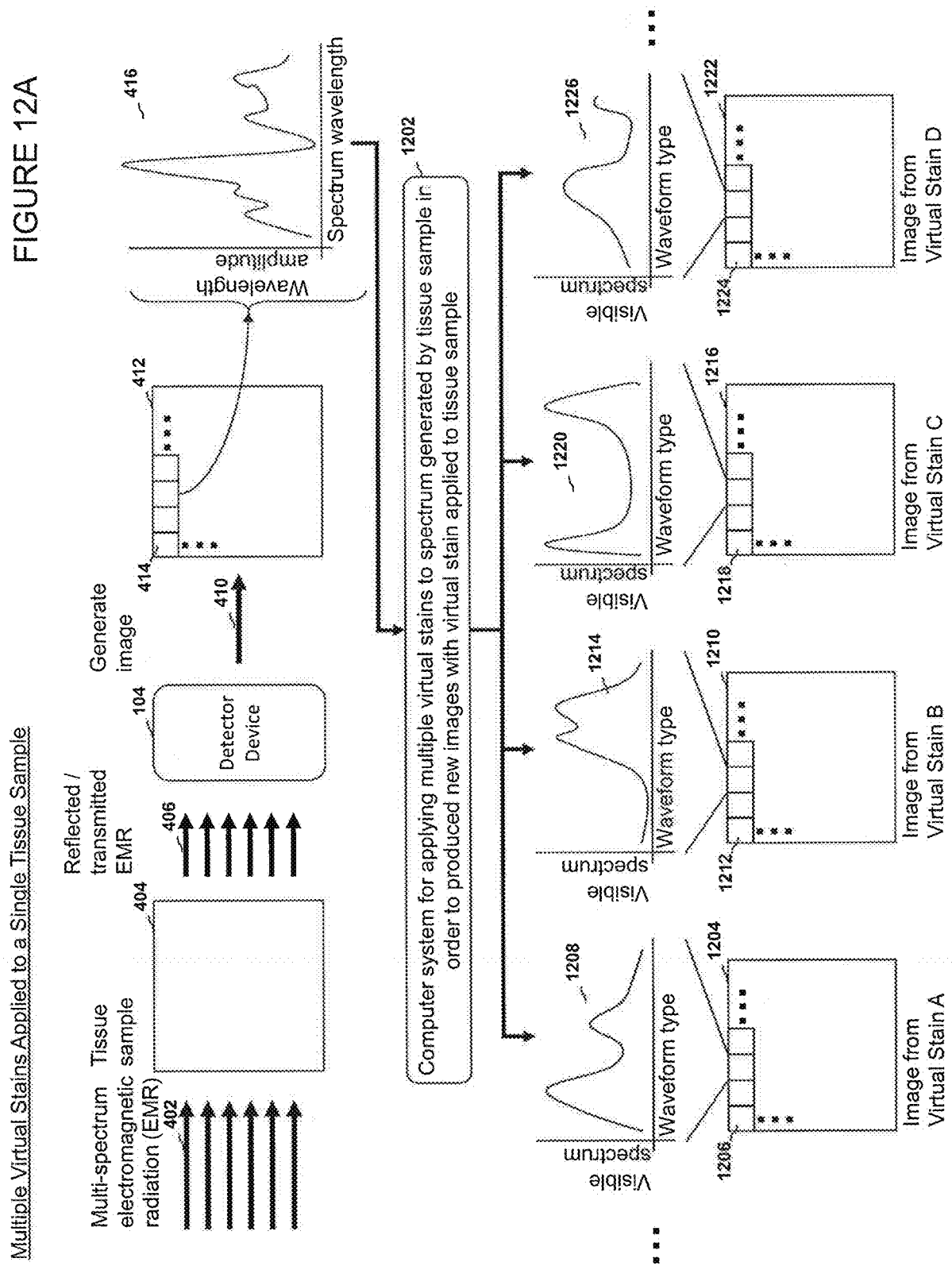

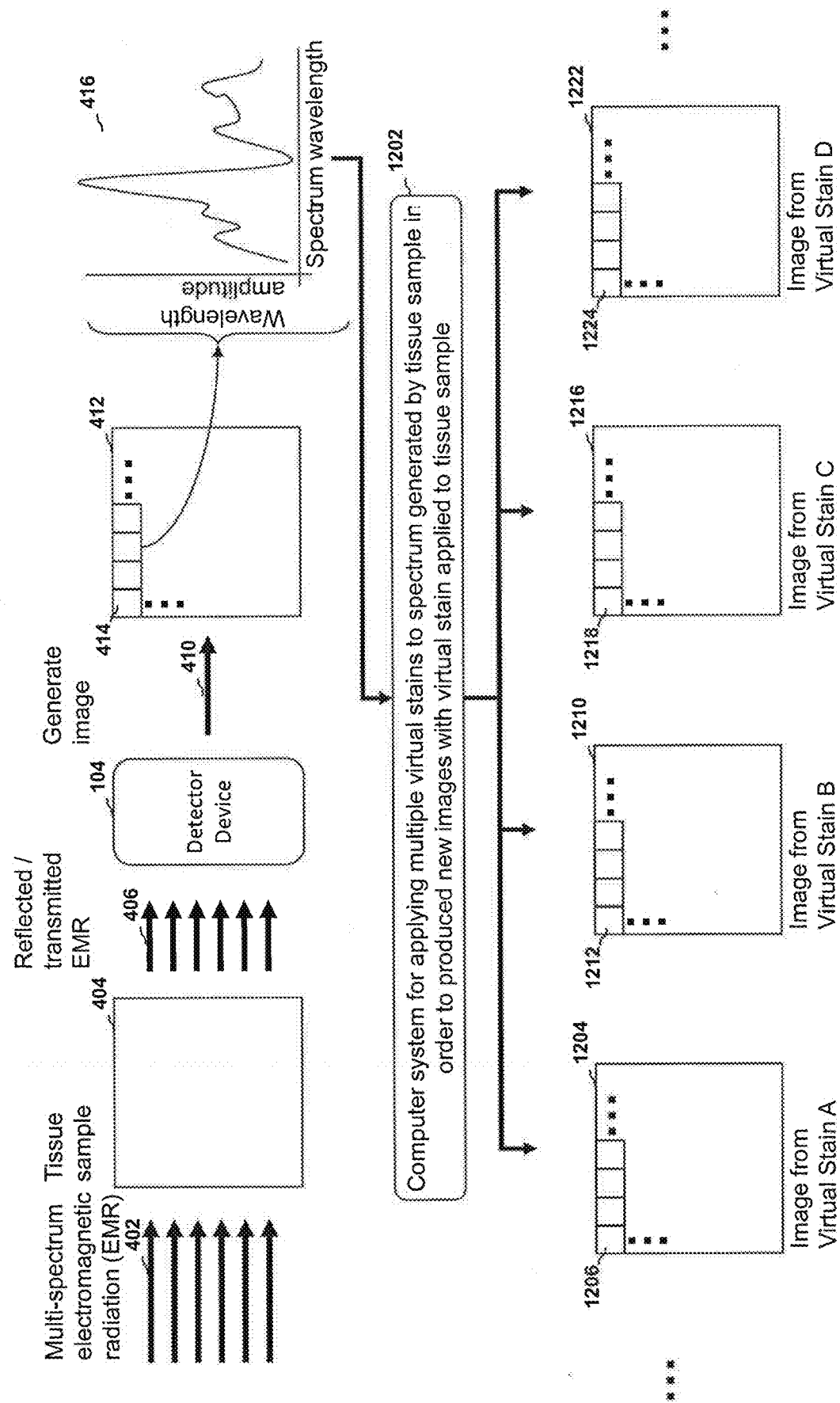

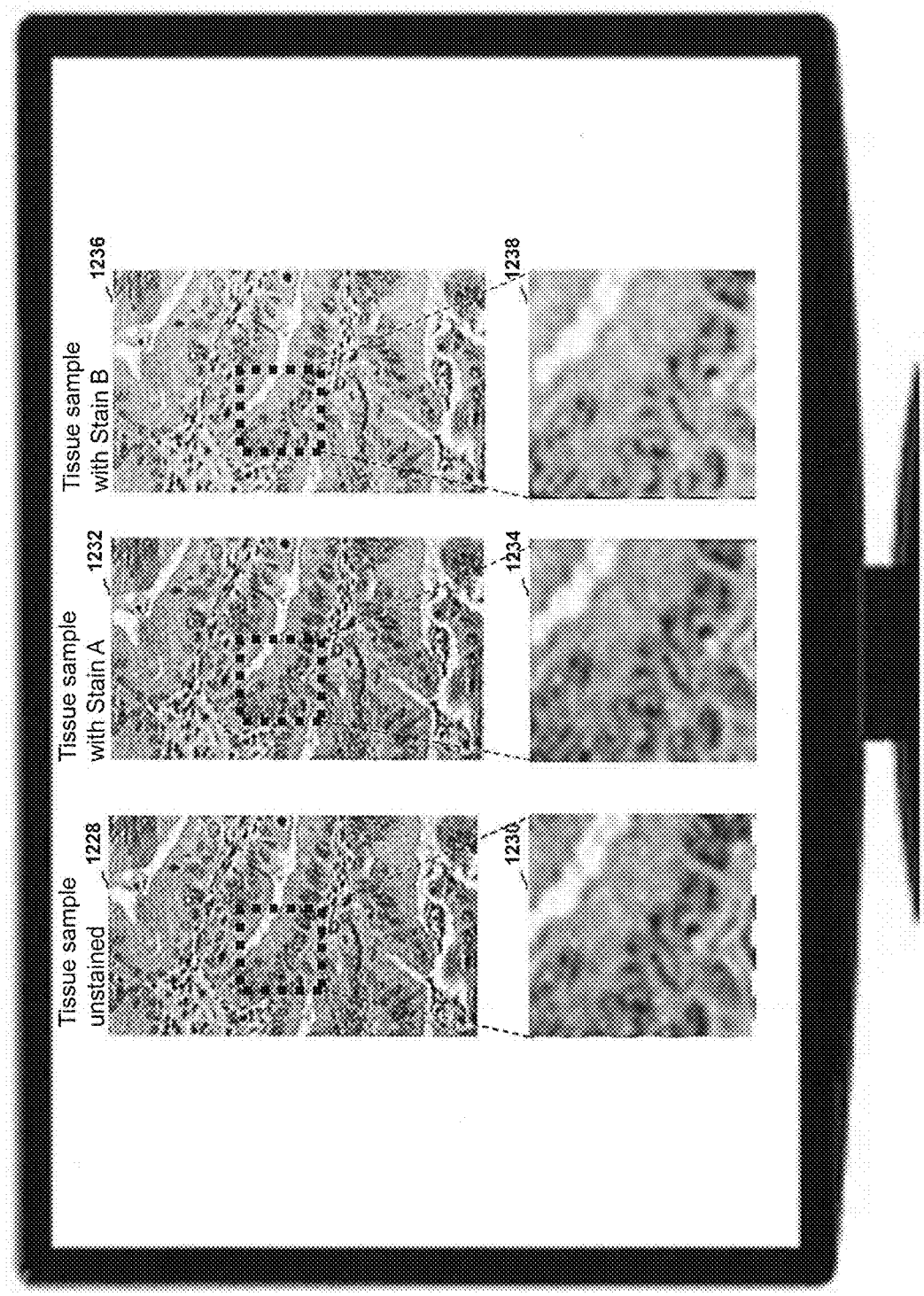

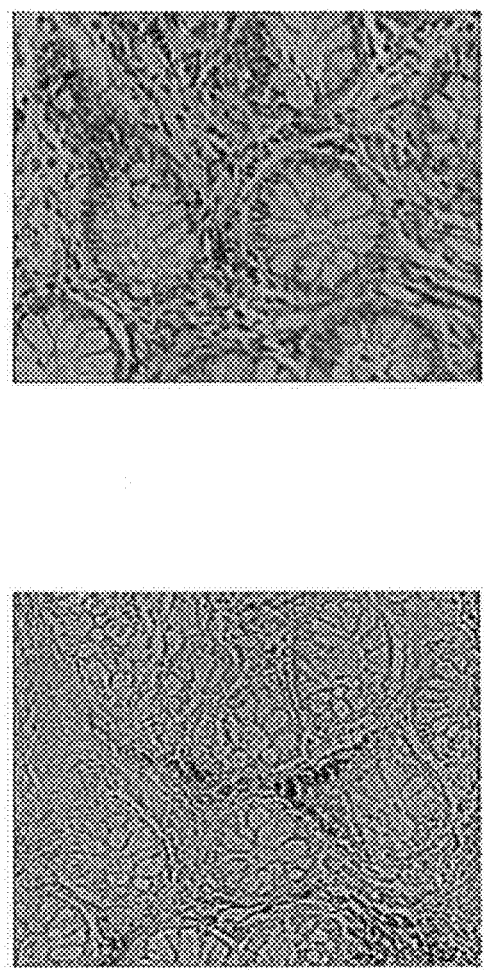
Fig. 13A: Digitally stained result
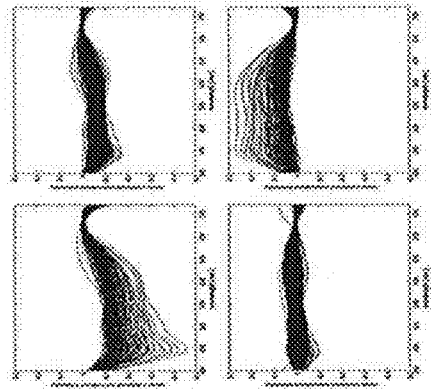
Fig. 13B: H&E stained slide
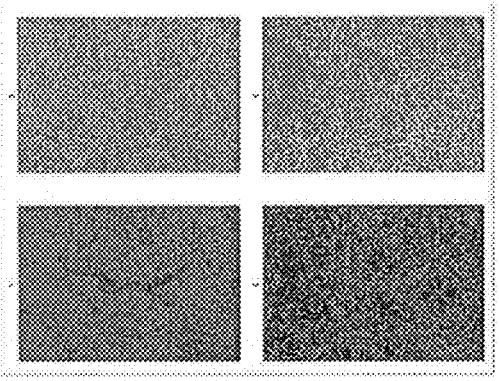
Fig. 13D: Ensembles of spectra associated with the 4 classes of Fig. 13C
Fig. 13C: Unsupervised classification of normalized denoised hyperspectral cube into 4 classes 40X Colon Tissue Using Emission Spectra Hyperspectral Composite of Unstained Slide - Pseudo Color Bacillus atrophaeus spores
Spectral Analysis Black+Rainbow + White
Black = least match
White = best match False Color Match to Spectra Composite Image

FIGURE 15A

Escherichia Coli
Spectral Analysis
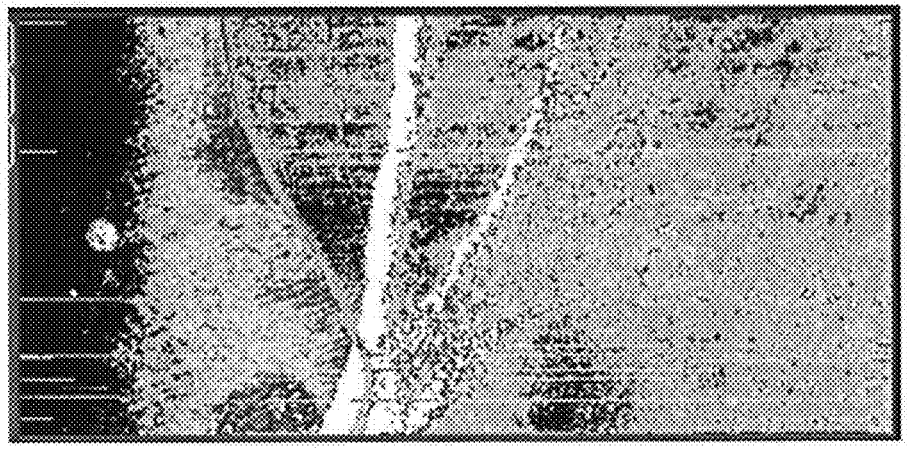
False Color Match to Spectra
Balck+Rainbow + White
Black = least match
White=best match
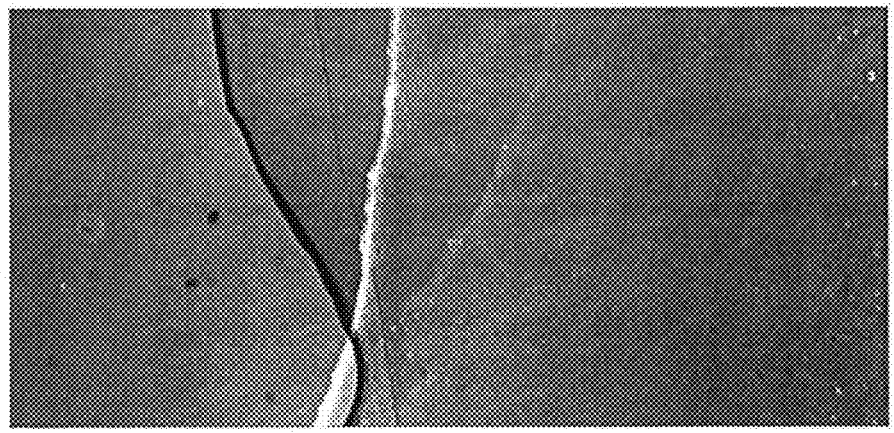
Composite Image
FIGURE 15B Using Detected Pixel Waveforms to Diagnosis or Correlate to Particular Diseases Using Detected Pixel Waveforms to Diagnosis or Correlate to Particular Diseases Using Detected Pixel Waveforms to Diagnosis or Correlate to Particular Diseases Using Detected Pixel Waveforms to Diagnosis or Correlate to Particular Diseases

DEVICES, SYSTEMS, AND METHODS FOR VIRTUAL STAINING

CROSS REFERENCE TO RELATED APPLICATIONS

This application is a continuation of U.S. patent application Ser. No. 16/911,098, entitled DEVICES, SYSTEMS, AND METHODS FOR VIRTUAL STAINING, filed Jun. 24, 2020 which is a continuation of U.S. patent application Ser. No. 14/224,903, entitled DEVICES, SYSTEMS, AND METHODS FOR VIRTUAL STAINING, filed Mar. 25, 2014, which is a continuation of U.S. patent application Ser. No. 13/843,588, entitled DEVICES, SYSTEMS, AND METHODS FOR VIRTUAL STAINING, filed Mar. 15, 2013, which claims the benefit of U.S. Provisional Patent Application Ser. No. 61/656,930, entitled DEVICES, SYSTEMS, AND METHODS FOR VIRTUAL STAINING, filed Jun. 7, 2012, and U.S. Provisional Patent Application Ser. No. 61/612,925, entitled DEVICES, SYSTEMS, AND METHODS FOR VIRTUAL STAINING, filed Mar. 19, 2012. Each of the foregoing applications is hereby incorporated by reference herein in its entirety.

BACKGROUND

Field

Embodiments relate to the field of imaging biological tissue, and, in particular, to methods, systems, and devices for virtually staining biological tissue for enhanced visualization without actually staining and/or tagging the tissue.

Description

With the development of new technologies, various stains and tags can be attached to biological tissues to enhance contrast of tissue components and thereby improve visibility. Different stains and tags can be used to contrast tissues, cell populations, or organelles within individual cells and to visualize different tissue components depending on the need. However, once a biological tissue is stained with a particular stain or tag to visualize one tissue component, the same tissue generally cannot be stained again with another dye or tag to visualize another tissue component. As such, visualizing another tissue component by use of another dye or tag generally requires using a new tissue sample and increased costs.

SUMMARY

Advancements in technology make it possible to use hyperspectral imaging to virtually stain biological tissue for enhanced visualization without actually staining and/or tagging as described herein. Because the tissue sample is not actually stained, tagged, or otherwise altered, a single tissue sample can be virtually stained with various dyes, tags, and/or other transformations to allow enhanced visualization of as many tissue components as desired. In addition, images of the same biological tissue virtually stained with different dyes, tags, or other transformations can be viewed side-by-side for a more comprehensive analysis. Also, virtual staining can be performed in vivo as well. In certain embodiments, it is also possible to use hyperspectral imaging to provide detailed and objective analysis of a biological tissue sample as described herein.

In one embodiment, a computer-implemented method for virtually staining a tissue sample comprises directing by an electromagnetic radiation source electromagnetic radiation within a bandwidth range on a tissue sample to be virtually stained, detecting by at least one detection device electromagnetic radiation reflected or transmitted from the tissue sample, receiving electronically by a computing system the detected electromagnetic radiation from the at least one detection device, identifying by the computing system a waveform signature associated with each input pixel of an input image of the tissue sample, wherein the input image is generated based on the detected electromagnetic radiation, receiving by the computing system instructions to virtually stain the tissue sample with at least one virtual stain, assigning by the computing system one or more output pixels to each input pixel according to a virtual staining transform, wherein the virtual staining transform comprises mapping data for a virtual stain, wherein the mapping data is used to assign the output pixel based on the waveform signature associated with the input pixel, and generating by the computing system an output image of the tissue sample based on the output pixels, wherein the computing system comprises a computer processor and an electronic storage medium. In some embodiments, the computing system in the above computer-implemented method for virtually staining a tissue sample can comprise one or more computer systems.

In the above computer-implemented method for virtually staining a tissue sample, the virtually stained image can be substantially identical to an image of the tissue sample when treated with an actual stain that corresponds to the virtual stain. In certain embodiments, the actual stain is a dye configured to color certain portions of the tissue sample. In other embodiments, the actual stain is a tag or probe. In other embodiments, the tag or probe is at least one of a group comprising an antibody, an aptamer, and a fluorescent protein. The above computer-implemented method for virtually staining a tissue sample can be performed in vivo. The above computer-implemented method for virtually staining a tissue sample can also be performed in vitro. In the above computer-implemented method for virtually staining a tissue sample, the at least one detection device can be at least one of a group comprising multi-spectrum detector, ultrasound detector, X-ray detector, MRI detector, CT, PET, and PET-CT. In the above computer-implemented method for virtually staining a tissue sample, the computing system can be connected to the electromagnetic radiation source and the at least one detection device over a computer network. Further, in the above computer-implemented method for virtually staining a tissue sample, the electromagnetic radiation source can direct at least one of a group comprising multi-spectrum electromagnetic radiation, X-ray spectrum, ultrasound spectrum, infrared spectrum, MRI spectrum, PET spectrum, and CT spectrum. In some embodiments, the above computer-implemented method for virtually staining a tissue sample further comprises using the determined waveform associated with each pixel to classify a particular disease according to certain criteria. In other embodiments, the certain criteria can comprise whether the particular disease is of a class of diseases that are susceptible to a certain treatment.

In one embodiment, a computer-implemented method of developing a virtual staining transform comprises directing by an electromagnetic radiation source electromagnetic radiation within a bandwidth range on a tissue sample, detecting by at least one detection device electromagnetic radiation reflected or transmitted from the tissue sample, generating by a computing system a first image from the detected electromagnetic radiation from the tissue sample, wherein the first image comprises a plurality of pixels, identifying by the computing system a waveform associated with each one of the plurality of pixels forming the first image, modifying the tissue sample, directing by a light source visible light on the modified tissue sample, detecting by the at least one detection device visible light reflected or transmitted from the modified tissue sample, generating by the computing system a second image from the detected visible light from the modified tissue sample, wherein the second image comprises a plurality of pixels, identifying by the computing system a color composition of each one of the plurality of pixels forming the second image, generating by the computing system a virtual staining transform based on the identified waveform associated with each one of the plurality of pixels forming the first image and the identified color composition of each one of the plurality of pixels forming the second image, and storing in the computing system the virtual staining transform, wherein the computing system comprises a computer processor and an electronic storage medium.

The computer-implemented method of developing a virtual staining transform can further comprise repeating the method for a plurality of tissue samples and combining by the computing system the color composition identified from the second image that corresponds to identical or substantially identical first waveforms according to a pre-stored algorithm. In the above computer-implemented method of developing a virtual staining transform, the modifying can comprise staining the tissue sample with a stain in some embodiments. In other embodiments, the modifying can comprise attaching at least one tag to the tissue sample. In certain embodiments, the tag can be at least one of a group comprising an antibody, an aptamer, and a fluorescent protein. In the above computer-implemented method of developing a virtual staining transform, the at least one detection device can be at least one of a group comprising multi-spectrum detector, ultrasound detector, X-ray detector, Mill detector, CT, PET, and PET-CT. Also in the above computer-implemented method of developing a virtual staining transform, the electromagnetic radiation source can direct at least one of a group comprising multi-spectrum electromagnetic radiation, X-ray spectrum, ultrasound spectrum, infrared spectrum, MM spectrum, PET spectrum, and CT spectrum. In the above computer-implemented method of developing a virtual staining transform, the computing system can comprise one or more computer systems. Further, in the above computer-implemented method of developing a virtual staining transform, the computing system can be connected to the electromagnetic radiation source and the at least one detection device over a computer network.

In one embodiment, a computer-readable, non-transitory storage medium has a computer program stored thereon for causing a suitably programmed computer system to process by one or more computer processors computer-program code by performing a method when the computer program is executed on the suitably programmed computer system, wherein the method comprises directing by an electromagnetic radiation source electromagnetic radiation within a bandwidth range on a tissue sample to be virtually stained, detecting by at least one detection device electromagnetic radiation reflected or transmitted from the tissue sample, receiving electronically by a computing system the detected electromagnetic radiation from the at least one detection device, identifying by the computing system a waveform signature associated with each input pixel of an input image of the tissue sample, wherein the input image is generated based on the detected electromagnetic radiation, receiving by the computing system instructions to virtually stain the tissue sample with at least one virtual stain, assigning by the computing system one or more output pixels to each input pixel according to a virtual staining transform, wherein the virtual staining transform comprises mapping data for a virtual stain, wherein the mapping data is used to assign the output pixel based on the waveform signature associated with the input pixel, and generating by the computing system an output image of the tissue sample based on the output pixels, wherein the computing system comprises a computer processor and an electronic storage medium.

In one embodiment, a computer-readable, non-transitory storage medium has a computer program stored thereon for causing a suitably programmed computer system to process by one or more computer processors computer-program code by performing a method when the computer program is executed on the suitably programmed computer system, wherein the method comprises directing by an electromagnetic radiation source electromagnetic radiation within a bandwidth range on a tissue sample, detecting by at least one detection device electromagnetic radiation reflected or transmitted from the tissue sample, generating by a computing system a first image from the detected electromagnetic radiation from the tissue sample, wherein the first image comprises a plurality of pixels, identifying by the computing system a waveform associated with each one of the plurality of pixels forming the first image, modifying the tissue sample, directing by a light source visible light on the modified tissue sample, detecting by the at least one detection device visible light reflected or transmitted from the modified tissue sample, generating by the computing system a second image from the detected visible light from the modified tissue sample, wherein the second image comprises a plurality of pixels, identifying by the computing system a color composition of each one of the plurality of pixels forming the second image, generating by the computing system a virtual staining transform based on the identified waveform associated with each one of the plurality of pixels forming the first image and the identified color composition of each one of the plurality of pixels forming the second image, and storing in the computing system the virtual staining transform, wherein the computing system comprises a computer processor and an electronic storage medium.

In one embodiment, a system for virtually staining a tissue sample comprises an electromagnetic radiation source configured to direct electromagnetic radiation within a bandwidth on a tissue sample to be virtually stained, at least one detection device configured to detect electromagnetic radiation reflected or transmitted from the tissue sample, and a storage computer system comprising a computer processor configured to execute modules comprising at least, a data receiving module configured to receive electronically the detected electromagnetic radiation from the at least one detection device, a pixel analysis module configured to identify a waveform signature associated with each input pixel of an input image of the tissue sample, wherein the input image is generated based on the detected electromagnetic radiation, a user instructions module configured to receive instructions to virtually stain the tissue sample with at least one virtual stain, a virtual transform module configured to assign one or more output pixels to each input pixel according to a virtual staining transform, wherein the virtual staining transform comprises mapping data for a virtual stain, wherein the mapping data is used to assign the output pixel based on the waveform signature associated with the input pixel, and an image generation module configured to generate an output image of the tissue sample based on the output pixels.

In one embodiment, a system for developing a virtual staining transform comprises an electromagnetic radiation source configured to direct electromagnetic radiation within a bandwidth range on a tissue sample, at least one detection device configured to detect electromagnetic radiation reflected or transmitted from the tissue sample, a light source configured to direct visible light on a modified tissue sample, at least one detection device configured to detect visible reflected or transmitted from the modified tissue sample, and a storage computer system comprising a computer processor configured to execute modules comprising at least an initial image generation module configured to generate a first image from the detected electromagnetic radiation from the tissue sample, wherein the first image comprises a plurality of pixels, an initial pixel analysis module configured to identify a waveform associated with each one of the plurality of pixels forming the first image, a final image generation module configured to generate a second image from the detected visible from the modified tissue sample, wherein the second image comprises a plurality of pixels, a final pixel analysis module configured to identify a color composition of each one of the plurality of pixels forming the second image, a virtual staining transform generation module configured to generate a virtual staining transform based on the identified waveform associated with each one of the plurality of pixels forming the first image and the identified color composition of each one of the plurality of pixels forming the second image, and a virtual staining transform storage module configured to store the virtual staining transform.

In one embodiment, a computer-implemented method for virtually staining a tissue sample comprises obtaining by a computing system an electronic image of the tissue sample, determining by the computing system a vector signature or waveform signature associated with each pixel in the electronic image, generating by the computing system an output pixel for each pixel in the electronic image based on inputting the determined vector signature or waveform signature into a virtual staining transform, and outputting by the computing system a virtually stained image of the tissue sample based on the generated output pixels, wherein the computing system comprises a computer processor and an electronic storage medium. In some embodiments, the computing system in the above computer-implemented method for virtually staining a tissue sample can comprise one or more computer systems.

In the above computer-implemented method for virtually staining a tissue sample, the virtually stained image can be substantially identical to an image of the tissue sample when stained with an actual stain. In some embodiments, the actual stain can be a dye configured to color certain portions of the tissue sample. In other embodiments, the actual stain can be a tag or probe. In certain embodiments, the tag or probe can be at least one of a group comprising an antibody, an aptamer, and a fluorescent protein. The above computer-implemented method for virtually staining a tissue sample can be performed in vivo. The above computer-implemented method for virtually staining a tissue sample can also be performed in vitro.

In one embodiment, a computer-readable, non-transitory storage medium has a computer program stored thereon for causing a suitably programmed computer system to process by one or more computer processors computer-program code by performing a method when the computer program is executed on the suitably programmed computer system, wherein the method comprises obtaining by a computing system an electronic image of the tissue sample, determining by the computing system a vector signature or waveform signature associated with each pixel in the electronic image, generating by the computing system an output pixel for each pixel in the electronic image based on inputting the determined vector signature or waveform signature into a virtual staining transform, and outputting by the computing system a virtually stained image of the tissue sample based on the generated output pixels, wherein the computing system comprises a computer processor and an electronic storage medium.

In one embodiment, a system for virtually staining a tissue sample comprises a storage computer system comprising a computer processor configured to execute modules comprising at least a data receiving module configured to obtain electronically an electronic image of the tissue sample, a pixel analysis module configured to determine a vector signature or waveform signature associated with each pixel in the electronic image, a virtual transform module configured to generate an output pixel for each pixel in the electronic image based on inputting the determined vector signature or waveform signature into a virtual staining transform, and an output module configured to output a virtually stained image of the tissue sample based on the generated output pixels.

For purposes of this summary, certain aspects, advantages, and novel features are described herein. It is to be understood that not necessarily all such advantages may be achieved in accordance with any particular embodiment. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The foregoing and other features, aspects and advantages are described in detail below with reference to the drawings of various embodiments, which are intended to illustrate and not to limit the disclosure. The drawings comprise the following figures in which:

FIGS. 4A-4F are block diagrams depicting overviews of embodiments of methods of collecting data and building virtual staining transforms.

FIGS. 6A-6B are block diagrams depicting overviews of embodiments of methods of collecting data and building a virtual staining transform for a particular stain under multiple electromagnetic radiation sources.

FIGS. 8A-8B are block diagrams depicting overviews of embodiments of methods of collecting data and building a three-dimensional virtual staining transform for a particular stain.

FIGS. 9A-9B are block diagrams depicting overviews of embodiments of methods of collecting data and building a virtual staining transform for a particular stain with volume averaging.

FIG. 11 is a block diagram depicting an overview of some embodiments of methods of virtually staining that generate more than one output pixel for each input pixel.

FIGS. 12A-12B are block diagrams depicting overviews of embodiments of methods of virtually staining a single tissue sample with multiple virtual stains using a virtual staining transform.

FIG. 12C depicts an example of one embodiment of a screen view of a single tissue sample virtually stained by multiple virtual stains.

FIGS. 13A-13D depict examples of virtually stained images in comparison to an actually stained slide and spectral data of underlying pixels.

FIGS. 15A and 15B depict examples of identification of biological species using hyperspectral imaging.

DETAILED DESCRIPTION OF THE EMBODIMENTS

Figure 1A:
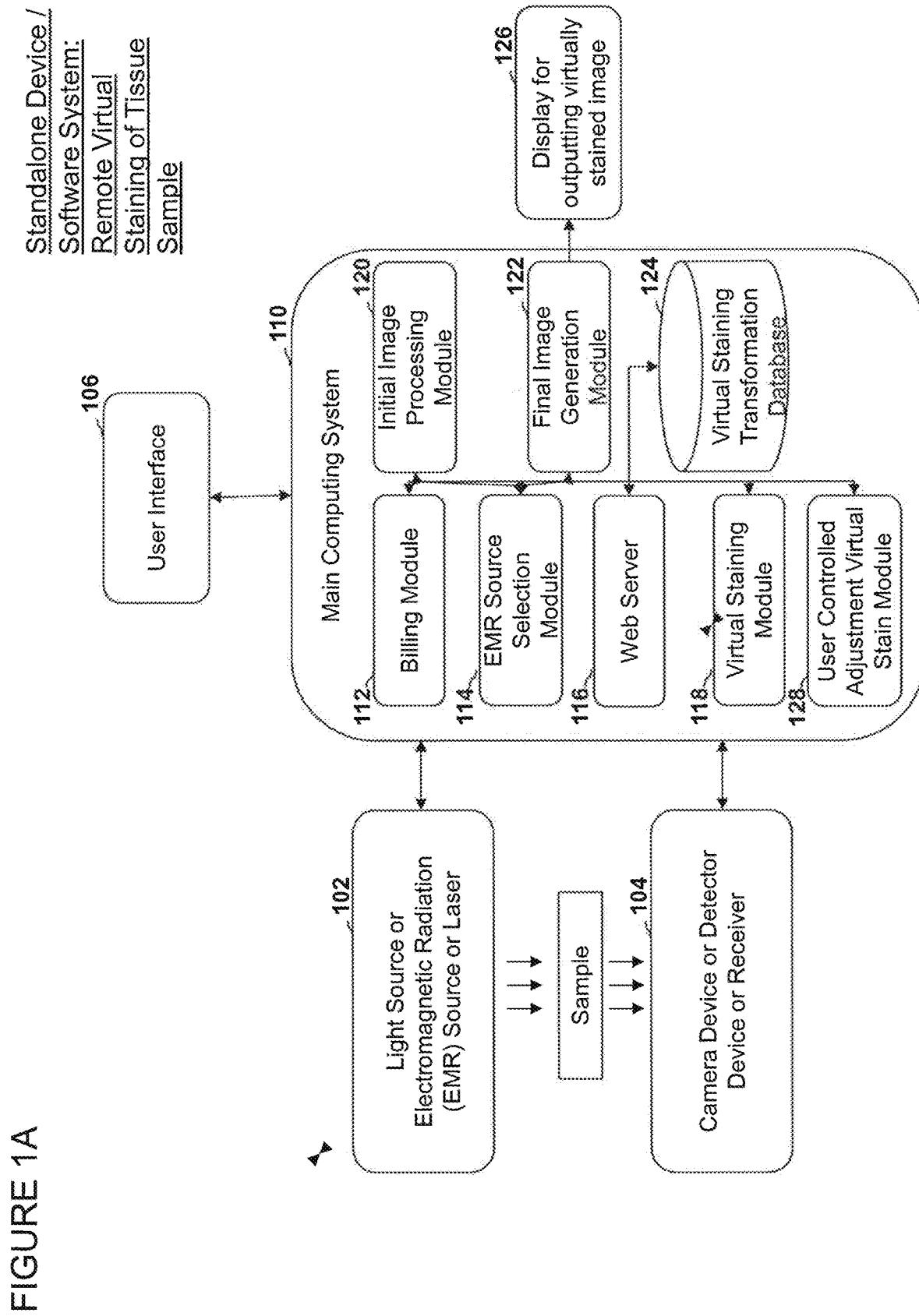
FIG. 1A is a block diagram depicting a high level overview of one embodiment of a standalone system or software system for virtually staining biological tissue.

Embodiments will now be described with reference to the accompanying figures. The terminology used in the description presented herein is not intended to be interpreted in any limited or restrictive manner, simply because it is being utilized in conjunction with a detailed description of certain specific embodiments. Furthermore, embodiments may comprise several novel features, no single one of which is solely responsible for its desirable attributed or which is essential to practicing the embodiments herein described.

As used herein, the terms "sample," "tissue sample," "biological sample," and "specimen" may be used interchangeably, and the foregoing terms comprise without limitation tissue samples, tissue specimen, bulk tissue, surgical site, site, bacteria, cell, cell components, a substance on an agar plate, or any material or surface off of which electromagnetic radiation can be reflected. A sample can be analyzed in vivo or in vitro.

As used herein, the terms "camera," "camera device," "detector," "detector device," "receiver," and "receiver device" may be used interchangeably, and the foregoing terms comprise without limitation a multi-spectrum detector, ultrasound detector, X-ray detector, MRI detector, CT, PET, PET-CT, or any device capable of detecting reflected or transmitted radiation of some sort.

As used herein, the terms "stain" and "staining" are broad terms and can include without limitation staining with a dye or a stain, immunohistochemical staining, aptamer staining, tagging, chemical staining, antibody staining, or any other alteration to a tissue sample.

As used herein, the terms "pixel," "group of pixels," "unit of pixels" or the like are broad terms and can include without limitation any individual unit of pixel or pixels of an image. The term "pixel" as used herein is a broad term and can include without limitation a point or area in an image. The term "pixel waveform" as used herein is a broad term and can include without limitation a waveform detected at a position of a particular pixel. The waveform is a representation of the detected spectrum wavelength(s) and amplitude(s) at a particular point in the image. They are not to be limited to refer to any particular unit of pixel or pixels.

The disclosure herein provides methods, systems, and devices for virtually staining biological tissue for enhanced visualization without use of an actual dye or tag. In an embodiment, virtual staining is accomplished by detecting waveforms associated with the position of each pixel of an unstained tissue sample and applying a virtual staining transform to each of those pixels to generate an output image that is substantially similar to an image of the tissue sample when stained with an actual stain or other desired transform. A virtual staining transform can be developed by detecting waveforms associated with the position of each pixel of an unstained tissue sample and the result of the same pixel after staining, tagging, or other transformation or alteration when viewed under a particular type of light, such as visible light for example.

With the development of new technologies, biological tissues can be stained with various dyes and/or attached with various tags to enhance contrast of tissue components and thereby improve visibility. Different stains and/or tags can be used to contrast bulk tissues, cell populations, and/or organelles within individual cells, and/or to visualize different tissue components depending on the need. However, once a biological tissue is stained with a particular dye and/or tag to visualize one tissue component, the same tissue generally cannot be stained again with another dye and/or tag to visualize another tissue component. As such, visualizing another tissue component by use of another dye or tag generally requires using a new tissue sample, which may or may not exhibit the same characteristics, or which may or may not be available.

By employing the methods, systems, and devices for virtually staining biological tissue for enhanced visualization described herein, one can generate virtually stained images of a biological tissue without actually staining or tagging the tissue. Because the tissue sample is not actually stained with a dye and/or a tag, the same tissue sample can be virtually stained with various dyes and tags to allow enhanced visualization of as many tissue components as desired. In addition, images of the same biological tissue virtually stained with different dyes and tags can be viewed side-by-side for a more comprehensive analysis and/or for a direct one to one comparison of the tissue sample. Furthermore, virtual staining can be performed in vivo as well, allowing examiners to observe virtually stained tissue images without having to surgically extract or isolate the sample to be examined from the surrounding tissue.

In some embodiments, electromagnetic radiation is directed at a tissue sample. A detection device detects electromagnetic radiation that is transmitted, reflected, or otherwise not absorbed by the tissue sample. In an embodiment, none of the spectrum data is subtracted or otherwise discarded but rather the system is configured to analyze the entire spectrum data available at each point of an image. The whole spectrum data is used by an image generating device or system to generate an initial image and a computing system analyzes the contents of the generated image pixel-by-pixel or according some predetermined unit of pixels. The chemical properties of each pixel or group of pixels is disclosed in the reflected, transmitted, or otherwise not absorbed light by the tissue sample in the form of a waveform or waveform signature. Accordingly, using a pre-developed and pre-stored virtual staining transform, the computing system can apply the transform to each pixel to obtain an output of each pixel or group of pixels after virtually staining with a virtual stain, tag, or transform of choice.

The virtual staining transform comprises data that can map an input pixel of a certain waveform to an output pixel and/or an associated output waveform. A single input pixel of a certain waveform can be associated with more than one output pixel, wherein each output pixel corresponds to the result of an input pixel after virtually staining with a particular stain, dye, or the like. The output pixel can be of a particular color or grayscale. Such output pixels are combined by the computing system to generate a virtually stained image of the tissue sample. In other words, the computing system pseudo-colors the initial detected image to produce a virtually stained image.

In an embodiment, the system disclosed herein is distinguishable from other known methods and applications of imaging and hyperspectral imaging, such as with quantum dots. For example, in some embodiments, the system can be configured to analyze what would be considered background spectra for other imaging applications. Other imaging applications in the life sciences, such as in connection with quantum dots, are generally employed to search for specific components or irregularities in the sample that are often tagged or labeled with reporter molecules. Because the purpose is to specifically locate and image those tagged and/or probed components, background spectra from the non-labeled portions of the sample are simply subtracted for various reasons, such as for faster processing. However, in certain embodiments of the system illustrated herein, the system can be configured to analyze only the background spectra, which would have been subtracted by other hyperspectral imaging applications, as opposed to analyzing the entire spectra. Alternatively, in other embodiments, the system can be configured to analyze the entire spectra detected from the tissue sample. Because the systems illustrated here focus on the background spectra, the entire spectrum, or portions thereof, the system can be configured to better visualize different tissue or cellular characteristics and/or overlapping features or entities, which can be observed at the same time. Such vast data is subsequently analyzed to determine the waveform associated with each pixel, which is in turn mapped according to the virtual staining transform.

FIG. 1A is a block diagram illustrating a high level overview of one embodiment of a standalone system or software system for virtually staining biological tissue. In the depicted embodiment, a main computing system 110 is connected to at least one of a light source or electromagnetic radiation source or laser 102, a camera device or detector device or receiver 104, a user interface 106, and a display for outputting virtually stained images 126.

A user instructs the main computing system 110 via the user interface 106 to direct an electromagnetic radiation (EMR) source 102 at a sample. The detector device 104 detects reflected, transmitted, or otherwise not absorbed radiation from the sample and sends the detected data to the main computing system 110. A user instructs the main computing system 110 via the user interface 106 to apply a particular virtual stain, tag, or other transformation to the detected image. The main computing system 110 can be configured to generate a virtually stained image according to the user input, and the virtually stained image can be displayed on a display for outputting virtually stained images 126.

In certain embodiments, the main computing system 110, as depicted in FIG. 1A, comprises but is not limited to a billing module 112, an EMR source selection module 114, a web server 116, a virtual staining module 118, an initial image processing module 120, a final image generation module 122, a virtual staining transformation database 124, and a user controlled adjustment virtual stain module 128. In some embodiments, the main computing system 110 can be configured, for example, among other things, to: communicate with the user interface 106; instruct the EMR source 102 to direct a certain electromagnetic radiation at a sample; receive detected image data from the detector device 104; virtually stain or otherwise transform the detected image; instruct a display for outputting virtually stained images 126 to display the virtually stained or otherwise transformed image; and/or enable billing processes for each transformation of images.

Upon receiving input from a user interface 106, the main computing system 110 instructs the EMR source 102 to direct a particular EMR source to the sample. In some embodiments, the EMR source selection module 114 of the main computing system 110 is configured to instruct the EMR source 102 to direct a particular EMR source to the sample. In certain embodiments, the EMR source can be configured to direct multi-spectrum electromagnetic radiation, X-ray, ultrasound, infrared, other electromagnetic radiation, MM, CT, PET, PET-CT, or any combination thereof. After the detector device 104 detects the transmitted or reflected radiation from the sample, such detected image data is analyzed by the main computing system 110 or the initial image processing module 120 thereof in some embodiments.

In some embodiments, the received image data is analyzed pixel by pixel, point by point, or area by area. In other embodiments, the received image data is analyzed according to a preset group of pixels. In some embodiments, the image data comprises waveform data associated with each pixel position in the image. For example, for each pixel in an image, there is an associated waveform signature. The waveform signature can represent the detected wavelengths and corresponding amplitudes that are detected by the detector at each position in the tissue sample (for example, see waveform signature 416 in FIG. 4A). Each waveform corresponding to each pixel or group of pixels is analyzed by the main computing system 110 or initial image processing module 120.

In certain embodiments, after the initial image is analyzed or concurrently, the initial image is virtually stained or otherwise transformed by the main computing system 110 or a virtual staining module 118 thereof. To do so, in some embodiments, the virtual staining module 118 accesses a virtual staining transformation database 124. The virtual staining transformation database 124 contains data related to how a pixel or group of pixels associated with a particular waveform is transformed when actually stained, when a tag is attached, or some other transform or alteration. In some embodiments, such data can be updated periodically or in real-time.

In some embodiments, once the virtual staining module 118 virtually stains or otherwise transforms each pixel or group of pixels of the initial image or concurrently, the final image generation module 122 combines each transformed pixel or group of pixels to generate a final transformed image. This virtually stained or otherwise transformed image is displayed to the user on a display for outputting virtually stained images 126.

A user can, in some embodiments, instruct the virtual staining module 118 to apply a particular stain or transformation to the initial image via the user interface 106. The user interface communicates the user's instructions to the user controlled adjustment virtual stain module 128. In some embodiments, the user controlled adjustment virtual stain module 128 is further configured to receive user instructions from the user interface 106 before or after a virtually stained image is generated to make slight changes in the virtual staining. For example, the user can instruct the user controlled adjustment virtual stain module 128 to apply different virtual stains to different portions of the initial image, to apply less or more of a certain virtual stain to a particular portion of the initial image, or to enhance resolution of a particular portion of the virtually stained image.

In some embodiments, the standalone device comprises the main computing system, some or all of its components, and a user interface, which are connected to a conventional light source, EMR source, or laser a camera device or a detector, and a display. In other embodiments, the standalone device comprises all of the above components or some subset thereof. In yet other embodiments, a software system is configured to instruct and use conventional system components to obtain the functions described above. In certain embodiments, the system components discussed above or a subset thereof are conventional devices that are widely available.

Figure 1B:
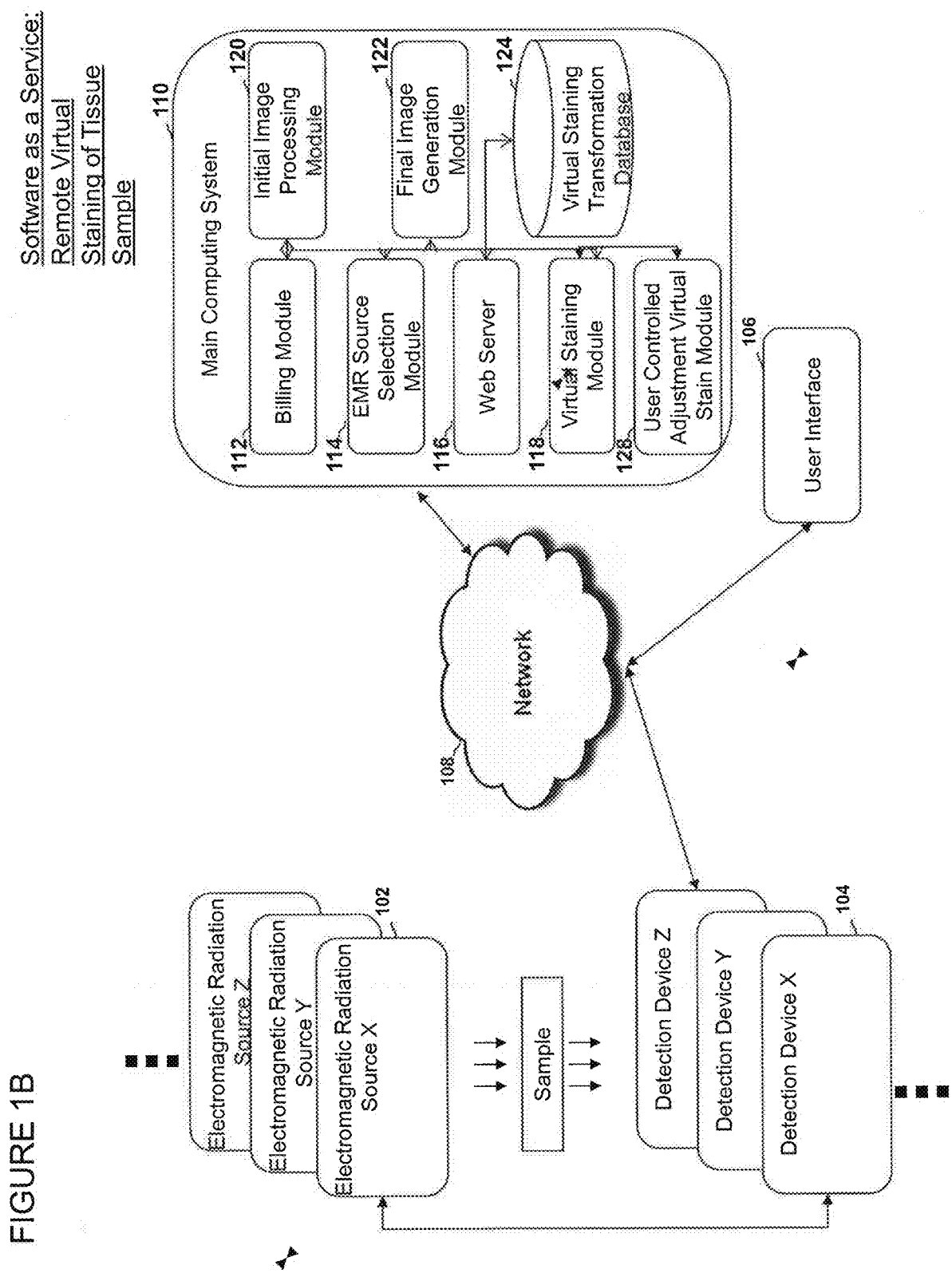
FIG. 1B is a block diagram depicting a high level overview of one embodiment of a system for virtually staining biological tissue remotely by providing virtual staining services over a network.

FIG. 1B is a block diagram illustrating a high level overview of one embodiment of a system for virtually staining biological tissue by remotely providing services over a network. For example, the main computing system 110 can be configured to receive or access over an electronic network images of a tissue sample to be processed and virtually stained by the computing system 110. In this embodiment, the images are generated at a location remote or distinct from the computing system. The images can be stored in a database that is remote from the computing system 110 or the images can be transmitted to the computing system 110 through an electronic network. The computing system 110 can be configured to transmit the virtually stained image to a remote location or store the virtually stained image in a database located in a remote location. Alternatively, as in the depicted embodiment, a main computing system 110 is connected, directly or indirectly, to at least one detection device 104 and a user interface 106 over a computer network 108. In some embodiments, at least one electromagnetic radiation source 102 is also connected to the main computing system 110 via the computer network 108. In other embodiments, the at least one electromagnetic radiation source 102 is not connected to the main computing system 110 over the computer network 108 and is locally maintained and controlled. In yet other embodiments, the at least one electromagnetic radiation source 102 is connected to the at least one detection device 104.

The network may comprise one or more internet connections, secure peer-to-peer connections, secure socket layer (SSL) connections over the internet, virtual private network (VPN) connections over the internet, or other secure connections over the internet, private network connections, dedicated network connections (for example, IDSN, T1, or the like), wireless or cellular connections, or the like or any combination of the foregoing.

In some embodiments, a user can select using the user interface 106 a particular electromagnetic radiation source 102 to be directed at a tissue sample. In other embodiments, the particular electromagnetic radiation source 102 to be directed at a tissue sample is selected locally via another user interface that is not in communication with the main computing system 110.

The selected at least one electronic radiation source is directed at the tissue sample. The at least one detection device 104 detects electromagnetic radiation that is transmitted, reflected, or otherwise not absorbed by the tissue sample. Such detected data is subsequently transmitted to the main computing system 110 over the computer network.

In some embodiments, an initial image processing module 120 of the main computing system 110 receives the data from the at least one detection device 104 and analyzes the received data in a similar manner as described above in relation to FIG. 1A. In certain embodiments, once the initial image is analyzed by the initial image processing module 120 or concurrently, the initial image is virtually stained or otherwise transformed by a virtual staining module 118 in a similar manner as described above in relation to FIG. 1A.

In some embodiments, once the virtual staining module 118 virtually stains or otherwise transforms each pixel or group of pixels of the initial image or concurrently, the final image generation module 122 combines each transformed pixel or group of pixels to generate a final transformed image. This virtually stained or otherwise transformed image is transmitted to the user interface 106 over the computer network 108. In other embodiments, the virtually stained or otherwise transformed image is transmitted to another computing system or a mobile device of the user's choice via the web server 116 and the computer network 108. The user interface, another computing system, or mobile device can display the virtually stained or otherwise transformed images to the user. In certain embodiments, a billing module 112 of the main computing system 110 generates a bill depending on the number of different virtual stains applied and/or the number of different samples that were virtually stained or otherwise transformed.

A user can, in an embodiment, instruct the virtual staining module 118 to apply a particular stain or transformation to the initial image via the user interface 106 and over the computer network. The user interface communicates the user's such instructions to the user controlled adjustment virtual stain module 128. In some embodiments, the user controlled adjustment virtual stain module 128 is further configured to receive user instructions from the user interface 106 before or after a virtually stained image is generated to make slight changes in the virtual staining as described above in relation to FIG. 1A.

In some embodiments, as illustrated in FIG. 1B, the main computing system 110 is not physically connected to the electromagnetic radiation source 102 or the detection device 104. Rather they are connected over a network 108. In such embodiments, a user need not purchase or locally store contents of the virtual staining transformation database 124, but communicates with the main computing system 110 located at a third-party location for such purposes.

Computing System

Figure 2:
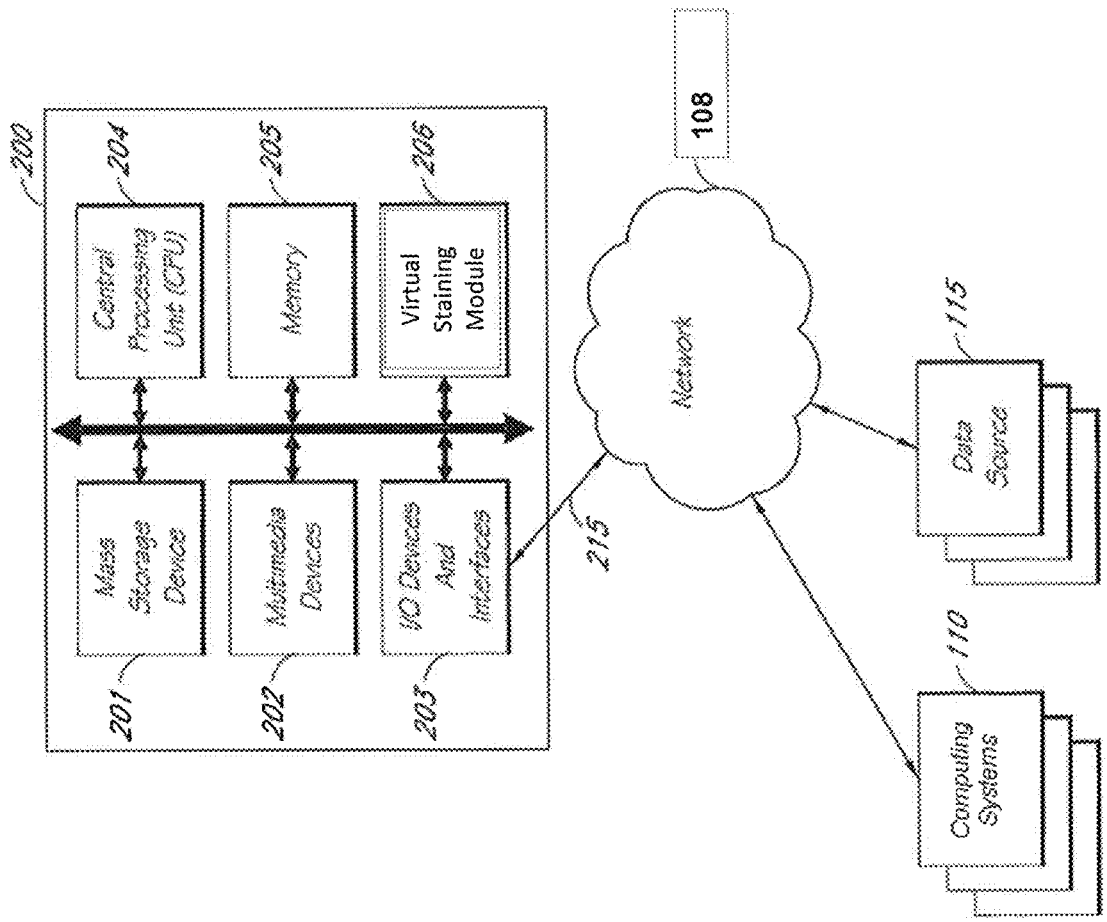
FIG. 2 is a block diagram depicting one embodiment of a computer hardware system configured to run software for implementing one or more embodiments of the virtual staining system described herein.

In some embodiments, the computer clients and/or servers described above take the form of a computing system 200 illustrated in FIG. 2, which is a block diagram of one embodiment of a computing system that is in communication with one or more computing systems 110 and/or one or more data sources 115 via one or more networks 210. The computing system 200 may be used to implement one or more of the systems and methods described herein. In addition, in one embodiment, the computing system 200 may be configured to virtually stain or otherwise transform a sample. While FIG. 2 illustrates one embodiment of a computing system 200, it is recognized that the functionality provided for in the components and modules of computing system 200 may be combined into fewer components and modules or further separated into additional components and modules.

Virtual Staining Module

In one embodiment, the system 200 comprises a virtual staining module 206 that carries out the functions described herein with reference to transforming an initial image received from a detection device 104 configured to detect reflected and transmitted electromagnetic radiation off of a sample. The virtual staining module 206 may be executed on the computing system 200 by a central processing unit 204 discussed further below.

In general, the word "module," as used herein, refers to logic embodied in hardware or firmware, or to a collection of software instructions, possibly having entry and exit points, written in a programming language, such as, for example, COBOL, CICS, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

Computing System Components

In one embodiment, the computing system 200 also comprises a mainframe computer suitable for controlling and/or communicating with large databases, performing high volume transaction processing, and generating reports from large databases. The computing system 200 also comprises a central processing unit ("CPU") 204, which may comprise a conventional microprocessor. The computing system 200 further comprises a memory 205, such as random access memory ("RAM") for temporary storage of information and/or a read only memory ("ROM") for permanent storage of information, and a mass storage device 201, such as a hard drive, diskette, or optical media storage device. Typically, the modules of the computing system 200 are connected to the computer using a standards based bus system. In different embodiments, the standards based bus system could be Peripheral Component Interconnect (PCI), Microchannel, SCSI, Industrial Standard Architecture (ISA) and Extended ISA (EISA) architectures, for example.

The computing system 200 comprises one or more commonly available input/output (I/O) devices and interfaces 203, such as a keyboard, mouse, touchpad, and printer. In one embodiment, the I/O devices and interfaces 203 comprise one or more display devices, such as a monitor, that allows the visual presentation of data to a user. More particularly, a display device provides for the presentation of GUIs, application software data, and multimedia presentations, for example. In the embodiment of FIG. 2, the I/O devices and interfaces 203 also provide a communications interface to various external devices. The computing system 200 may also comprise one or more multimedia devices 202, such as speakers, video cards, graphics accelerators, and microphones, for example.

Computing System Device/Operating System

The computing system 200 may run on a variety of computing devices, such as, for example, a server, a Windows server, an Structure Query Language server, a Unix server, a personal computer, a mainframe computer, a laptop computer, a cell phone, a personal digital assistant, a kiosk, an audio player, and so forth. The computing system 200 is generally controlled and coordinated by operating system software, such as z/OS, Windows 95, Windows 98, Windows NT, Windows 2000, Windows XP, Windows Vista, Windows 7, Linux, BSD, SunOS, Solaris, or other compatible operating systems. In Macintosh systems, the operating system may be any available operating system, such as MAC OS X. In other embodiments, the computing system 200 may be controlled by a proprietary operating system. Conventional operating systems control and schedule computer processes for execution, perform memory management, provide file system, networking, and I/O services, and provide a user interface, such as a graphical user interface ("GUI"), among other things.

Network

In the embodiment of FIG. 2, the computing system 200 is coupled to a network 108, such as a LAN, WAN, or the Internet, for example, via a wired, wireless, or combination of wired and wireless, communication link 215. The network 108 communicates with various computing devices and/or other electronic devices via wired or wireless communication links. In the embodiment of FIG. 2, the network 108 is communicating with one or more computing systems 110 and/or one or more data sources 115.

Access to the virtual staining module 206 of the computer system 200 by computing systems 110 and/or by data sources 115 may be through a web-enabled user access point such as the computing systems' 110 or data source's 115 personal computer, cellular phone, laptop, or other device capable of connecting to the network 108. Such a device may have a browser module is implemented as a module that uses text, graphics, audio, video, and other media to present data and to allow interaction with data via the network 108.

The browser module may be implemented as a combination of an all points addressable display such as a cathode-ray tube (CRT), a liquid crystal display (LCD), a plasma display, or other types and/or combinations of displays. In addition, the browser module may be implemented to communicate with input devices 203 and may also comprise software with the appropriate interfaces which allow a user to access data through the use of stylized screen elements such as, for example, menus, windows, dialog boxes, toolbars, and controls (for example, radio buttons, check boxes, sliding scales, and so forth). Furthermore, the browser module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 200 may comprise a physical or logical connection established between a remote microprocessor and a mainframe host computer for the express purpose of uploading, downloading, or viewing interactive data and databases on-line in real time. The remote microprocessor may be operated by an entity operating the computer system 200, including the client server systems or the main server system, an/or may be operated by one or more of the data sources 115 and/or one or more of the computing systems. In some embodiments, terminal emulation software may be used on the microprocessor for participating in the micro-mainframe link.

In some embodiments, computing systems 110 who are internal to an entity operating the computer system 200 may access the virtual staining module 206 internally as an application or process run by the CPU 204.

User Access Point

In an embodiment, a user access point or user interface 106 comprises a personal computer, a laptop computer, a cellular phone, a GPS system, a Blackberry® device, a portable computing device, a server, a computer workstation, a local area network of individual computers, an interactive kiosk, a personal digital assistant, an interactive wireless communications device, a handheld computer, an embedded computing device, or the like.

Other Systems

In addition to the systems that are illustrated in FIG. 2, the network 108 may communicate with other data sources or other computing devices. The computing system 200 may also comprise one or more internal and/or external data sources. In some embodiments, one or more of the data repositories and the data sources may be implemented using a relational database, such as DB2, Sybase, Oracle, CodeBase and Microsoft® SQL Server as well as other types of databases such as, for example, a flat file database, an entity-relationship database, and object-oriented database, and/or a record-based database.

Overview of Developing a Virtual Staining Transform

Figure 3A:
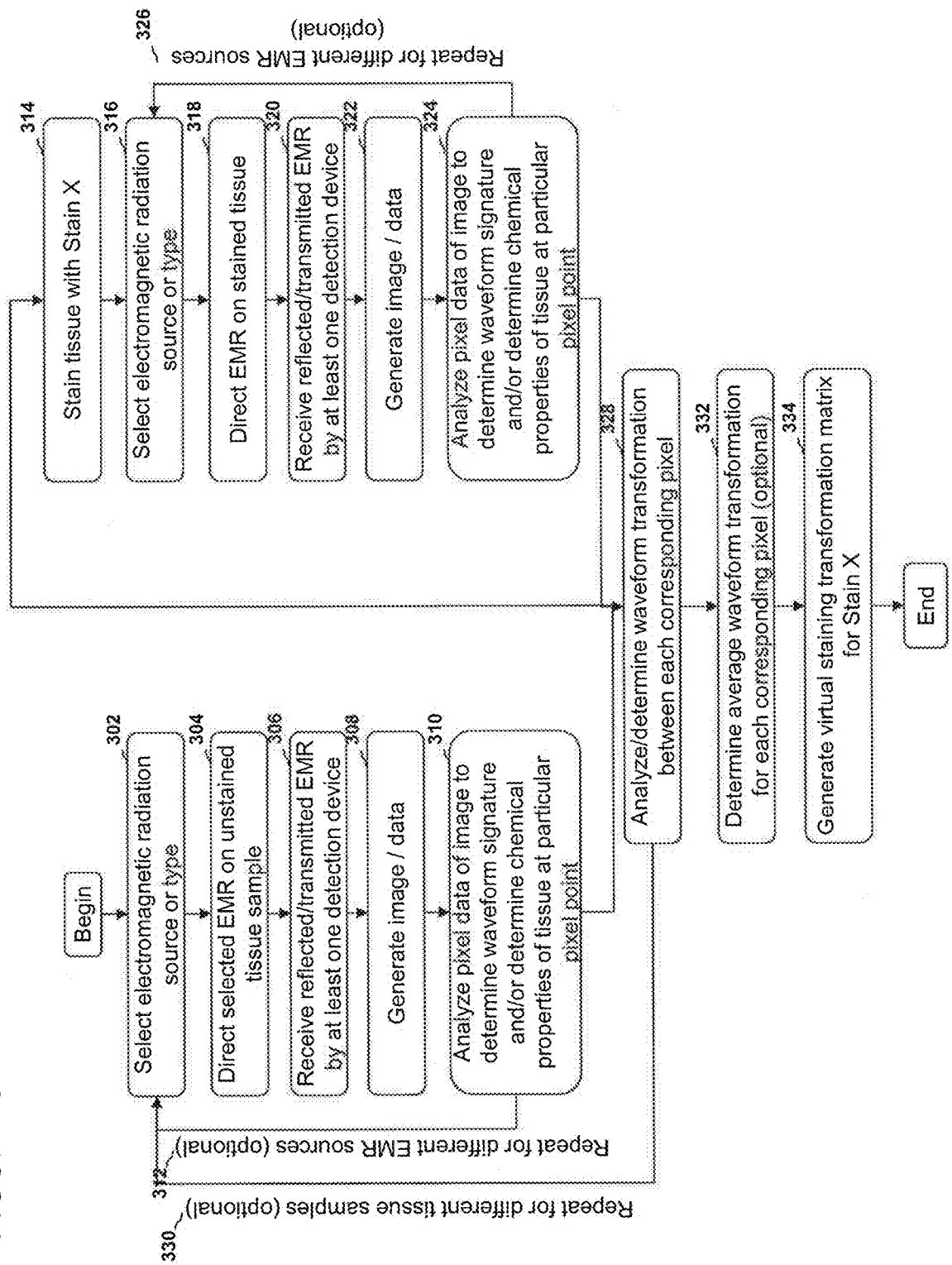
FIGS. 3A-3B are block diagrams depicting overviews of embodiments of methods of collecting data and building a virtual staining transform for a particular stain under different types of electromagnetic radiation.
Figure 3B:
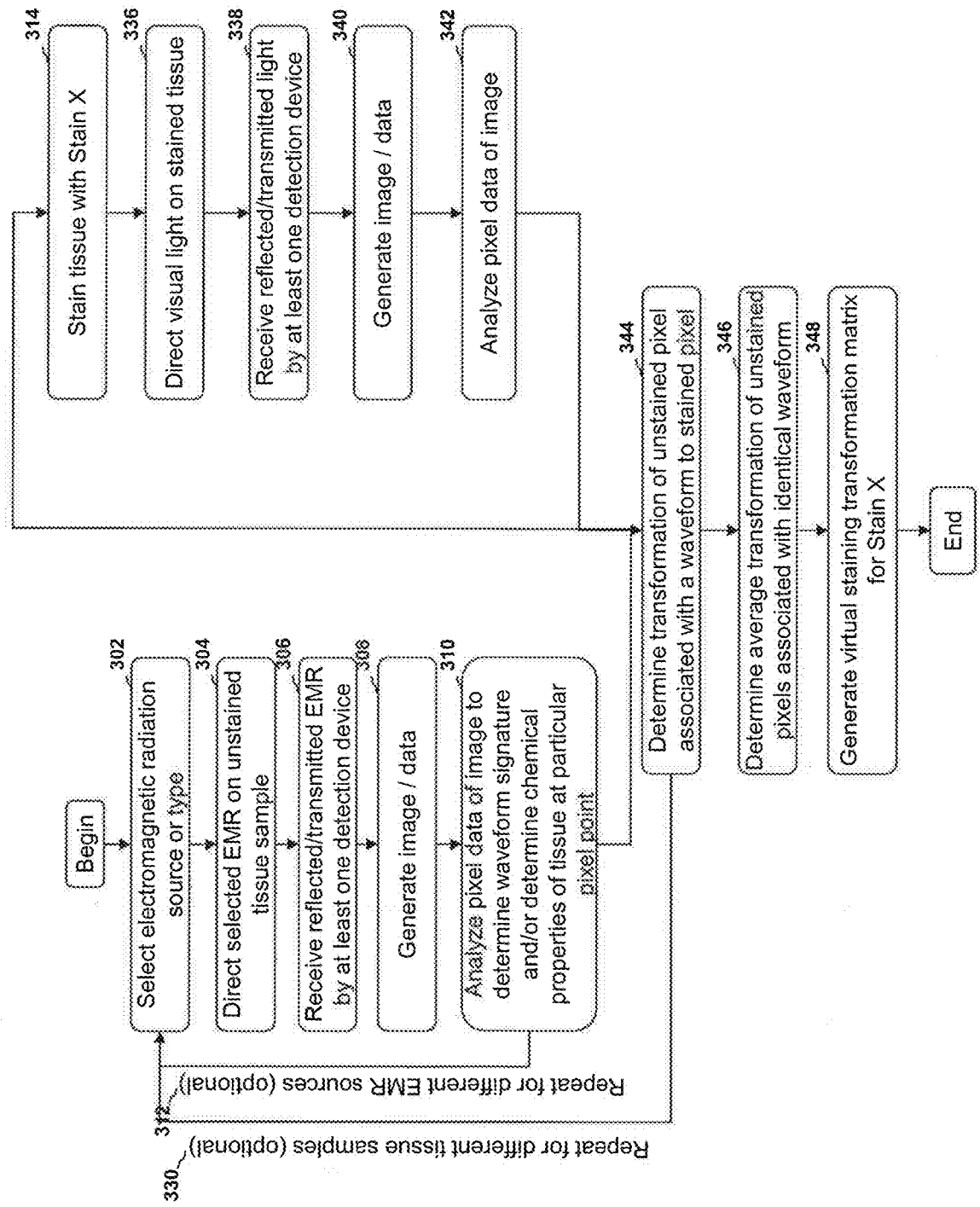

In some embodiments, as illustrated in FIGS. 3A-3B, data of various tissue samples that are actually stained with various stains is collected and stored in order to build a virtual staining transformation database. FIGS. 3A-3B are block diagrams depicting overviews of embodiments of computer-implemented methods of collecting data and building a virtual staining transform for a particular stain, tag, or other transform. The computer-implemented method can be employed for one or more different types of electromagnetic radiation. In some embodiments, the whole process or selected blocks of FIGS. 3A-3B are repeated for different stains.

Specifically, at block 302, a particular electromagnetic radiation source is selected, which is subsequently directed at an unstained tissue sample or other sample at block 304. The particular electromagnetic radiation can be multi-spectrum electromagnetic radiation, visible light, X-ray, ultrasound, infrared, Mill, PET and/or CT, or any other imaging modality currently existing or to be developed in the future. For example, the electromagnetic radiation can be of wavelengths from about 400 nm to about 900 nm or above or other light with a wavelength band of any other range. In some embodiments, electromagnetic radiation that is transmitted, reflected, or otherwise not absorbed by the sample is detected by at least one detection device at block 306. In certain embodiments, more than one detection device can be utilized to reduce error in detection or to collect three-dimensional data.

Based on the detected data, an initial image is generated at block 308. In some embodiments, each pixel or group of pixels in the initial image is associated with a waveform signature detected based on the detected data. In some embodiments, a computing system analyzes this initial image and detects the waveform associated with each pixel or group of pixels at block 310. In some embodiments, the computing system is configured to determine the chemical properties of tissue at a particular pixel point or group of pixels. In certain embodiments, blocks 302 through 310 can be repeated to store initial images and the associated waveform signature data of unstained tissue samples under different types of electromagnetic radiation sources as depicted by 312.

In some embodiments, the sample is actually stained with a dye(s) or is attached to a tag(s) at block 314. Further, in the embodiment illustrated in FIG. 3A, an electromagnetic radiation source is selected at block 316, which is directed at the stained, physically, chemically or otherwise transformed tissue at block 318. The transmitted, reflected, or otherwise not absorbed electromagnetic radiation is detected by at least one detection device at block 320. In some embodiments, more than one detection device can be utilized to reduce error in detection or to collect three-dimensional data.

Based on the detected data, a final image is generated at block 322. In some embodiments, each pixel or group of pixels in the final image is associated with a waveform signature. A computing system analyzes this final image and detects the waveform associated with each pixel or group of pixels at block 324. In other embodiments, the computing system is configured to determine the chemical properties of the stained or otherwise altered tissue at a particular point or area. In certain embodiments, the blocks 316 through 324 can be repeated to store final images, and the associated waveform signature data, of a stained or otherwise transformed tissue sample under different types of electromagnetic radiation sources as depicted by 326.

In another embodiment, the unstained tissue sample is not actually stained or tagged. Rather, the initial image itself is colored or is otherwise transformed according to a user's choice to generate a final image. For example, in embodiments where a virtual staining transform is being developed for imaging modalities including but not limited to X-ray, ultrasound, infrared, MRI, PET and/or CT, a user can selectively color or otherwise transform the initial image to a final image that is more helpful to understand or analyze.

With both the initial image(s) of an unstained sample and the final image(s) of an actually stained or otherwise transformed sample stored, the computing system of an embodiment can identify how an input pixel of the unstained sample associated with a particular waveform resulted in an output pixel associated with a particular waveform after the staining or other transformation at block 328. To do so, in some embodiments, the computing system identifies and stores the waveform signatures associated with each corresponding pixel or group of pixels before and after the staining or transformation. This process from block 302 through block 328 can be repeated in some embodiments for different tissue samples to reduce error and/or to build a larger database.

In some embodiments, the computing system may detect that an input pixel or group of pixels associated with an identical or substantially similar waveform signature is inconsistently converted to a pixel or group of pixels associated with different waveform signatures in subsequent trials of data collection. In an embodiment, the process from block 302 through block 328 or selected block(s) thereof can be repeated until the discrepancy rate is lowered below a predetermined level. In another embodiment, the different conversion results are averaged out at block 332 and stored as the output waveform signature corresponding to the initial pixel or group of pixels associated with a particular waveform. Such conversion data is aggregated and saved in the computing system at block 334 as a virtual staining transform for a particular stain(s). In an embodiment, the method described above is repeated for different stains and/or other transformations or modification of the tissue sample. The individual virtual staining transforms thus developed can be combined to develop a single virtual staining transformation matrix containing all or some data related to the virtual transform of multiple stains and/or modifications.

In the embodiment illustrated in FIG. 3B, visible light is directed at the stained, physically, chemically or otherwise transformed tissue at block 336. Light that is transmitted, reflected, or otherwise not absorbed by the stained tissue sample is detected by at least one detection device at block 338. In some embodiments, more than one detection device can be utilized to reduce error in detection or to collect three-dimensional data. Based on the detected data, a final image is generated at block 340. In some embodiments, the computing system identifies each pixel or group of pixels that comprise the generated image according to color or other identifiable characteristics at block 342.

In another embodiment, the unstained tissue sample is not actually stained or tagged. Rather, the initial image itself is colored or is otherwise transformed according to a user's choice to generate a final image. For example, in embodiments where a virtual staining transform is being developed for imaging modalities including but not limited to X-ray, ultrasound, infrared, MRI, PET and/or CT, a user can selectively color or otherwise transform the initial image to a final image that is more helpful to understand or analyze.

With both the initial image(s) of an unstained sample and the final image(s) of an actually stained or otherwise transformed sample stored, the computing system of an embodiment can identify how an input pixel of the unstained sample associated with a particular waveform transformed to an output pixel after the staining or other transformation at block 344. To do so, in some embodiments, the computing system identifies and stores the waveform signatures associated with each pixel or group of pixels before the staining or transformation and the corresponding output pixel or color thereof after the staining or transformation. This process from block 302 through block 344 can be repeated in some embodiments for different tissue samples to reduce error and/or to build a larger database.

In some embodiments, the computing system may detect that an input pixel or group of pixels associated with an identical or substantially similar waveform signature is inconsistently converted to a pixel or group of pixels with different colors or other identifiable characteristics. In an embodiment, the process from block 302 through block 344 or selected block(s) thereof can be repeated until the discrepancy rate is lowered below a predetermined level. In another embodiment, the different conversion results are averaged out at block 346 and stored as the output pixel or group of pixels corresponding to the initial pixel or group of pixels associated with particular waveforms. Such conversion data is aggregated and saved in the computing system at block 348 as a virtual staining transform for a particular stain(s). In an embodiment, the method described above is repeated for different stains and/or other transformations or modification of the tissue sample. The individual virtual staining transforms thus developed can be combined to develop a single virtual staining transformation matrix containing all or some data related to the virtual transform of multiple stains and/or modifications.

Figure 4A:
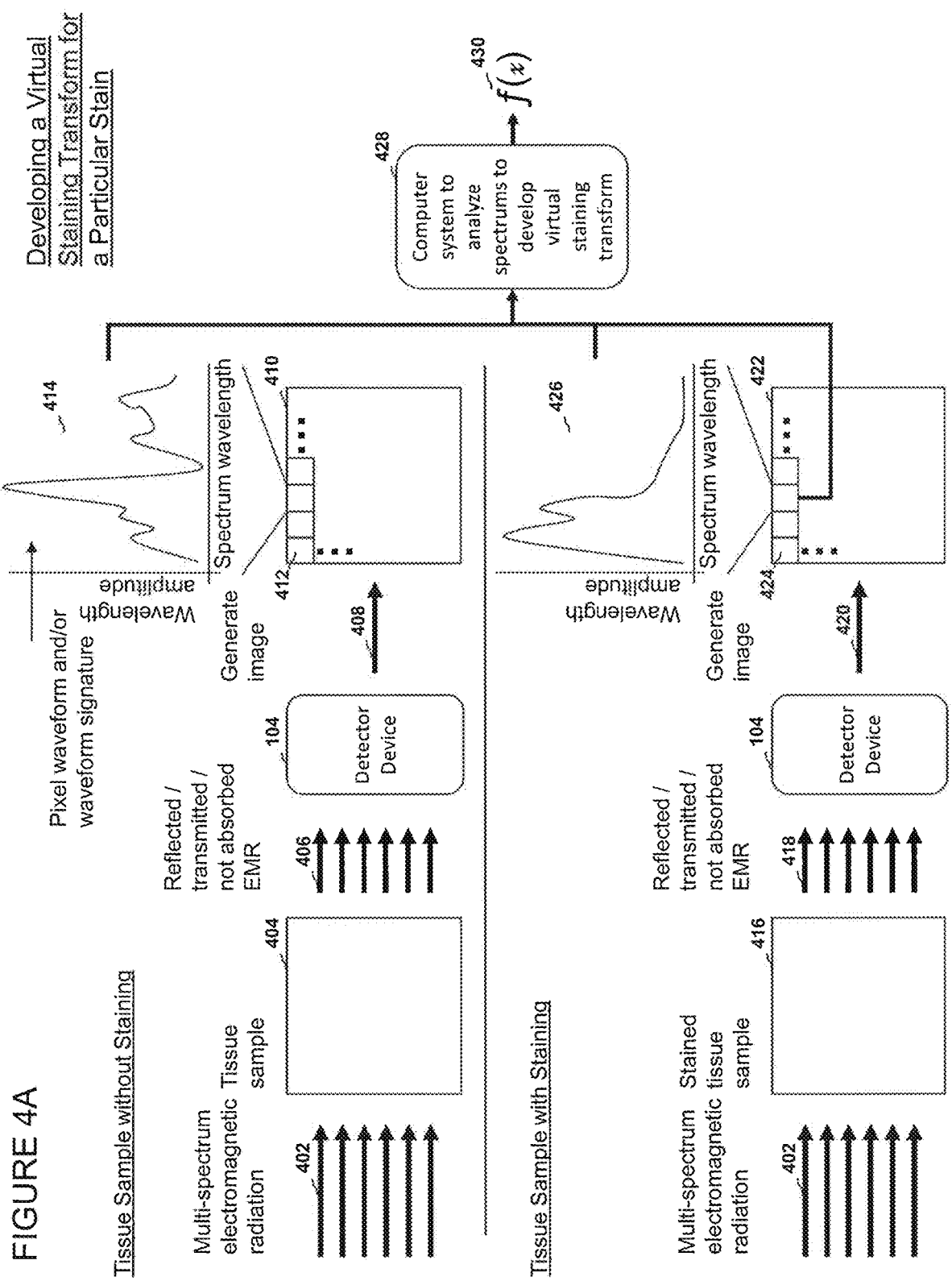
Figure 4B:
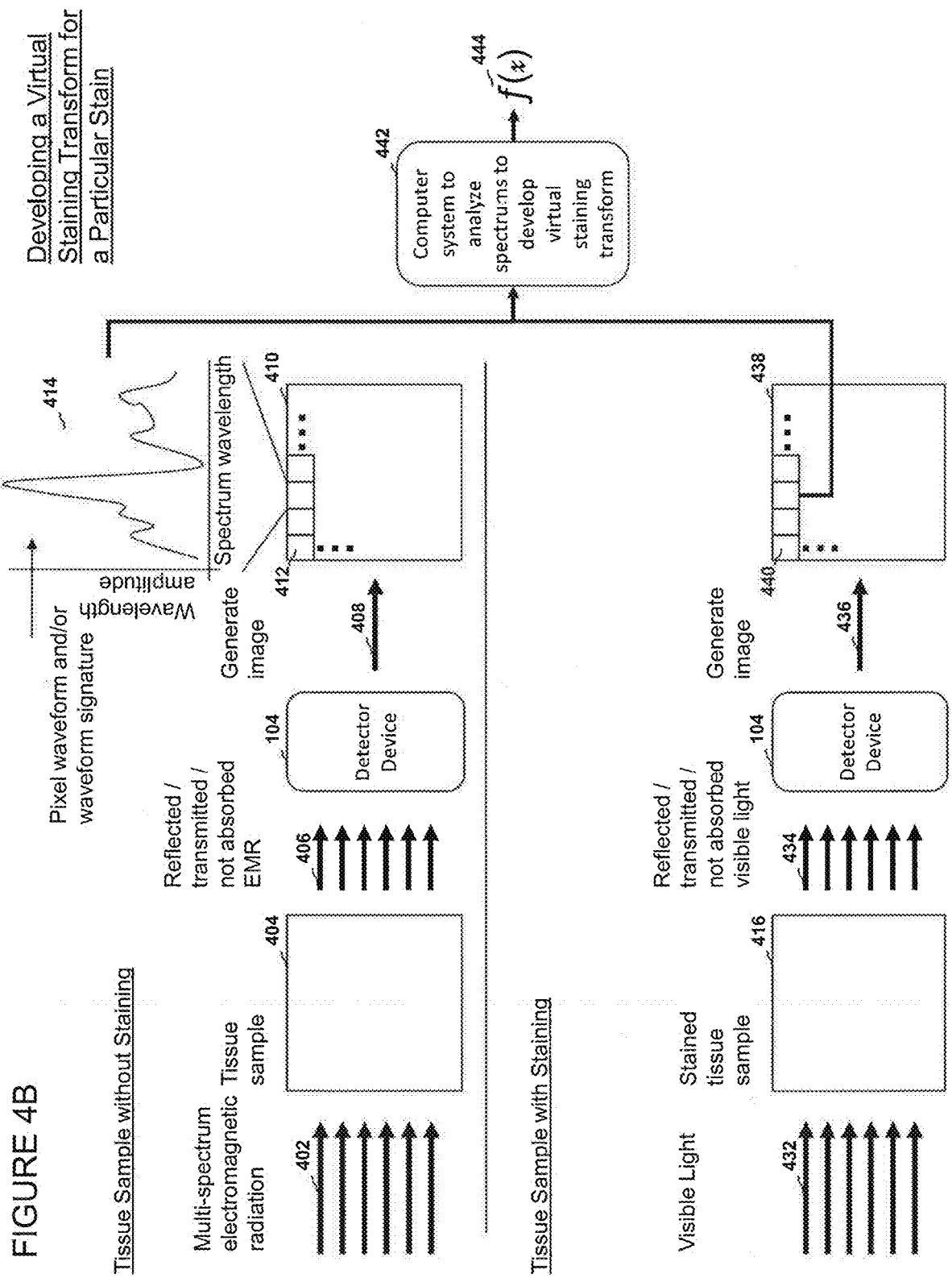

Preparation for Developing a Virtual Staining Transform for a Particular Stain, Tag, or Both FIGS. 4A-4F are block diagrams depicting overviews of embodiments of methods of collecting data and building virtual staining transforms. FIGS. 4A and 4B illustrate overviews of embodiments of methods of collecting data and building virtual staining transforms for particular stains. FIGS. 4C and 4D illustrate overviews of embodiments of methods of collecting data and building virtual staining transforms for particular stains when used together with particular tags. FIGS. 4E and 4F illustrate overviews of embodiments of methods of collecting data and building virtual staining transforms for particular tags when used alone without stains.

The top portions of FIGS. 4A-4F depict analyzing an image of a tissue sample before staining or other alteration. In an embodiment, multi-spectrum electromagnetic radiation 402 is directed at an unstained tissue sample 404. The unstained tissue sample 404 is not otherwise chemically altered from its natural state. In certain embodiments, some of the multi-spectrum electromagnetic radiation 402 is reflected, transmitted, or otherwise not absorbed 406 by the unstained tissue sample 404. Such multi-spectrum electromagnetic radiation 402 that is reflected, transmitted, or otherwise not absorbed 406 by the unstained tissue sample 404 is detected by a detector device 104. In certain embodiments, the detector device 104 transmits or otherwise sends the detected data 408 to an image generating system or device that generates an image 410 of the detected data. The generated image is made up of individual pixels or group of pixels 412 that each has a specific waveform and/or waveform signature 414 associated with the position of the pixel or group of pixels. Each waveform and/or waveform signature 414 can be analyzed by determining wavelength amplitudes for specific spectrum wavelengths. In some embodiments, a computer system is configured to graph the wavelength amplitude per spectrum wavelength for each pixel or group of pixels.

Developing a Virtual Staining Transform for a Particular Stain Used Alone

The bottom portions of FIGS. 4A and 4B depict analyzing images of tissue samples after staining with a particular stain or dye. In the depicted embodiments, the tissue sample without staining 404 is subsequently stained with a particular stain or dye. In the embodiment illustrated in FIG. 4A, multi-spectrum electromagnetic radiation 402 is directed at the stained tissue sample 416. In the embodiment illustrated in FIG. 4B, visible light 432 is directed at the stained tissue sample 416. In certain embodiments, some of the multi-spectrum electromagnetic radiation or visible light is reflected, transmitted, or otherwise not absorbed 418, 434 by the stained tissue sample 416. Such multi-spectrum electromagnetic radiation or visible light that is reflected, transmitted, or otherwise not absorbed 418, 434 by the stained tissue sample 416 is detected by a detector device 104. In certain embodiments, the detector device 104 transmits or otherwise sends the detected data 420,436 to an image generating system or device that generates an image 422, 438 of the detected data. The generated image is made up of individual pixels or group of pixels 424, 440.

In the embodiment illustrated in FIG. 4A, the computing system further analyzes waveforms 426 associated with each pixel or group of pixels 424 in the generated image 422. In certain embodiments, each waveform and/or waveform signature 426 can be analyzed by determining wavelength amplitudes for specific spectrum wavelengths. In some embodiments, a computer system is configured to graph the wavelength amplitude per spectrum wavelength for each waveform associated with each pixel or group of pixels. In some embodiments, a computer system analyzes the waveform and/or waveform signature of both the unstained tissue sample 404 and the stained tissue sample 416 at block 428. The detected waveforms of the unstained tissue sample 404 and the stained tissue sample 416 are identified and stored by the computer system to determine how a pixel or group of pixels associated with a specific waveform or waveform signature changed after the staining to a subsequent pixel or group of pixels associated with a waveform or waveform signature. Such information about how each pixel changed in waveform and/or waveform signature after the staining is stored and combined by the computer system in some embodiments to develop a virtual staining transform or transformation function 430.

In the embodiment illustrated in FIG. 4B, the computing system analyzes each pixel or group of pixels 440 in the generated image 438 according to color or some other identifiable characteristic at block 442. In some embodiments, the computer system determines how an input pixel or group of pixels 412 associated with a specific waveform 414 changed after staining to an output pixel or group of pixels 440 of a particular color or other identifiable characteristic. Such information is stored and combined by the computer system in some embodiments to develop a virtual staining transform or transformation function 444. Possible algorithms for developing virtual staining transforms comprise but are not limited to an extended Markov blanket approach, outlier detection based on Kullback-Leibler divergence, SVM with multi-classification algorithm, SVM-RFE and Markov blanket for high dimensional fluorescence data, or any other algorithm suitable for such purposes that is either currently known or will be developed in the future.

Developing a Virtual Staining Transform for a Particular Stain and Tag Used in Combination The bottom portions of FIGS. 4C and 4D depict analyzing images of tissue samples after staining with a particular stain or dye and attaching a particular tag. In the depicted embodiments, after analyzing the unstained tissue sample 404, the unstained and untagged tissue sample 404 is subsequently stained 416 and tagged 446. Tagging can be optional in some embodiments. A tag can comprise but is not limited to antibodies and/or aptamers with or without a label or fluorescent protein. In some embodiments, a tag can be configured to bind to specific receptors in the tissue sample. In certain embodiments, the presence of the protein or tag can cause electromagnetic radiation to be absorbed or reflected differently, which can help amplify and/or label the tissue sample for better detection and/or identification. For example, use of a tag or protein can be helpful in situations where different tissue, proteins, pixels or group of pixels of the sample to be imaged are associated with similar waveforms or absorption spectra.

In the embodiment illustrated in FIG. 4C, multi-spectrum electromagnetic radiation 402 is directed at the stained and tagged tissue sample 416, 446. In the embodiment illustrated in FIG. 4D, visible light 432 is directed at the stained and tagged tissue sample 416, 446. As described above, some of the multi-spectrum electromagnetic radiation or visible light is reflected, transmitted, or otherwise not absorbed 448, 462 by the stained and tagged tissue sample 416, 446. Such multi-spectrum electromagnetic radiation or visible light that is reflected, transmitted, or otherwise not absorbed 448, 462 by the stained and tagged tissue sample 416, 446 is detected by a detector device 104. In certain embodiments, the detector device 104 transmits or otherwise sends the detected data 450, 464 to an image generating system or device that generates an image 452, 466 of the detected data. The generated image is made up of individual pixels or group of pixels 454, 468.

In the embodiment illustrated in FIG. 4C, the computing system further analyzes waveforms 456 associated with each pixel or group of pixels 454 in the generated image 452. In certain embodiments, each waveform and/or waveform signature 456 can be analyzed by determining wavelength amplitudes for specific spectrum wavelengths. In some embodiments, a computer system is configured to graph the wavelength amplitude per spectrum wavelength for each waveform associated with each pixel or group of pixels. In some embodiments, a computer system analyzes the waveform and/or waveform signature of both the unstained and untagged tissue sample 404 and the stained and tagged tissue sample 416, 446 at block 458. The detected waveforms of the unstained and untagged tissue sample 404 and the stained and tagged tissue sample 416, 446 are identified and stored by the computer system to determine how a pixel or group of pixels associated with a specific waveform or waveform signature changed after the staining and/or tagging to a subsequent pixel or group of pixels associated with a waveform or waveform signature. Such information about how each pixel changed in waveform and/or waveform signature after the staining is stored and combined by the computer system in some embodiments to develop a virtual staining transform or transformation function 460.

In the embodiment illustrated in FIG. 4D, the computing system analyzes each pixel or group of pixels 468 in the generated image 466 according to color or some other identifiable characteristic at block 470. In some embodiments, the computer system determines how an input pixel or group of pixels 412 associated with a specific waveform 414 changed after staining to an output pixel or group of pixels 468 of a particular color or other identifiable characteristic. Such information is stored and combined by the computer system in some embodiments to develop a virtual staining transform or transformation function 472.

Possible algorithms for developing virtual staining transforms comprise but are not limited to an extended Markov blanket approach, outlier detection based on Kullback-Leibler divergence, SVM with multi-classification algorithm, SVM-RFE and Markov blanket for high dimensional fluorescence data, or any other algorithm suitable for such purposes that is either currently known or will be developed in the future.

Developing a Virtual Staining Transform for a Particular Tag Used Alone

The bottom portions of FIGS. 4E and 4F depict analyzing images of tissue samples after attaching a particular tag to the tissue sample. In the depicted embodiments, after analyzing the unstained tissue sample 404, the unstained and untagged tissue sample 404 is subsequently tagged with a particular tag 446. A tag can comprise but is not limited to antibodies and/or aptamers with or without a label or fluorescent protein. In some embodiments, a tag can be configured to bind to specific receptors in the tissue sample. In certain embodiments, the presence of the protein or tag can cause electromagnetic radiation to be absorbed or reflected differently, which can help amplify and/or label the tissue sample for better detection and/or identification. For example, use of a tag or protein can be helpful in situations where different tissue, proteins, pixels or group of pixels of the sample to be imaged are associated with similar waveforms or absorption spectra.

In the embodiment illustrated in FIG. 4E, multi-spectrum electromagnetic radiation 402 is directed at the tagged tissue sample 446. In the embodiment illustrated in FIG. 4F, visible light 432 is directed at the tagged tissue sample 446. As described above, some of the multi-spectrum electromagnetic radiation or visible light is reflected, transmitted, or otherwise not absorbed 474, 488 by the tagged tissue sample 446. Such multi-spectrum electromagnetic radiation or visible light that is reflected, transmitted, or otherwise not absorbed 474, 488 by the tagged tissue sample 446 is detected by a detector device 104. In certain embodiments, the detector device 104 transmits or otherwise sends the detected data 476, 490 to an image generating system or device that generates an image 478, 492 of the detected data. The generated image is made up of individual pixels or group of pixels 480, 494.

In the embodiment illustrated in FIG. 4E, the computing system further analyzes waveforms 482 associated with each pixel or group of pixels in the generated image. In certain embodiments, each waveform and/or waveform signature 482 can be analyzed by determining wavelength amplitudes for specific spectrum wavelengths. In some embodiments, a computer system is configured to graph the wavelength amplitude per spectrum wavelength for each waveform associated with each pixel or group of pixels. In some embodiments, a computer system analyzes the waveform and/or waveform signature of both the untagged tissue sample 404 and the tagged tissue sample 446 at block 484. The detected waveforms of the untagged tissue sample 404 and the tagged tissue sample 446 are identified and stored by the computer system to determine how a pixel or group of pixels associated with a specific waveform or waveform signature changed after the tagging to a subsequent pixel or group of pixels associated with a waveform or waveform signature. Such information about how each pixel changed in waveform and/or waveform signature after the tagging is stored and combined by the computer system in some embodiments to develop a virtual staining transform or transformation function 486.

In the embodiment illustrated in FIG. 4F, the computing system analyzes each pixel or group of pixels 494 in the generated image 492 according to color or some other identifiable characteristic at block 496. In some embodiments, the computer system determines how an input pixel or group of pixels 412 associated with a specific waveform 414 changed after staining to an output pixel or group of pixels 494 of a particular color or other identifiable characteristic. Such information is stored and combined by the computer system in some embodiments to develop a virtual staining transform or transformation function 498.

Possible algorithms for developing virtual staining transforms comprise but are not limited to an extended Markov blanket approach, outlier detection based on Kullback-Leibler divergence, SVM with multi-classification algorithm, SVM-RFE and Markov blanket for high dimensional fluorescence data, or any other algorithm suitable for such purposes that is either currently known or will be developed in the future.

Other Imaging Modalities

In some embodiments, a virtual staining transform can be developed and applied for other imaging modalities, including but not limited to X-ray, ultrasound, infrared, MIII, PET and/or CT, or any other imaging modality currently existing or to be developed in the future. In some of such embodiments, information associated with the tissue sample or other specimen to be observed is collected using one of such modalities and is transformed or converted according to a unique virtual staining transform mapping and is displayed to a user. FIGS. 5A-5E are block diagrams depicting overviews of embodiments of methods of virtually transforming a tissue sample that is imaged by various imaging techniques or modalities.

Figure 5A:
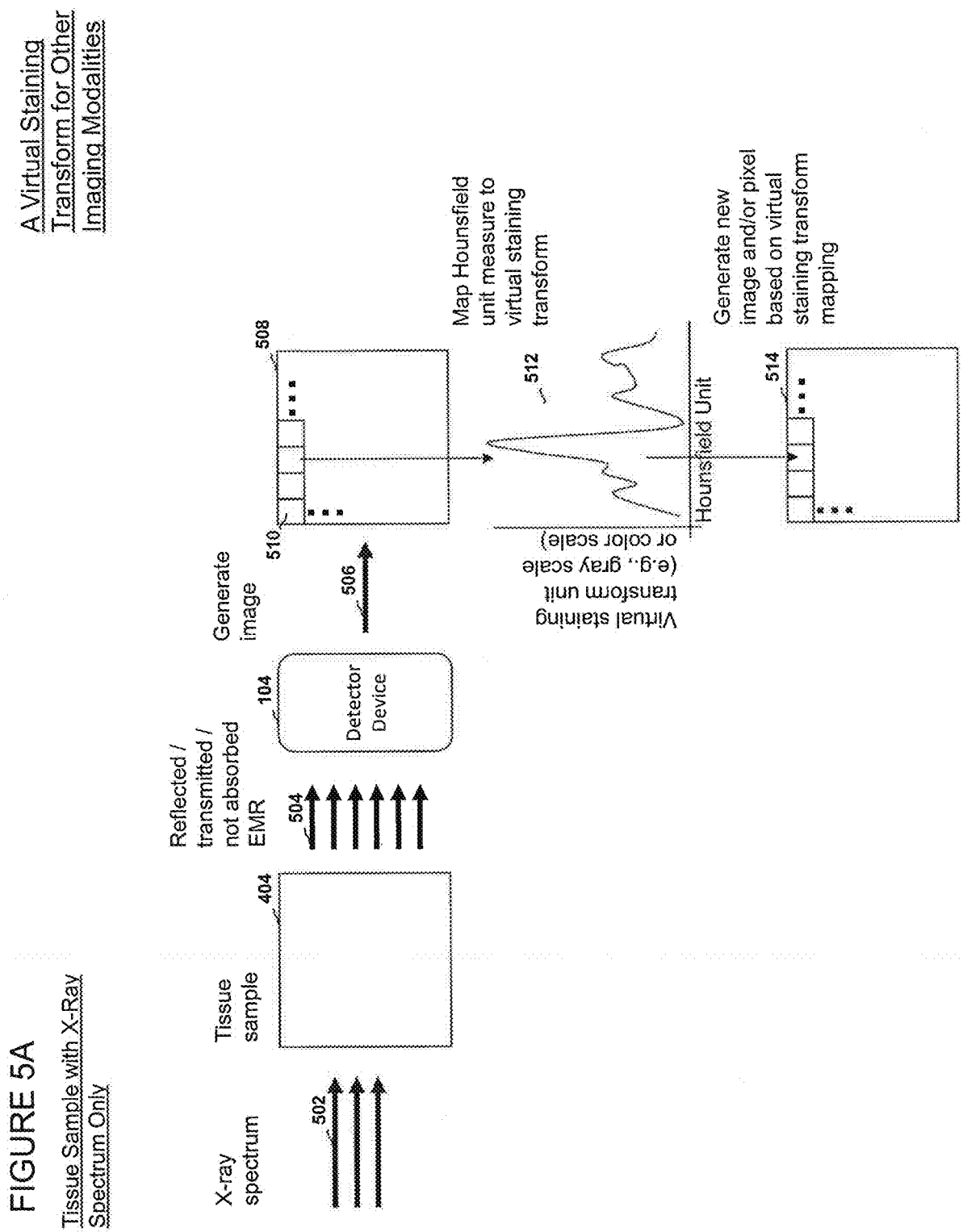
FIGS. 5A-5E are block diagrams depicting overviews of embodiments of methods of virtually staining a sample imaged by various imaging techniques or sources.

FIG. 5A illustrates an overview of one embodiment of a method of virtually transforming a tissue sample imaged under an X-ray spectrum. In an embodiment, X-ray spectrum 502 comprising a wavelength of about 0.01 nm to about 10 nm is directed at a tissue sample 404, which absorbs some of the X-ray and reflects, transmits, or otherwise does not absorb others. Such reflected, transmitted, or otherwise not absorbed X-ray 504 is detected by a detector device 104. This detected data 506 is transmitted or sent to an image generating system or device or computing system that is configured to generate an initial image 508 using the detected data. The generated image is made up of individual pixels or group of pixels 510. In some embodiments, each pixel or group of pixels 510 is associated with a Hounsfield unit measure or number. Each Hounsfield unit measure or number corresponds to the CT density.

In certain embodiments, a computing system converts or transforms the Hounsfield unit number associated with each pixel or group of pixels to an output unit or output unit waveform. In some embodiments, the computing system transforms the inputted Hounsfield unit number according to a pre-stored virtual staining transform 512, which contains transformation algorithms or data for transforming an inputted Hounsfield unit number to one or more output units or output unit waveforms. The output unit can be, for example, in gray scale or color in some embodiments. In certain embodiments, the computing system generates an output image 514 comprising pixels or group of pixels associated with the output unit or output unit waveforms according to the virtual staining transform.

Figure 5B:
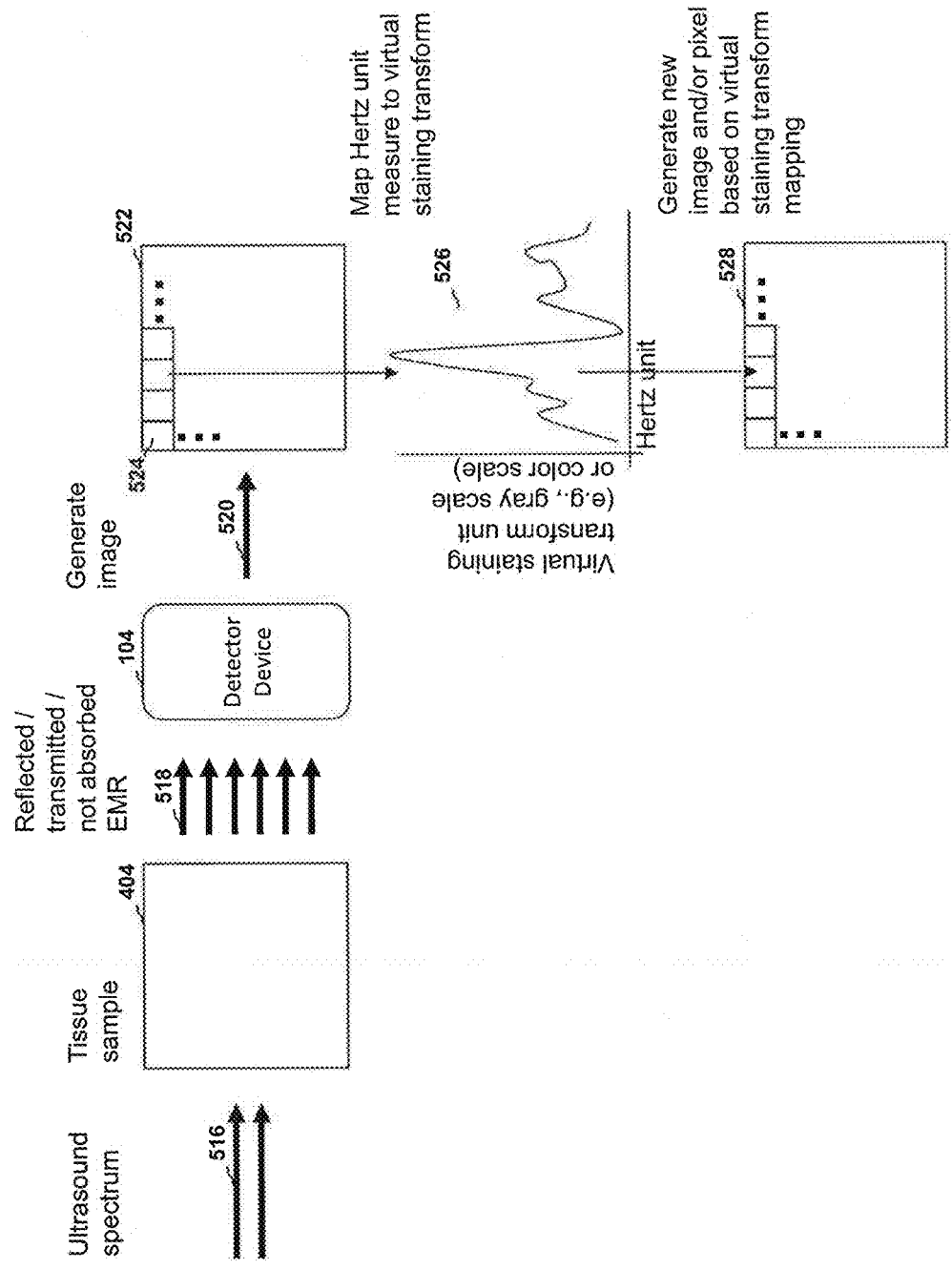

FIG. 5B illustrates an overview of one embodiment of a method of virtually transforming a tissue sample imaged under an ultrasound spectrum. In an embodiment, ultrasound spectrum 516 with a frequency range of above about 20 kHz is directed at a tissue sample 404, and some of the ultrasound is reflected, transmitted, or is otherwise not absorbed. Such reflected, transmitted, or otherwise not absorbed ultrasound 518 is detected by a detector device 104 in some embodiments. In certain embodiments, this detected data 520 is transmitted or sent to an image generating system or device or computing system that is configured to generate an initial image 522 using the detected data. In some embodiments, the generated image is made up of individual pixels or group of pixels 524. In certain embodiments, each pixel or group of pixels 524 is associated with a Hertz unit.

In certain embodiments, a computing system converts or transforms the Hertz unit associated with each pixel or group of pixels to an output unit or output unit waveform. In some embodiments, the computing system transforms the inputted Hertz unit according to a pre-stored virtual staining transform 526, which contains transformation algorithms or data for transforming an inputted Hertz unit to one or more output units or output unit waveforms. The output unit can be, for example, in gray scale or color in some embodiments. In certain embodiments, the computing system generates an output image 514 comprising pixels or group of pixels associated with the output unit or output unit waveforms according to the virtual staining transform.

Figure 5C:
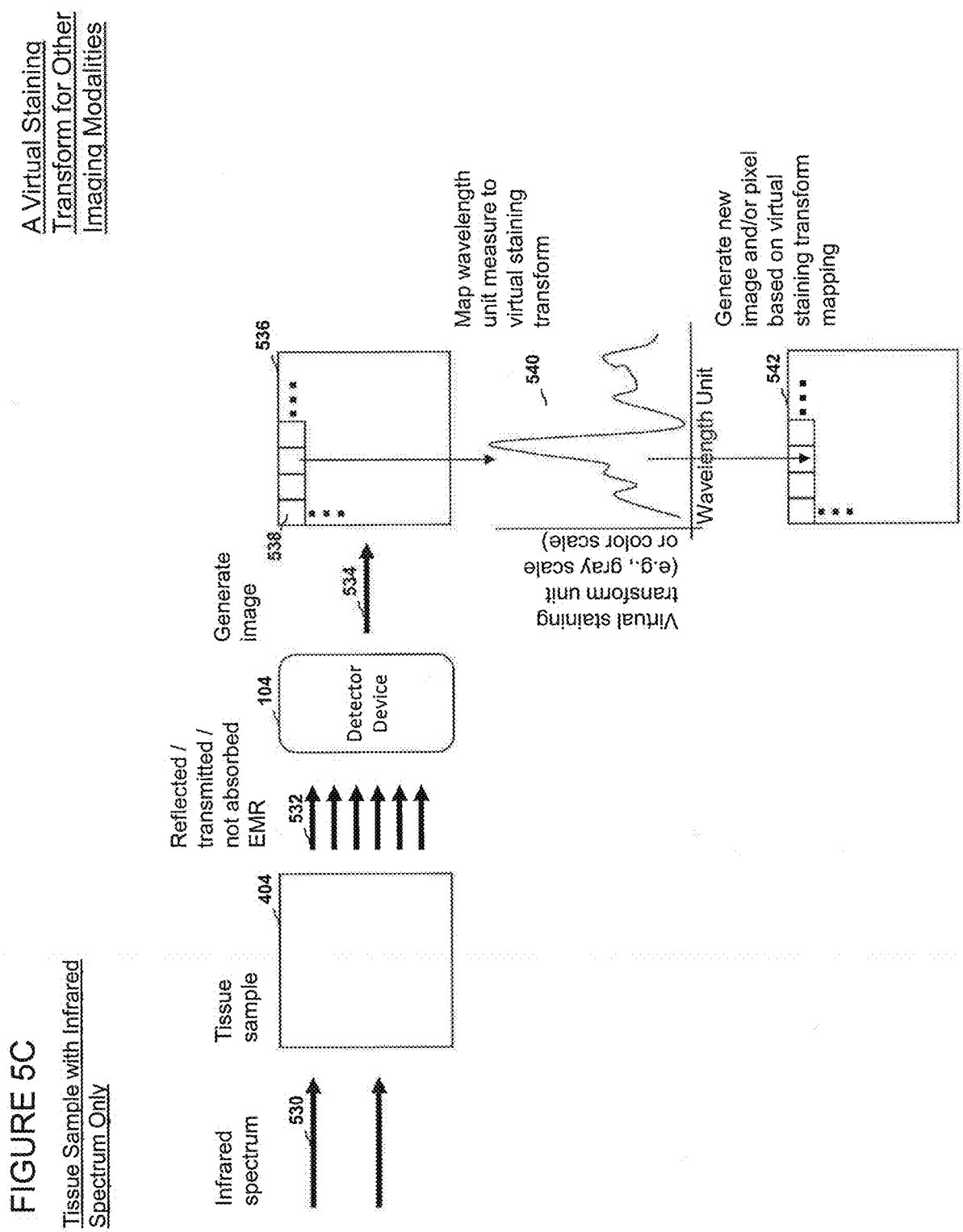

FIG. 5C illustrates an overview of one embodiment of a method of virtually transforming a tissue sample imaged under an infrared spectrum. In an embodiment, infrared spectrum 530 with a wavelength of greater than about 740 nm is directed at a tissue sample 404, which absorbs some of the infrared and reflects, transmits, or otherwise does not absorb others. Such reflected, transmitted, or otherwise not absorbed infrared 532 is detected by a detector device 104 in some embodiments. In certain embodiments, this detected data 534 is transmitted or sent to an image generating system or device or computing system that is configured to generate an initial image 536 using the detected data. In some embodiments, the generated image is made up of individual pixels or group of pixels 538. In certain embodiments, each pixel or group of pixels 538 is associated with a waveform signature. Each waveform signature can represent the detected wavelength and corresponding amplitudes that are detected by the detector at each position in the tissue sample.

In certain embodiments, a computing system converts or transforms the waveform associated with each pixel or group of pixels to an output unit or output unit waveform. In some embodiments, the computing system transforms the inputted waveform according to a pre-stored virtual staining transform 540, which contains transformation algorithms or data for transforming an inputted waveform to one or more output units or output unit waveforms. The output unit can be, for example, in gray scale or color in some embodiments. In certain embodiments, the computing system generates an output image 542 comprising pixels or group of pixels associated with the output unit or output unit waveforms according to the virtual staining transform.

Figure 5D:
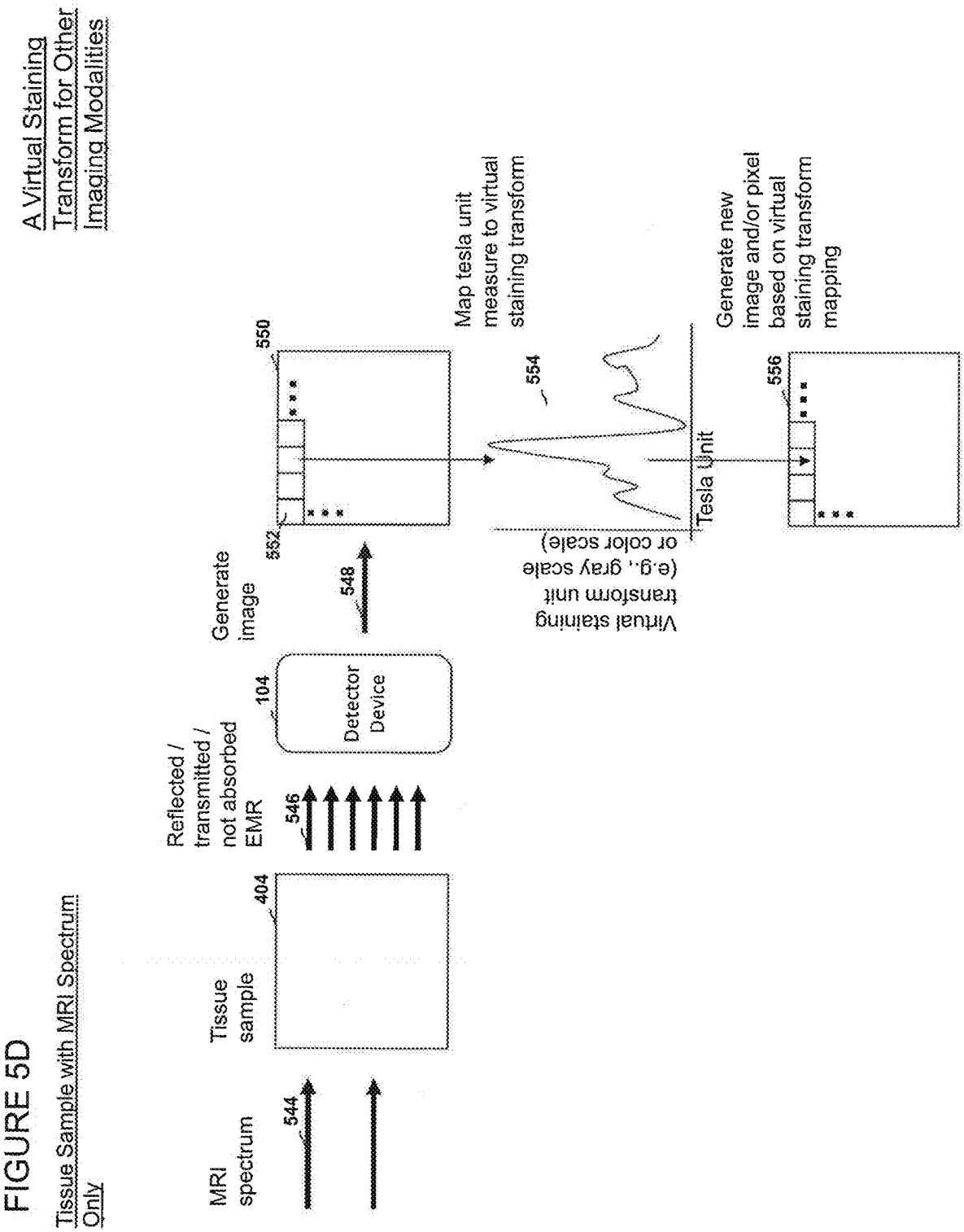

FIG. 5D illustrates an overview of one embodiment of a method of virtually transforming a tissue sample imaged under an MRI spectrum. In an embodiment, Mill spectrum 544 is directed at a tissue sample 404, which absorbs some of the Mill spectrum and reflects, transmits, or otherwise does not absorb others. Such reflected, transmitted, or otherwise not absorbed MM spectrum 546 is detected by a detector device 104 in some embodiments. In certain embodiments, this detected data 548 is transmitted or sent to an image generating system or device or computing system that is configured to generate an initial image 550 using the detected data. In some embodiments, the generated image is made up of individual pixels or group of pixels 552. In certain embodiments, each pixel or group of pixels 552 is associated with a Tesla unit.

In certain embodiments, a computing system converts or transforms the Tesla unit associated with each pixel or group of pixels to an output unit or output unit waveform. In some embodiments, the computing system transforms the inputted Tesla unit according to a pre-stored virtual staining transform 554, which contains transformation algorithms or data for transforming an inputted Tesla unit to one or more output units or output unit waveforms. The output unit can be, for example, in gray scale or color scale in some embodiments. In certain embodiments, the computing system generates an output image 556 comprising pixels or group of pixels associated with the output unit or output unit waveforms according to the virtual staining transform.

Figure 5E:
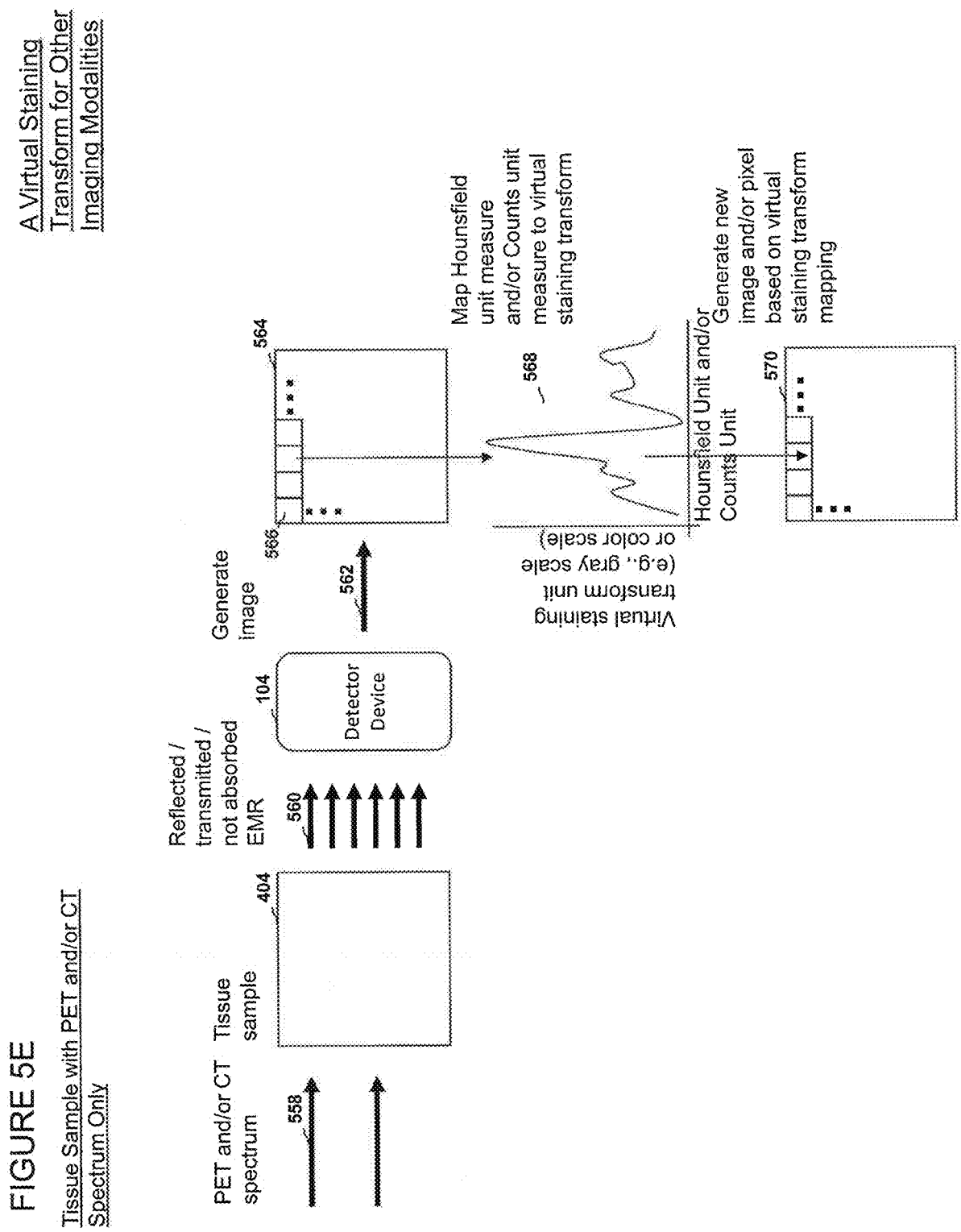

FIG. 5E illustrates an overview of one embodiment of a method of virtually transforming a tissue sample imaged under PET and/or CT spectrum. In an embodiment, PET and/or CT spectrum 558 is directed at a tissue sample 404, which absorbs some of the PET and/or CT spectrum and reflects, transmits, or otherwise does not absorb others. Such reflected, transmitted, or otherwise not absorbed PET and/or CT spectrum 560 is detected by a detector device 104 in some embodiments. In certain embodiments, this detected data 562 is transmitted or sent to an image generating system or device or computing system that is configured to generate an initial image 564 using the detected data. In some embodiments, the generated image is made up of individual pixels or group of pixels 566. In certain embodiments, each pixel or group of pixels 566 is associated with a Hounsfield and/or Counts unit.

In certain embodiments, a computing system converts or transforms the measured Hounsfield and/or Counts unit associated with of each pixel or group of pixels to an output unit or output unit waveform. In some embodiments, the computing system transforms the inputted Hounsfield and/or Counts unit according to a pre-stored virtual staining transform 568, which contains transformation algorithms or data for transforming an inputted Hounsfield and/or Counts unit to one or more an output units or output unit waveforms. The output unit can be, for example, in gray scale or color in some embodiments. In certain embodiments, the computing system generates an output image 570 using the comprising pixels or group of pixels associated with the output unit or output unit waveforms according to the virtual staining transform.

Figure 6B:
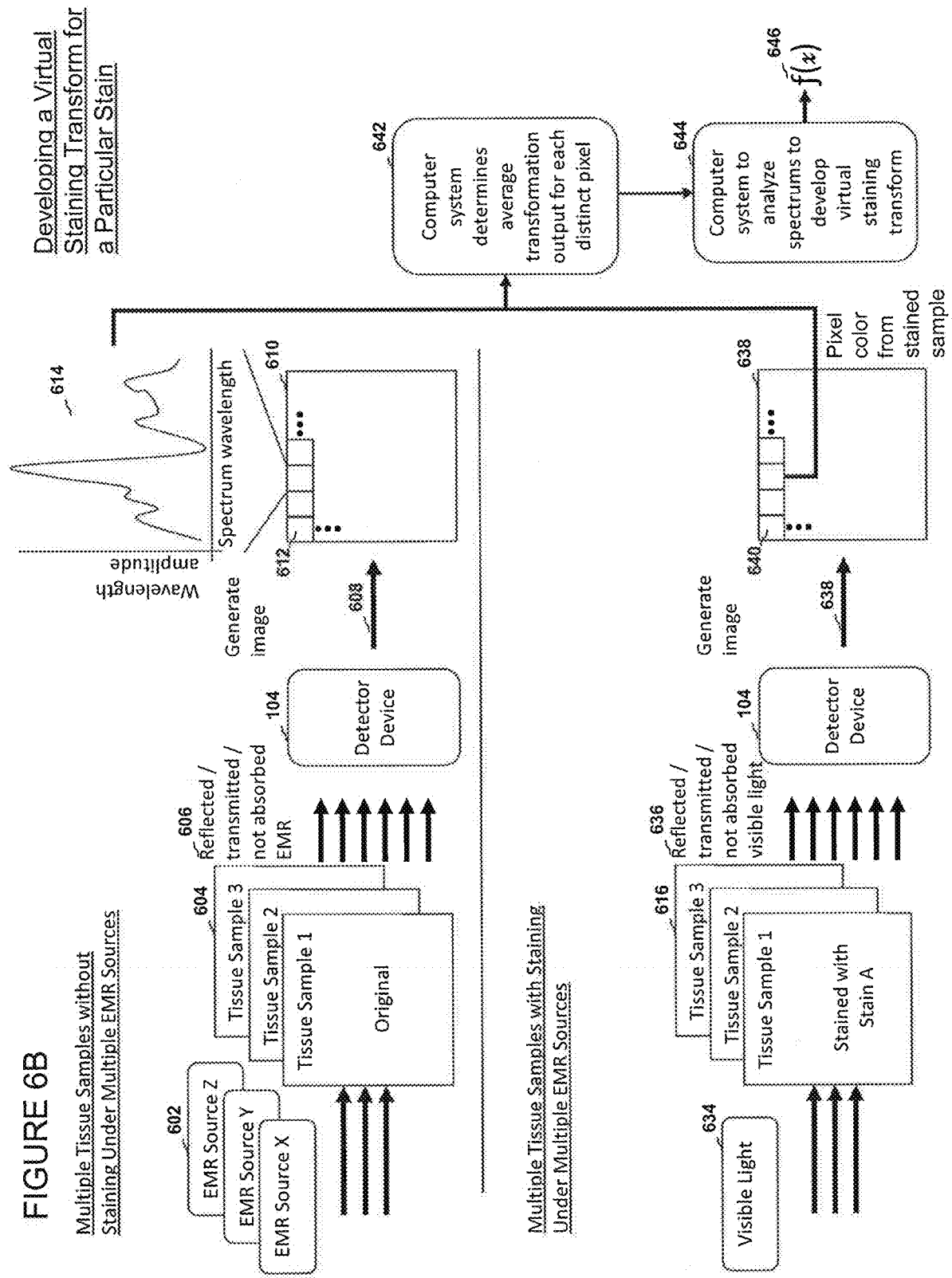

Developing a Virtual Staining Transform for a Particular Stain Under Multiple Electromagnetic Radiation Sources FIGS. 6A and 6B illustrate overviews of embodiments of methods of collecting data and building virtual staining transforms for a particular stain viewed under multiple electromagnetic radiation sources. The top portions of FIGS. 6A and 6B depict analyzing an image of a tissue sample without staining under a plurality of electromagnetic radiation sources. In an embodiment, a plurality of electromagnetic radiation sources 602 is directed at a plurality of unstained tissue samples 604. In some embodiments, each of the plurality of electromagnetic radiation sources 602 is individually directed at the plurality of unstained tissue samples 604 in turn. After directing a first electromagnetic radiation source 602 at the unstained tissue sample 604, a detector device 104 detects first electromagnetic radiation 602 that is reflected, transmitted, or otherwise not absorbed 606 by the unstained tissue samples 604 in a similar manner as described above. In certain embodiments, the detector device 104 transmits or otherwise sends the detected data 608 to an image generating system or device that generates an initial image 610 of the detected data. In some embodiments, a computer system is configured to analyze the waveform associated with each pixel 612 in a similar manner as described above. In the depicted embodiment, this process is repeated for the same tissue sample but under different electromagnetic radiation sources 602. This process can be repeated for different tissue samples as well.

In the depicted embodiments, the plurality of tissue samples without staining 604 are subsequently stained with a particular stain. In the embodiment illustrated in FIG. 6A, the plurality of electromagnetic radiation 602 is directed at the stained tissue samples 616. As described above, in some embodiments, each of the plurality of electromagnetic radiation sources 602 is individually directed at the plurality of unstained tissue samples 604 in turn. In the embodiment illustrated in FIG. 6B, visible light 634 is directed at the stained tissue samples 616. In some embodiments, electromagnetic radiation or visible light that is reflected, transmitted, or otherwise not absorbed 618, 636 by the stained tissue samples 616 is detected by a detector device 104. In certain embodiments, the detector device 104 transmits or otherwise sends the detected data 620, 638 to an image generating system or device that generates an image 622, 638 of the detected data. The generated image is made up of individual pixels or group of pixels 624, 640.

In the embodiment illustrated in FIG. 6A, the computing system further analyzes waveforms 626 associated with each pixel or group of pixels 624 in the generated image in a similar manner as described above. In some embodiments, these steps can be repeated for the same tissue sample but under different electromagnetic radiation sources 602. These steps can be repeated for different tissue samples as well. In some embodiments, a computer system analyzes the waveforms and/or waveform signatures associated with pixels of both the unstained plurality of tissue samples 604 and the stained plurality of tissue samples 616 at block 628. The detected waveforms associated with pixels of the unstained tissue samples 604 and the stained tissue samples 616 are identified and stored by the computer system to determine how a pixel or group of pixels associated with a specific waveform or waveform signature changed after the staining to a subsequent pixel or group of pixels associated with a waveform or waveform signature.

In the embodiment illustrated in FIG. 6B, the computing system analyzes each pixel or group of pixels 640 in the generated image 638 according to color or some other identifiable characteristic. In some embodiments, the computer system determines how an input pixel or group of pixels 612 associated with a specific waveform 614 changed after staining to an output pixel or group of pixels 640 of a particular color or other identifiable characteristic.

In some embodiments, the computer system may detect that inputted pixels or group of pixels associated with an identical or substantially identical input waveform are inconsistently transformed after staining to output pixels associated with different waveforms and/or different colors or other identifiable characteristics. When there are discrepancies in the detected data of how a single input waveform is transformed after staining with the same particular stain, the computer system in some embodiments determines an average output waveform and/or an average output color or other characteristic after the staining at block 628 or 642. In certain embodiments, the average output waveform and/or average output color or other characteristic associated with each pixel of the images of stained tissue samples is stored and combined by the computer system to develop a virtual staining transform or transformation function 632, 646. In certain embodiments, virtual staining transforms 632 for a particular stain can be developed in the general manner described above for each of the plurality of electromagnetic radiation sources 602 to obtain a more comprehensive virtual staining transform for that particular stain.

Possible algorithms for developing virtual staining transforms comprise but are not limited to an extended Markov blanket approach, outlier detection based on Kullback-Leibler divergence, SVM with multi-classification algorithm, SVM-RFE and Markov blanket for high dimensional fluorescence data, or any other algorithm suitable for such purposes that is either currently known or will be developed in the future.

Figure 7A:
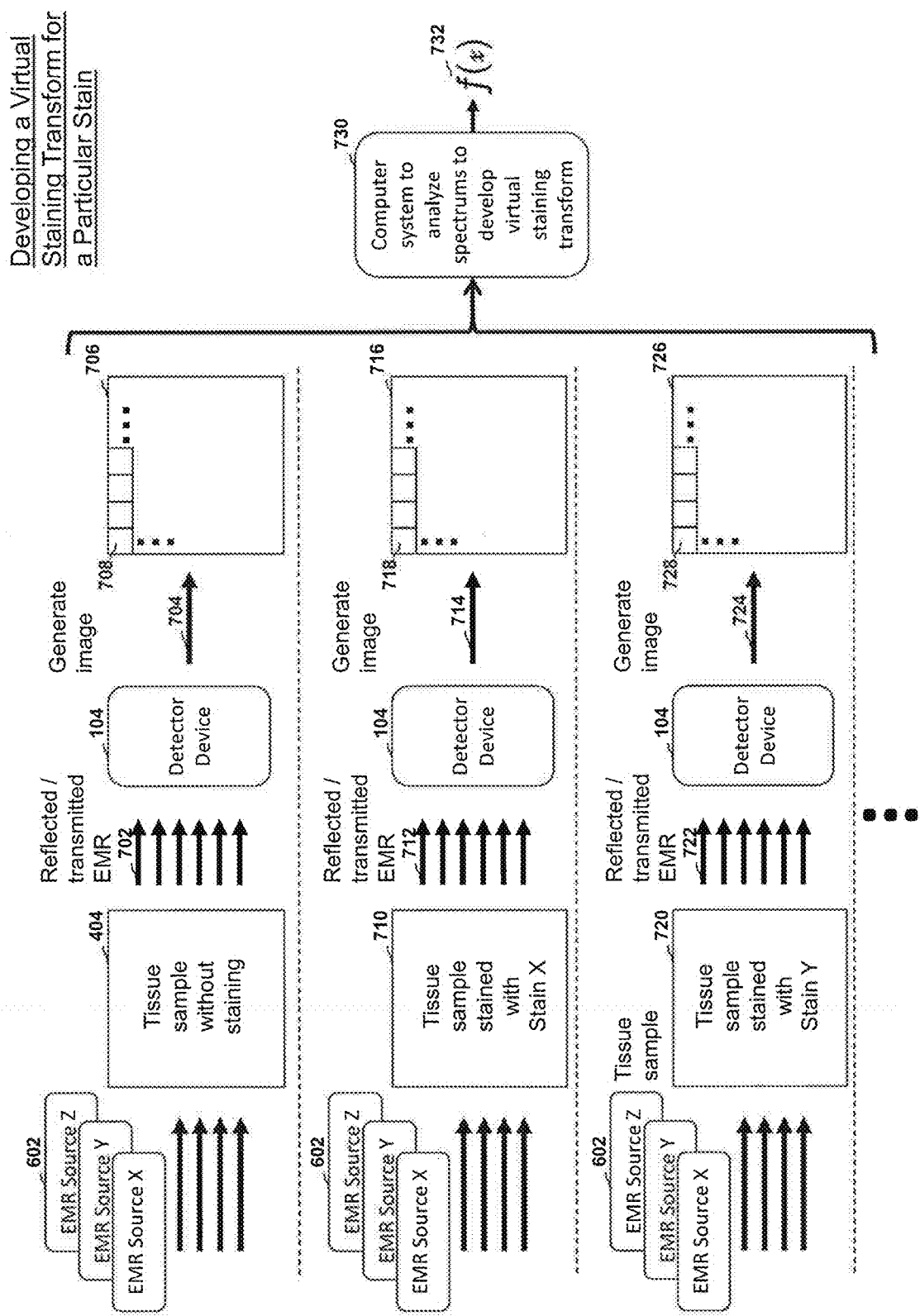
FIGS. 7A-7B are block diagrams depicting overviews of embodiments of methods of collecting data and building virtual staining transforms for multiple stains under multiple electromagnetic radiation sources.
Figure 7B:
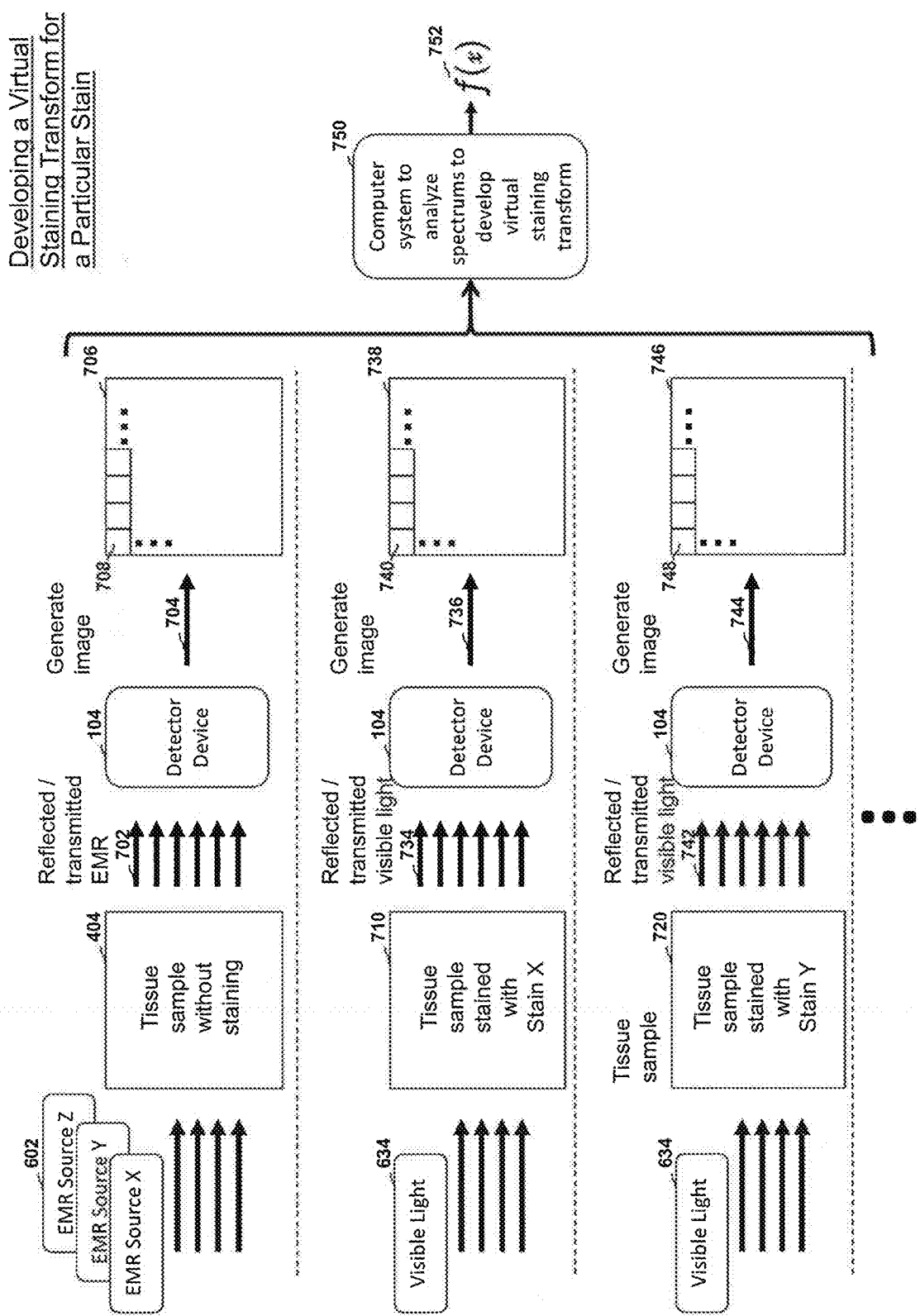

Developing a Virtual Staining Transform for Multiple Stains Under Multiple Electromagnetic Radiation Sources FIGS. 7A and 7B illustrate overviews of embodiments of methods of collecting data and building virtual staining transforms for multiple stains viewed under multiple electromagnetic radiation sources.

In the depicted embodiments, a plurality of electromagnetic radiation sources 602 are directed at an unstained tissue sample 404. In some embodiments, each of the plurality of electromagnetic radiation sources 602 is individually directed at the unstained tissue sample 404 in turn. After directing a first electromagnetic radiation source 602 at the unstained tissue sample 404, a detector device 104 detects electromagnetic radiation 602 that is reflected, transmitted, or otherwise not absorbed 702 by the unstained tissue sample 404 in a similar manner as described above. In certain embodiments, the detector device 104 transmits or otherwise sends the detected data 704 to an image generating system or device that generates an initial image 706 of the detected data. In some embodiments, a computer system is configured to analyze the waveform associated with each pixel 708 in a similar manner as described above. In the depicted embodiments, these steps can be repeated for the same tissue sample under different electromagnetic radiation sources 602.

In the depicted embodiments, the unstained tissue sample 404 or a section thereof is subsequently stained with Stain X 710. In the embodiment illustrated in FIG. 7A, the plurality of electromagnetic radiation 602 is directed at the tissue sample stained with Stain X 710. In the embodiment illustrated in FIG. 7B, visible light 634 is directed at the tissue sample stained with Stain X 710. Some of the electromagnetic radiation or visible light is reflected, transmitted, or otherwise not absorbed 712, 734 by the tissue sample stained with Stain X 710. In some embodiments, such electromagnetic radiation or visible light that is reflected, transmitted, or otherwise not absorbed 712, 734 by the tissue sample stained with Stain X 710 is detected by a detector device 104. In certain embodiments, the detector device 104 transmits or otherwise sends the detected data 714, 736 to an image generating system or device that generates an image 716, 738 of the detected data. The generated image is made up of individual pixels or group of pixels 718, 740. In the embodiment illustrated in FIG. 7A, each pixel or group of pixels can be associated with a particular waveform.

In some embodiments, the unstained tissue sample 404 or a section thereof is stained with Stain Y 720. In the embodiment illustrated in FIG. 7A, the plurality of electromagnetic radiation 602 is directed at the tissue sample stained with Stain Y 720. In the embodiment illustrated in FIG. 7B, visible light 634 is directed at the tissue sample stained with Stain Y 720. Some of the electromagnetic radiation or visible light is reflected, transmitted, or otherwise not absorbed 722, 742 by the tissue sample stained with Stain Y 720. Such electromagnetic radiation or visible light that is reflected, transmitted, or otherwise not absorbed 722, 742 by the tissue sample stained with Stain Y 722 is detected by a detector device 104. In certain embodiments, the detector device 104 transmits or otherwise sends the detected data 724, 744 to an image generating system or device that generates an image 726 of the detected data. The generated image is made up of individual pixels or group of pixels 728, 748. In the embodiment illustrated in FIG. 7A, each pixel or group of pixels can be associated with a particular waveform. In certain embodiments, the general method described above can be repeated for any number of different stains.

In the embodiment illustrated in FIG. 7A, a computer system further analyzes the waveforms and/or waveform signatures associated with each pixel or group of pixels of the unstained tissue sample 404, the tissue sample stained with Stain X 710, the tissue sample stained with Stain Y 720, and any other tissue samples stained with any other stain at block 730. The detected waveforms of the tissue samples stained with Stain X 710, Stain Y 720, and any other stain along with waveforms of the unstained tissue sample 404 are identified and stored by the computer system to determine how an unstained pixel or group of pixels associated with a specific waveform or waveform signature changed after each staining to a subsequent pixel associated with a waveform or waveform signature. Such information about how each waveform associated with each pixel changed in waveform and/or waveform signature after staining with each particular type of stain is stored and combined by the computer system in some embodiments to develop a virtual staining transform or transformation function 732.

In the embodiment illustrated in FIG. 7B, the computing system analyzes each pixel of images of the tissue sample stained with Stain X 710, the tissue sample stained with Stain Y 720, and any other stained tissue sample at block 750 according to color or some other identifiable characteristic. In some embodiments, the computer system determines how an input pixel or group of pixels 708 associated with a specific waveform changed after staining to an output pixel or group of pixels 740, 748 of a particular color or other identifiable characteristic. Such information is stored and combined by the computer system in some embodiments to develop a virtual staining transform or transformation function 752.

By employing the general methods of the embodiments described in connection to FIGS. 7A and 7B, comprehensive virtual staining transforms that comprise transformation data of more than one stain can be developed. Also, in certain embodiments, virtual staining transforms 732, 752 for each particular stain can be developed in the general manner described above for each of the plurality of electromagnetic radiation sources 602 to obtain an even more comprehensive virtual staining transform.

Possible algorithms for developing virtual staining transforms comprise but are not limited to an extended Markov blanket approach, outlier detection based on Kullback-Leibler divergence, SVM with multi-classification algorithm, SVM-RFE and Markov blanket for high dimensional fluorescence data, or any other algorithm suitable for such purposes that is either currently known or will be developed in the future.

Developing a Three-Dimensional Virtual Staining Transform for a Particular Stain FIGS. 8A and 8B illustrate overviews of embodiments of methods of collecting data and building a three-dimensional virtual staining transform for a particular stain viewed under multi-spectrum electromagnetic radiation. In some embodiments, a three-dimensional virtual staining transform can be developed in the same general manner as described below. In other embodiments, three dimensional virtual staining transforms for different electromagnetic radiation sources or for different stains can be developed by combining the methods described below with other embodiments described herein.

In the depicted embodiments, multi-spectrum electromagnetic radiation 402 is directed at an unstained tissue sample 404. In some embodiments, multi-spectrum electromagnetic radiation 402 is directed at the unstained tissue sample 404 from a plurality of directions surrounding the unstained tissue sample 404. In certain embodiments, the unstained tissue sample 404 is not otherwise chemically altered from its natural state. Some of the multi-spectrum electromagnetic radiation 402 is reflected, transmitted, or otherwise not absorbed 802 by the unstained tissue sample 404. Such electromagnetic radiation that is reflected, transmitted, or otherwise not absorbed 802 by the unstained tissue sample 404 is detected by a detector device 104. In some embodiments, the detector 104 is configured to capture video data of the electromagnetic radiation that is reflected, transmitted, or otherwise not absorbed 802 by the unstained tissue sample 404. In other embodiments, the detector or a plurality of detectors are positioned and configured to detect electromagnetic radiation that is reflected, transmitted, or otherwise not absorbed 802 by the unstained tissue sample 404 to allow generation of a three-dimensional image or space. In yet other embodiments, the detector or a plurality of detectors 104 are configured to capture three-dimensional video data of the electromagnetic radiation that is reflected, transmitted, or otherwise not absorbed 802 by the unstained tissue sample 404. For example, the detector can be configured to obtain two-dimensional images of the tissue sample on the xy plane at varying z depths by changing the focal depth of the detector. In some embodiments, the detector does not change its zoom but merely changes the focal depth to obtain xy images at different z depths. By changing the z depth, the detector generally gains or loses certain information, which can be processed according to a predetermined algorithm.

The detector device 104 transmits or otherwise sends the detected data 804 to an image generating system or device that generates an initial image or video 806 of the detected data. In certain embodiments, the initial image or video 806 is three-dimensional. The generated image or video is made up of individual pixels or group of pixels 808. Each pixel or group of pixels can be associated with a particular waveform 810. Each waveform signature can represent the detected wavelength and corresponding amplitudes that are detected by the detector at each position in the tissue sample. In some embodiments, a computer system is configured to graph the wavelength amplitude per spectrum wavelength for each waveform associated with each pixel or group of pixels.

In the depicted embodiments, the unstained tissue sample 404 or a section thereof is subsequently stained or tagged or is otherwise transformed 812. In the embodiment illustrated in FIG. 8A, multi-spectrum electromagnetic radiation 402 is directed at the stained tissue sample 812. In the embodiment illustrated in FIG. 8B, visible light 432 is directed at the stained tissue sample 812. In certain embodiments, some of the multi-spectrum electromagnetic radiation or visible light is reflected, transmitted, or otherwise not absorbed 814, 828 by the stained tissue sample 812. Such multi-spectrum electromagnetic radiation or visible light that is reflected, transmitted, or otherwise not absorbed 814, 828 by the stained tissue sample 814 is detected by a detector device 104. In some embodiments, the detector 104 is configured to capture video data of the electromagnetic radiation or visible light that is reflected, transmitted, or otherwise not absorbed 814, 828 by the stained tissue sample 812. In other embodiments, the detector or a plurality of detectors are positioned and configured to detect electromagnetic radiation or visible light that is reflected, transmitted, or otherwise not absorbed 814, 828 by the stained tissue sample 812 to allow generation of a three-dimensional image or space. In yet other embodiments, the detector or a plurality of detectors 104 are configured to capture three-dimensional video data of the electromagnetic radiation or visible light that is reflected, transmitted, or otherwise not absorbed 814, 828 by the stained tissue sample 812. For example, the detector can be configured to obtain two-dimensional xy images of the tissue sample at varying z depths by changing the focal depth of the detector.

The detector device 104 transmits or otherwise sends the detected data 816, 830 to an image generating system or device that generates an image or video 818, 832 of the detected data. In some embodiments, the image or video 818, 832 is three-dimensional. The generated image or video is made up of individual pixels or group of pixels 820, 834.

In the embodiment illustrated in FIG. 8A, each pixel or group of pixels can be associated with a particular waveform 810. Each waveform signature can represent the detected wavelength and corresponding amplitudes that are detected by the detector at each position in the tissue sample. In some embodiments, a computer system is configured to graph the wavelength amplitude per spectrum wavelength for each waveform associated with each pixel or group of pixels. Further, a computer system can be configured to analyze the waveforms and/or waveform signatures of the unstained tissue sample 404 and the stained tissue sample 812 at block 824. In some embodiments, the detected waveforms of the unstained tissue sample 404 and the stained tissue sample 812 are identified and stored by the computer system to determine how an unstained pixel or group of pixels associated with a specific waveform or waveform signature changed after staining to a subsequent waveform or waveform signature. Such information about how each pixel changed in waveform and/or waveform signature after staining with each particular type of stain is stored and combined by the computer system in some embodiments to develop a virtual staining transform or transformation function 826.

In the embodiment illustrated in FIG. 8B, the computing system can be configured to further analyze each pixel 834 of images of the stained tissue sample 812 according to color or some other identifiable characteristic. In some embodiments, the computer system determines how an input pixel or group of pixels 808 associated with a specific waveform changed after staining to an output pixel or group of pixels 834 of a particular color or other identifiable characteristic. Such information is stored and combined by the computer system in some embodiments to develop a virtual staining transform or transformation function 838.

In embodiments where three-dimensional data is detected by the detector device 104, the computer system can be configured to develop a virtual staining transform 826, 838 that comprises three-dimensional transformation data of pixels or groups of pixels after the staining. Similarly, in embodiments where video data is detected by the detector device 104, the computer system can be configured to develop a virtual staining transform 826, 838 that comprises video data or time-sensitive transformation data of pixels or groups of pixels after the staining.

Possible algorithms for developing virtual staining transforms comprise but are not limited to an extended Markov blanket approach, outlier detection based on Kullback-Leibler divergence, SVM with multi-classification algorithm, SVM-RFE and Markov blanket for high dimensional fluorescence data, or any other algorithm suitable for such purposes that is either currently known or will be developed in the future.

Figure 9A:
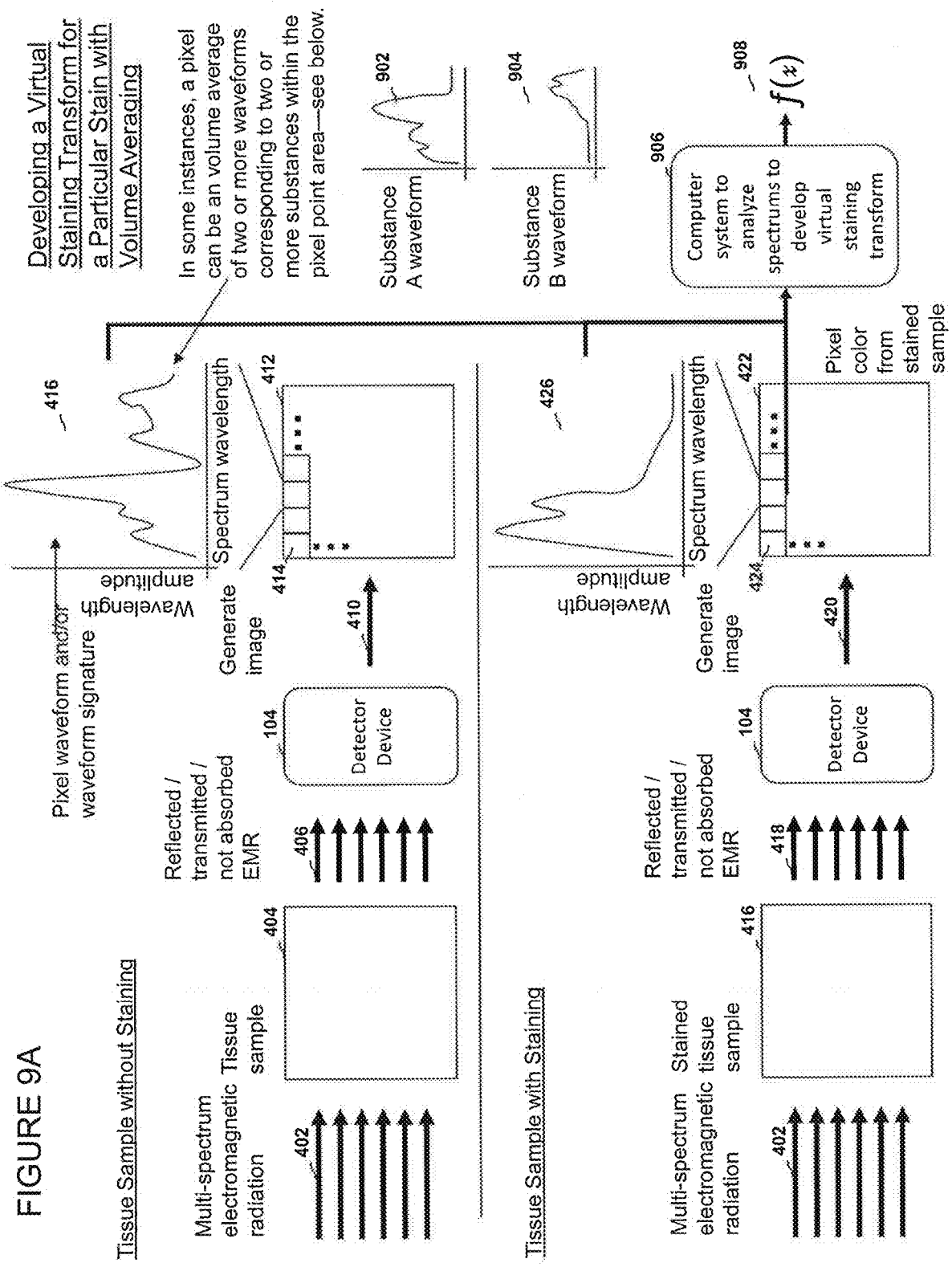

Developing a Virtual Staining Transform for a Particular Stain with Volume Averaging FIGS. 9A and 9B illustrate overviews of embodiments of methods of collecting data and building a virtual staining transform for a particular stain using volume averaging. The embodiments depicted in FIGS. 9A and 9B follow the same methods of developing a virtual staining transform as described above.

In some instances, the waveform and/or waveform signature 416 associated with a pixel or a group of pixels of an unstained tissue sample's image can be the product of more than one substances that exist within the pixel area on the tissue sample. In such cases, the detected waveform and/or waveform signature 416 is a combination or a volume average of two or more waveform signatures that correspond to each of the multiple substances within the pixel area. For example, the detected waveform 416 can be a combination of the waveform associated with Substance A 902 and the waveform associated with Substance B 904. In an embodiment, the computer system is configured to identify that a waveform associated with a particular pixel or group of pixels comprises one or more waveforms.

In the embodiment illustrated in FIG. 9A, the computer system is further configured to identify each of the one or more waveforms that comprise a single waveform associated with an input pixel and to match each of the one or more waveforms with one or more output waveforms according to a virtual staining transform. In other embodiments, the computer system is further configured to utilize volume averaging to determine a single output waveform for the input waveform that comprises one or more waveforms.

In the embodiment illustrated in FIG. 9B, the computer system is further configured to identify each of the one or more waveforms that comprise a single waveform associated with an input pixel and to match each of the one or more waveforms with one or more output pixels with particular colors and/or other identifiable characteristic according to a virtual staining transform. In other embodiments, the computer system is further configured to utilize volume averaging to determine a single output pixel with a particular color and/or other identifiable characteristic for the input waveform that comprises one or more waveforms.

Overview of Virtually Staining a Tissue Sample

Figure 10:
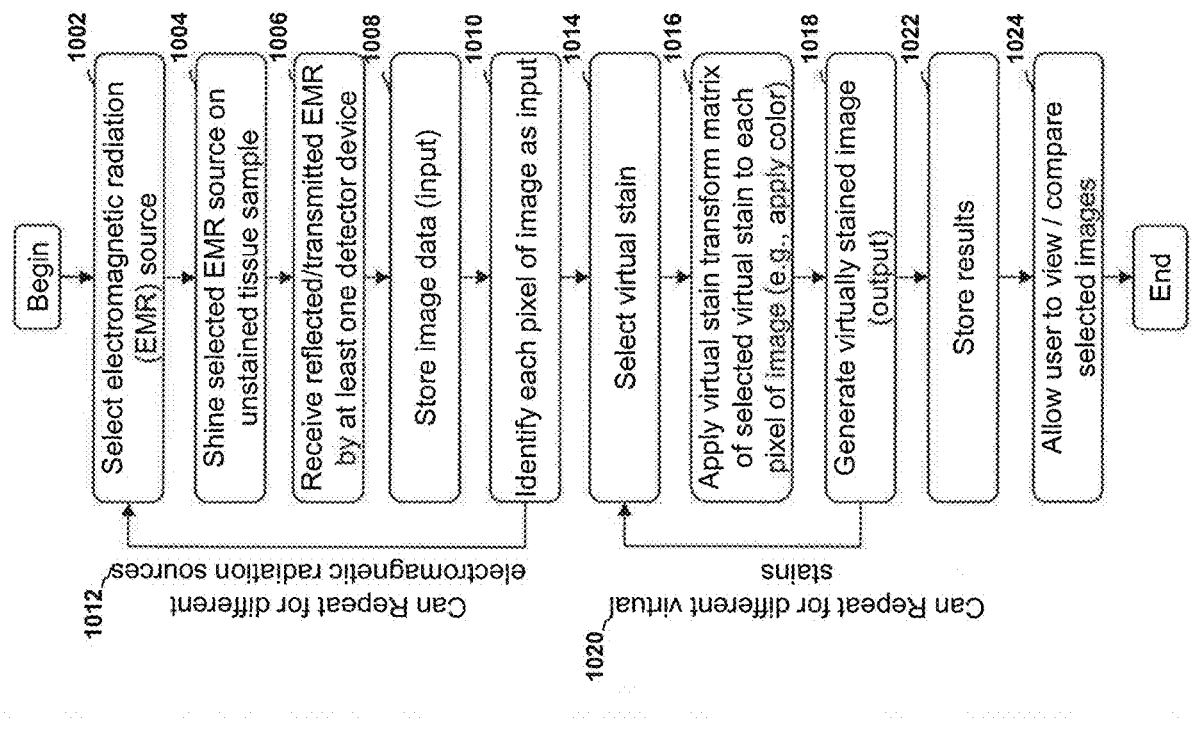
FIG. 10 is a block diagram depicting an overview of one embodiment of a method of virtually staining a tissue sample with different virtual stains and under different electromagnetic radiation sources using a virtual staining transform.

FIG. 10 illustrates an overview of one embodiment of a method of using a virtual staining transform to virtually stain a tissue sample with different virtual stains, tags, or other transforms and under different electromagnetic radiation sources. In some embodiments, the whole process or selected steps of FIG. 10 are repeated for different stains and/or for different electromagnetic radiation sources.

At block 1002, a particular electromagnetic radiation source is selected, which is subsequently directed at a an unstained tissue sample at block 1004. Electromagnetic radiation that is transmitted, reflected, or otherwise not absorbed by the sample is received by at least one detection device at block 1106. In certain embodiments, more than one detection device can be utilized to reduce error in detection or to collect three-dimensional data.

Based on the detected data, an initial image is generated and stored as input at block 1108. A computing system analyzes this initial image at block 1010. The initial image comprises pixels or group of pixels. In some embodiments, each pixel or group of pixels is associated with a particular waveform 810. Each waveform signature can represent the detected wavelength and corresponding amplitudes that are detected by the detector at each position in the tissue sample. In certain embodiments, the computing system is configured to determine the chemical properties of each pixel or group of pixels based on the detected waveform associated with the pixel or group of pixels. In certain embodiments, the steps of blocks 1002 through 1010 can be repeated to store initial images and waveforms associated with each pixel or group of pixels of images of unstained tissue samples under different types of electromagnetic radiation sources as depicted by 1012.

In the depicted embodiment, a user selects a virtual stain, tag, or other transform to apply to the tissue sample at block 1014. In some embodiments, the computer system applies the appropriate virtual stain transform corresponding to the selected transformation, stain, or tag to each pixel or group of pixels of the initial image at block 1016. In certain embodiments, each pixel associated with an identified waveform is transformed to an output pixel according to the virtual stain transform. For example, the system can be configured to match or to substantially match a pixel associated with an identified waveform to one or more output pixels associated with particular waveforms pre-stored in the database. In other embodiments, each pixel associated with an identified waveform is transformed to an output pixel of a particular color or other identifiable characteristic according to the virtual stain transform. For example, the system can be configured to match or to substantially match a pixel associated with an identified waveform to one or more output pixels with particular colors.

If there is a match or a substantial match, the system can be configured to identify an output pixel. In some embodiments, the matching comprises categorizing a detected waveform according to particular compartments, ranges, and/or bands of waveforms that are pre-determined and stored in the database. For example, if a detected waveform is within a particular compartment, range, and/or band of pre-stored waveforms, the system can be configured to match the detected waveform with that pre-stored compartment, range, and/or band and identify an output pixel associated with the compartment, range, and/or band. The system can be further configured to map the output pixel(s) to the virtually stained image. In certain embodiments, output pixels are in color or grayscale.

The computer system generates a virtually stained image at block 1018. In certain embodiments, the steps of blocks 1014 through 1018 can be repeated to generate more than one virtually stained image by applying different stains, tags, or other transforms to the initial image. The results can be stored in the computer system at block 1022. In some embodiments, the user can view and/or compare selected images among the initial image and any generated images at block 1024.

Generation of Multiple Output Pixels Per Input Pixel

In some embodiments, the virtual staining systems and methods described herein produce one output pixel for each input pixel. In other embodiments, the virtual staining systems and methods described herein produce more than one output pixel for each input pixel. FIG. 11 illustrates an overview of some embodiments of methods of virtually staining that generate more than one output pixel for each input pixel.

In an embodiment, the virtual staining process comprises determining a single output pixel for each input pixel according to the appropriate virtual staining transform. For example, if the virtual staining transform of a particular virtual stain, tag, or other transformation transforms an input pixel A 1104 associated with an input waveform X to an output pixel B 1108 associated with an output waveform Y, each instance of input pixel A 1104 in the initial image is mapped as a single output pixel B 1108 in the virtually stained image 1106. In other words, the virtual staining process maps a single input pixel to a single output pixel according to the pre-stored virtual staining transform that corresponds to the selected virtual stain, tag, or other transformation. In some embodiments, an output pixel associated with an input pixel 1104 located on a two-dimensional initial image 1102 is mapped to a two-dimensional virtually stained image 1106 at the same xy position. In other embodiments, an output pixel associated with an input pixel located on a three-dimensional initial image or space is mapped to a three-dimensional virtually stained image or space at the same xyz position. In certain embodiments, an output pixel associated with an input pixel located on a three-dimensional initial image or space is mapped to a two-dimensional virtually stained image at the same xy position. In other embodiments, an output pixel associated with an input pixel located on a two-dimensional initial image is mapped to a three-dimensional virtually stained image or space at the same xy position and an appropriate z position.

In other embodiments, the system is configured to determine and/or generate more than one pixel per each input pixel. In some embodiments, one input pixel 1104 can be mapped to four output pixels 1114 to generate an output image with twice the number of pixels in length and in width. In certain embodiments, one input pixel 1104 can be mapped to nine output pixels 1120 to generate an output image with three times the number of pixels in length and in width. In other embodiments, one input pixel 1104 can be mapped to multiple output pixels 1126 that are stacked or layered on top of each other. The additional pixels 1114, 1120, 1126 can be smaller, larger, or of the same size as the single output pixel 1108 associated with the input pixel 1104.

In some embodiments, the additional output pixels are obtained by further analyzing the waveform associated with the input pixel. For example, in some embodiments, an input pixel can be associated with two or more waveforms pre-stored in the database. A first portion of a waveform associated with an input pixel can correspond to a first pre-stored waveform, and a second portion of the waveform associated with the input pixel can correspond to a second pre-stored waveform. Further, a virtual staining transform can comprise different output pixels, waveforms, and/or colors for each of these pre-stored waveforms. In embodiments where only one output pixel is generated per each input pixel, the plurality of output pixels for pre-stored waveforms that are all associated with a single input pixel can be averaged or combined according to some predetermined algorithm to generate a single output pixel. However, in embodiments where more than one output pixel is generated per each input pixel, all or a subgroup of the plurality of output pixels for the pre-stored waveforms that are all associated with the single input pixel can be mapped. In certain embodiments, the additional pixels comprise output pixels obtained from directing different electromagnetic radiation, applying different stains, or information obtained by imaging under different modalities, such as X-ray, ultrasound, infrared, Mill, PET and/or CT for example. In other embodiments, the additional pixels comprise output pixels obtained from interpolating output pixels obtained from a virtual staining transform.

In some embodiments, these additional pixels are mapped in a random or arbitrary order or position. In certain embodiments, the additional pixels are mapped onto locations on the virtually stained image 1110, 1116, 1122 in order of intensity or concentration. In other embodiments, the additional pixels are mapped onto locations on the virtually stained image 1110, 1115, 1122 according to some other pre-determined order or algorithm.

In some embodiments, the additional pixels are displayed natively. For example, if the system is configured to generate four output pixels per input pixel, the system in some embodiments can immediately display a virtually stained image comprising all or a subgroup of the four output pixels per input pixel. In other embodiments, the additional pixels are not initially displayed but can be displayed upon receiving further instructions from the user. For example, the system can first display a single output pixel 1112 per input pixel 1104. However, once a user double clicks on a single output pixel 1112, zooms-in on the virtually stained image, or performs some other pre-determined instruction, the system can display all or a subgroup of the four output pixels 1114 per input pixel. A system configured to generate nine output pixels 1120 per input pixel 1104 can also either natively display all or a subgroup of nine pixels 1120. Alternatively, the system can display all or a subgroup of the nine pixels 1120 upon receiving further instructions from a user.

In an embodiment, the additional pixels are not mapped or placed next to each other but are stacked or layered on top of each other. In some embodiments, the system can be configured to initially display only one output pixel 1124 per input pixel 1104. However, additional output pixels 1126 corresponding to the same input pixel 1104 are in fact determined by the system and stored in a "stack" in the background. Upon receiving further instructions from a user, the system can be configured to "toggle" between different output pixels 1126 and display the different output pixels 1126. In other embodiments, the system can be configured to overlay and display output pixels associated with more than one imaging modality, stain, tag, or other transform together such that a plurality of output pixels can be viewed as a single output pixel.

If both the initial image or space and the virtually stained image or space are three-dimensional, the virtually stained image or space can be twice the size or more in length, width, and depth as the initial image or space. In some embodiments, one input pixel can correspond to eight output pixels to generate an output image with twice the number of pixels in length, width, and depth. In other embodiments, one input pixel can correspond to 27 output pixels to generate an output image with three times the number of pixels in length, width, and depth. The additional pixels can comprise any of those described above in relation to two-dimensional images. Further, the manner in which these additional pixels are displayed can further follow any of those described above.

Multiple Virtual Stains Applied to a Single Tissue Sample

As described above, more than one virtual stain, tag, or other transform can be applied to a single tissue sample according to some embodiments. FIGS. 12A and 12B illustrate embodiments of methods of virtually staining a single tissue sample with multiple virtual stains, tags, or other transforms.

The same general method of analyzing a tissue sample by pixel or group of pixels under an electromagnetic radiation source as described above applies to the embodiments illustrated in FIGS. 12A and 12B. After each pixel or group of pixels of the initial image is analyzed and associated waveforms and/or waveform signatures 416 are determined, a computer system in some embodiments applies multiple virtual stains to the input waveforms detected from an initial image of the tissue sample to produce output images that are virtually stained, tagged, or otherwise transformed at block 1202. For example, the computer system can generate images of the tissue sample virtually stained with Stain A 1204, Stain B 1210, Stain C 1216, Stain D 1222, and/or any other stain as selected by the user and available in the database.

Each generated image 1204, 1210, 1216, 1222 corresponding to each virtual stain, tag, or other transform comprises pixels or groups of pixels 1206, 1212, 1218, 1224. In the depicted embodiments, each pixel or group of pixels is associated with a waveform 1208, 1214, 1220, 1226 (as illustrated in FIG. 12A) or a particular color or other identifiable characteristic. The computer system maps each input pixel associated with a particular waveform 416 to an output pixel according to the selected particular stain, tag, or other transform. For example, if a user instructed the computer system to virtually stain the tissue sample with Stain A, the computer system maps an input pixel of the initial image 416 associated with a particular waveform to an output pixel 1206 according to a virtual transform for Stain A that is stored in the computer database. If the user instructed the computer system to virtually stain the tissue sample with Stain B, the computer system maps the same input pixel associated with the particular waveform to an output pixel 1212 according to a virtual transform for Stain B that is stored in the computer database. The same process can be applied to any number of virtual stains as selected by the user.

Side-By-Side Display of a Single Tissue Sample Virtually Stained with Multiple Stains In some embodiments, images of a tissue sample virtually stained with multiple virtual stains can be viewed side-by-side on a display. FIG. 12C illustrates one embodiment of a screen view of a single tissue sample virtually stained by multiple virtual stains. It is understood that this is not the only embodiment of such screen view and that other designs or configurations are possible.

In the embodiment as illustrated in FIG. 12C, the initial image of the unstained tissue sample 1228 is displayed side-by-side with a generated image of the tissue sample virtually stained with Stain A 1232 and a generated image of the tissue sample virtually stained with Stain B 1236. Further, close-up views of a single area within these images 1230, 1234, 1238 can be compared side-by-side in some embodiments.

Examples of Virtual Staining

FIG. 13 illustrates an example of virtually staining as conducted by an embodiment. FIG. 13A depicts an example of a digitally or virtually stained result of a slide using an embodiment disclosed herein. FIG. 13B is an image of the same slide when actually stained with H&E stain. As seen from comparing FIGS. 13A and 13B, the virtually or digitally stained result appears substantially similar to the actually stained slide.

The four images of FIG. 13C each correspond to which pixels of the original image reflect a particular color, for example red, green, blue, and yellow. The four graphs of FIG. 13D represent the actual underlying data of each pixel of FIG. 13C. Each of these four graphs represents the intensity of certain wavelengths of each pixel as detected by the detection device. The data of a single pixel corresponds to a single line or single waveform in FIG. 13D.

Figure 14:
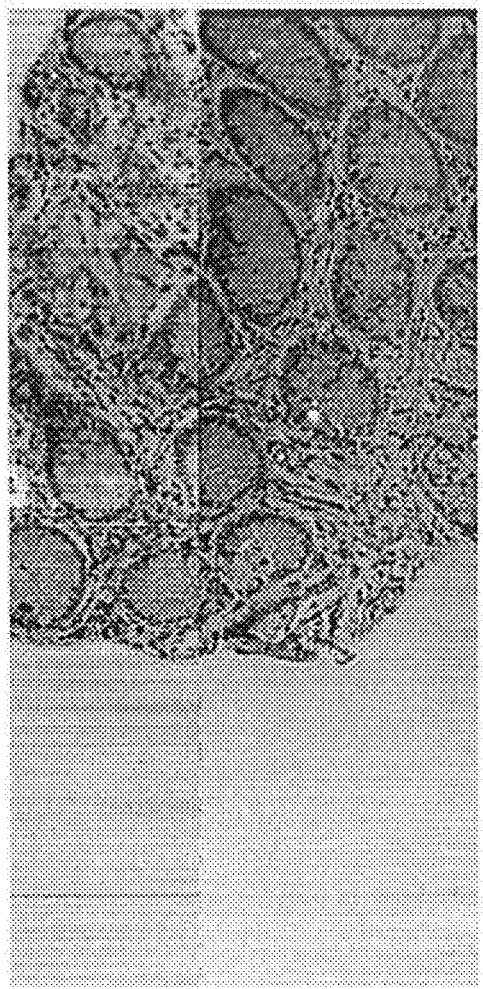
FIG. 14 depicts an example of a virtually stained image.

FIG. 14 illustrates another example of a virtually or digitally stained tissue sample. In the depicted embodiment, each detected pixel from the initial detection is assigned a color according to the detected waveform associated with each pixel. Accordingly, the output as illustrated in FIG. 14 is a pseudo-colored version of an unstained slide.

Hyperspectral Imaging and Identifying Species

Current methods of identifying microorganisms generally involve manually analyzing a single plate on which the microorganism specimen is located by mass spectroscopy. A person or automated machine generally carries out such methods by shining infrared light at each plate of microorganisms to determine whether there is growth or not. Further, human interaction is generally required to determine the identity of the microorganism species in such methods.

However, in an embodiment, the methods of virtual staining and hyperspectral imaging described above can be used to automatically identify the species of a biological sample or microorganism. In many instances, a microorganism will have one type of waveform signature under hyperspectral imaging. Waveforms of different microorganisms may have one or more peaks, where each peak correlates to some protein of the microorganism. The identity of such protein, however, is not necessary to determine the identity of the microorganism, because the whole waveform itself can be used to identify the microorganism using the hyperspectral imaging methods described above.

In an embodiment, the system has a pre-stored database of waveform signatures associated with different microorganisms. Such database can be developed using the general methods described above. Such database can be used to match the detected waveform(s) of an unknown microorganism sample to a known waveform(s) to identify the microorganism sample. In some situations, the detected waveform(s) of an unknown microorganism is not completely identical to any of the pre-stored waveforms. In some embodiments, the system identifies a pre-stored waveform(s) that is most similar to the detected waveform and calculates a similarity score. For example, the system can report to a user that there is an 80% chance that the unknown sample is *E. coli*. In other situations, different portions of a detected waveform(s) of an unknown microorganism can correspond to different pre-stored waveforms corresponding to different microorganisms. In certain embodiments, the system can determine what portion of the unknown sample corresponds to a first microorganism and what portion corresponds to a second microorganism. For example, the system can report to a user that the unknown plate of microorganisms is 30% *E. coli* and 70% *Bacillus atrophaeus*.

In an embodiment, a user can instruct the system to identify those pre-stored waveforms and corresponding microorganisms when the similarity is above a certain threshold level. This threshold level can be, for example, about 50%, about 60%, about 70%, about 80%, about 90%, about 91%, about 92%, about 93%, about 94%, about 95%, about 96%, about 97%, about 98%, about 99%, about 100%, or any other value.

In an embodiment, the system is configured to compare a detected waveform(s) to one or more compartments, ranges, and/or bands of waveforms. For example, the system can have pre-stored different compartments, ranges, and/or bands of waveforms that are each associated with a particular organisms or microorganism. In some embodiments, the compartments, ranges, and/or bands can be developed from multiple trials of detecting the waveform(s) of samples of the same or similar organisms or microorganisms and aggregating the detected waveform(s). In certain embodiments, the system can determine whether a detected waveform(s) fits within or substantially fits within one or more of these compartments, ranges, and/or waveforms and further identify the organism or microorganism associated with the one or more compartments, ranges, and/or waveforms.

The methods described above of using hyperspectral imaging to identify microorganisms or biological species greatly reduces the time and cost associated with performing such functions. For example, by using hyperspectral imaging to identify microorganisms, the whole identification process or a substantial portion thereof can be automated. Further, such methods can allow for analysis of multiple samples of microorganisms at once. In addition, once the identity of the unknown microorganism is determined, the system can further determine and report certain characteristics of that microorganism to the user. For example, such characteristics can comprise what the particular microorganism responds to or does not respond to. This can further reduce the cost and time associated with determining how to treat an unknown sample of microorganism.

FIGS. 15A and 15B illustrate one embodiment of how hyperspectral imaging can be used to determine the identity of microorganisms.

Hyperspectral Imaging and Virtual Staining for Clinical Diagnostics

The general methods of virtual staining using hyperspectral imaging as described above can also be applied in clinical diagnostics. Because hyperspectral imaging generally allows for analysis of more data and more content, better quality control and assurance of a specimen is possible for biobanking and downstream molecular diagnostics. In addition, inter/intra-specimen similarity score analysis is possible using hyperspectral imaging for biomarker discovery, validation, and development.

By employing the hyperspectral imaging methods described above, it is possible to analyze an image of a tissue sample according to each pixel or group of pixels and determine the particular waveform associated with each pixel or group of pixels. In an embodiment, multi-spectrum electromagnetic radiation or other imaging modality radiation is directed at a tissue sample of a known disease, condition, subtype thereof, or tissue that is susceptible or responsive to a particular treatment. Other types of radiation can include fluorescence, X-ray, ultrasound, infrared, MRI, PET, and/or CT spectrums. Electromagnetic radiation that is transmitted, reflected, or otherwise not absorbed by the tissue sample is detected by a detection device. The detected data is analyzed according to each pixel or group of pixels by a computer system to identify particular waveforms associated with each pixel or group of pixels. The detected waveforms are stored in the computer system as data correlating to the tissue sample of the known particular disease, condition, subtype(s) thereof, tissue that is susceptible or responsive to a particular treatment, or pathology. These steps can be repeated for a number of tissues of a number of diseases, conditions, subtypes thereof, tissues that are susceptible or responsive to a number of treatments, or pathology to develop a more comprehensive database. Meanwhile, waveform data of image pixels of healthy corresponding tissues can also be stored in the computer system as reference data.

In an embodiment, multi-spectrum electromagnetic radiation or other imaging modality radiation is directed at a tissue sample or specimen to be tested. Other types of radiation can comprise fluorescence, X-ray, ultrasound, infrared, MM, PET, and/or CT spectrums. The electromagnetic radiation that is transmitted, reflected, or otherwise not absorbed by the tissue specimen is detected by a detection device. The detected data is subsequently analyzed according to each pixel or group of pixels by a computer system to determine the waveform associated with each pixel or group of pixels. The computer system compares the detected pixel waveforms to the pre-stored database of waveforms associated with various tissue samples described above for classification, whether it be primary diagnosis or ancillary diagnosis. For example, if a particular waveform obtained from the tissue specimen is sufficiently similar to a pre-stored waveform of a tissue sample with a particular disease, condition, pathology, or subtypes thereof, then the corresponding portion of the tissue specimen is diagnosed with that particular disease, condition, pathology, or subtypes thereof. In some embodiments, waveform data obtained from the tissue specimen can be compared to multiple waveforms stored in a database to determine whether that tissue specimen is suffering from any number of diseases, conditions, pathology, or subtypes thereof.

In certain embodiments, the computer system is configured to diagnose a particular pixel waveform as degraded with a particular disease, condition, pathology, or subtypes thereof when the similarity in waveforms is above a certain percentage. For example, in some embodiments, the computer system will identify a particular waveform of a tissue specimen with a particular disease or subtype of disease when the waveform's similarity to a known waveform of a particular disease or subtype of disease is at about 90% or above. In other embodiments, this threshold value is about 50%, about 60%, about 70%, about 80%, about 90%, about 91%, about 92%, about 93%, about 94%, about 95%, about 96%, about 97%, about 98%, about 99%, about 100%, or any other value.

In an embodiment, the system is configured to compare a detected waveform(s) to one or more compartments, ranges, and/or bands of waveforms. For example, the system can have pre-stored different compartments, ranges, and/or bands of waveforms that are each associated with a particular disease, condition, pathology, or subtypes thereof. In some embodiments, the compartments, ranges, and/or bands can be developed from multiple trials of detecting the waveform(s) of samples with the same or similar disease, condition, pathology, or subtypes thereof and aggregating the detected waveform(s). In certain embodiments, the system can determine whether a detected waveform(s) fits within or substantially fits within one or more of these compartments, ranges, and/or waveforms and further identify the disease, condition, pathology, or subtype thereof associated with the one or more compartments, ranges, and/or waveforms.

In some embodiments, the computer system further pseudo-colors each pixel of the tissue specimen image according to a pre-stored database. For example, pixels associated with waveforms that correspond to those of healthy tissue are colored blue, while pixels associated with waveforms that correspond to those of diseased tissues are colored red. In other embodiments, the transform does not pseudo-color every pixel, but colors those pixels associated with waveforms that correspond to degraded tissues. In yet other embodiments, the output pixels of the virtual transform are not colored but are in grayscale. The output pixels are combined by a computer system to generate an output image of the tissue specimen that facilitates analysis or diagnosis of the tissue specimen. In other embodiments, the computer system does not pseudo-color or assign a particular grayscale shade to each pixel, but simply alerts a user in some manner of pixels associated with waveforms that correspond to degraded, unhealthy, or otherwise undesirable tissue.

In an embodiment, the system can also be configured to determine and suggest to a user a particular treatment for the tested tissue sample. For example, in some embodiments, the system can be configured to compare the detected waveforms from the tissue sample to known waveforms that correspond to tissue that are susceptible or responsive to certain treatments. Based on the comparison, the system can suggest a particular treatment for the tested tissue sample. Such treatments can include, for example, a particular drug, therapy, chemotherapy, radiation therapy, drug delivery method, among others. The system can be configured to suggest a particular treatment when the detected waveform is sufficiently similar to a pre-stored waveform of a tissue that is susceptible or responsive to a particular treatment. Such threshold value can be, for example, about 50%, about 60%, about 70%, about 80%, about 90%, about 91%, about 92%, about 93%, about 94%, about 95%, about 96%, about 97%, about 98%, about 99%, about 100%, or any other value.

In an embodiment, the system is configured to compare a detected waveform(s) to one or more compartments, ranges, and/or bands of waveforms. For example, the system can have pre-stored different compartments, ranges, and/or bands of waveforms that are each associated with samples that are susceptible or responsive to a particular treatment(s) or drug(s). In some embodiments, the compartments, ranges, and/or bands can be developed from multiple trials of detecting the waveform(s) of samples that are susceptible or responsive to the same or similar treatment(s) or drug(s) and aggregating the detected waveform(s). In certain embodiments, the system can determine whether a detected waveform(s) associated with a sample fits within or substantially fits within one or more of these compartments, ranges, and/or waveforms and further identify a particular treatment(s) or drug(s) that the sample is likely to be susceptible or responsive to. In an embodiment, the system can be configured to first determine the identity of a disease or subtype of a disease of the tissue sample according to the methods described above. The system can suggest a particular treatment based on a pre-stored database of treatments that are known to be effective to the identified disease or subtype of disease. For example, in some embodiments, a radiologist or other medical professional makes a primary diagnosis of a diseased tissue. The system can be employed to make an ancillary diagnosis or further classify the tissue sample according to a classification system or categorization within that disease and/or further suggest a particular treatment that is known to be effective for that category of the identified disease. In other embodiments, the system can be employed to make the primary diagnosis as well using the methods described above.

Figure 16:
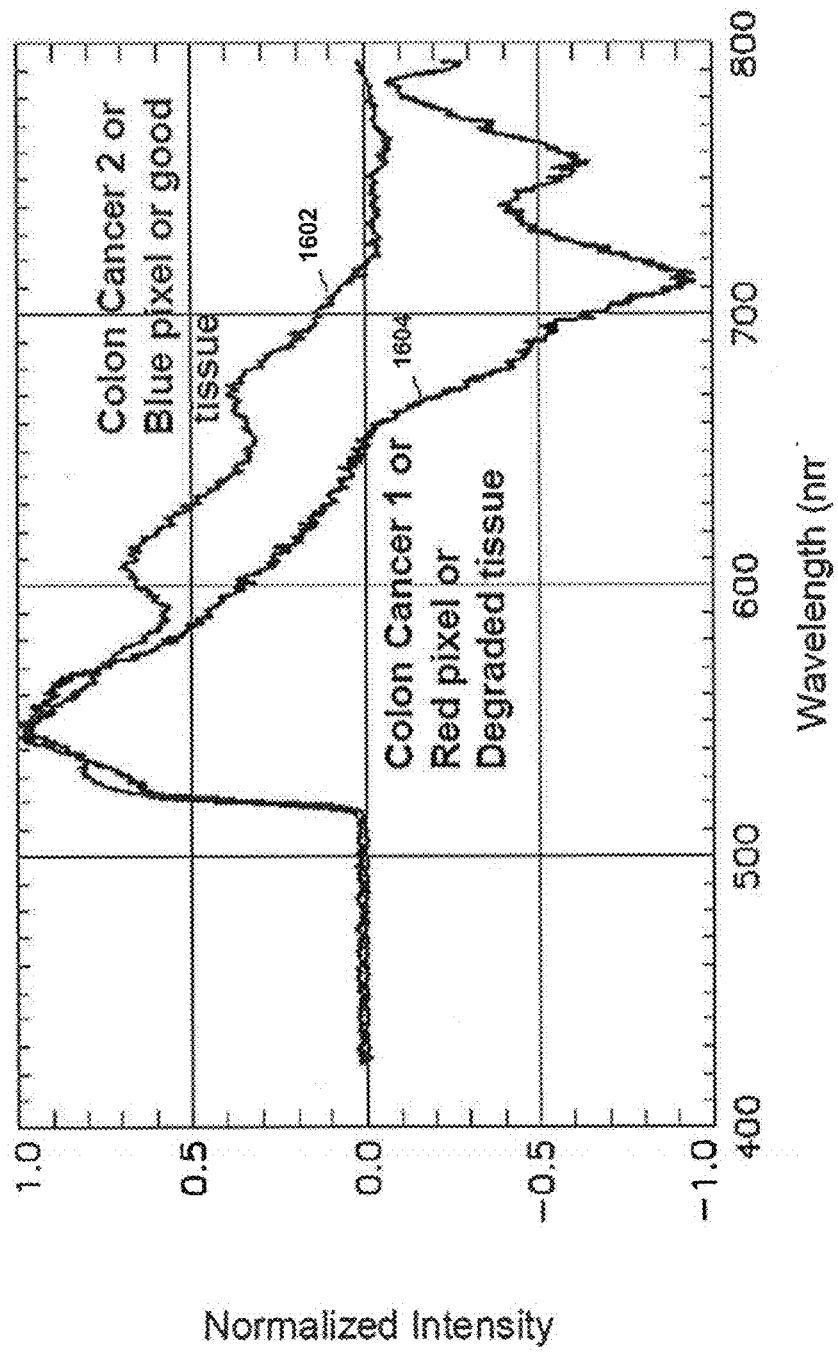
FIG. 16 depicts an example of one embodiment of a method of using hyperspectral imaging and detected waveforms to further classify a tissue(s) with colon cancer.

FIG. 16 depicts an example of one embodiment of a method of using hyperspectral imaging and detected waveforms to further sub-classify a tissue(s) with colon cancer. In the depicted embodiment, fluorescence light is directed at a tissue specimen with colon cancer. The detected fluorescence light that is transmitted, reflected, or otherwise not absorbed by the tissue specimen is analyzed according to each pixel or group of pixels of an initial image generated from the detected fluorescence. Each pixel or group of pixels can be associated with a particular waveform. In other embodiments, any other type of radiation, including multi-spectrum electromagnetic radiation, X-ray, ultrasound, infrared, MRI, PET, and/or CT spectrum can be directed at the sample. These waveforms are compared to a pre-stored database to determine whether a portion of the tissue specimen corresponding to each pixel is of a particular type of colon cancer.

In the depicted embodiment, waveforms associated with each pixel of an initial image of a tissue specimen or multiple tissue specimen are compared to a pre-stored database of waveforms associated with various types of colon cancer for ancillary diagnosis. Colon cancer, or any type of cancer in general, can be further classified as well-differentiated, moderately differentiated, or poorly differentiated. The system and methods described herein can provide means to easily classify a particular tissue or region of a tissue with cancer as well-differentiated, moderately differentiated, or poorly differentiated. In other embodiments, the system and methods described herein can also be used to make the primary diagnosis whether a patient has cancer or a particular type of cancer, such as colon cancer, as well.

In the depicted embodiment, once waveforms of a tissue specimen with colon cancer are identified, they are compared to a database containing waveforms associated with well-differentiated, poorly differentiated, and moderately differentiated colon cancers. In other embodiments, a colon cancer specimen or other tissue sample can be sub-classified according to any other classification or category. For example, the system can be configured to classify the tissue sample or regions within the tissue sample according to a disease type, a subtype of a disease, whether the region of the tissue will respond to a certain treatment or whether it is susceptible to a certain treatment, whether the region of the tissue is degraded or is healthy, among others. If there is a match or a sufficiently close match between the detected waveform(s) and the waveform in the stored database, the system classifies the waveform accordingly and reports to a user. The similarity threshold for matching a detected waveform to a pre-stored waveform can be set at various levels. For example, the similarity threshold can be set to about 50%, about 60%, about 70%, about 80%, about 90%, about 91%, about 92%, about 93%, about 94%, about 95%, about 96%, about 97%, about 98%, about 99%, about 100%, or any other value.

In the depicted example, a first waveform 1602 corresponds to a stored waveform associated with well-differentiated colon cancer or a good tissue. The pixel with this waveform can further be pseudo-colored as blue, or any other color, by the system for convenience of the user. On the other hand, a second waveform 1604 corresponds to the waveform associated with a poorly differentiated colon cancer or degraded tissue. The pixel with this waveform can further be pseudo-colored as red, or any other color, by the system for convenience of the user. If the system is configured to pseudo-color each pixel according to its waveform, as described above, these pixels can be combined by the system to output a single image that is colored accordingly so that a user can easily see which parts of the tissue has well differentiated or poorly differentiated colon cancer.

In an embodiment, once a tumor specimen is sub-classified using the methods described above, the system can be further configured to identify an appropriate treatment for that tissue or patient. For example, the system can comprise pre-stored data of what type of treatment(s) each particular type of cancer or subtype of cancer (or any other disease) responds to. Once the system identifies, classifies, or sub-classifies a tissue specimen according to certain categories, the system can suggest a particular treatment(s) to the user depending on such categorization. For example, the system can be configured to determine and report whether the patient or particular tissue of the patient will respond to chemotherapy, a particular type of chemotherapy, radiation treatment. The system can further be configured to determine and report whether the patient or a particular tissue of the patient will like be susceptible or resistant to a particular treatment(s), such as chemotherapy, a certain type of chemotherapy or radiation treatment.

Figure 17:
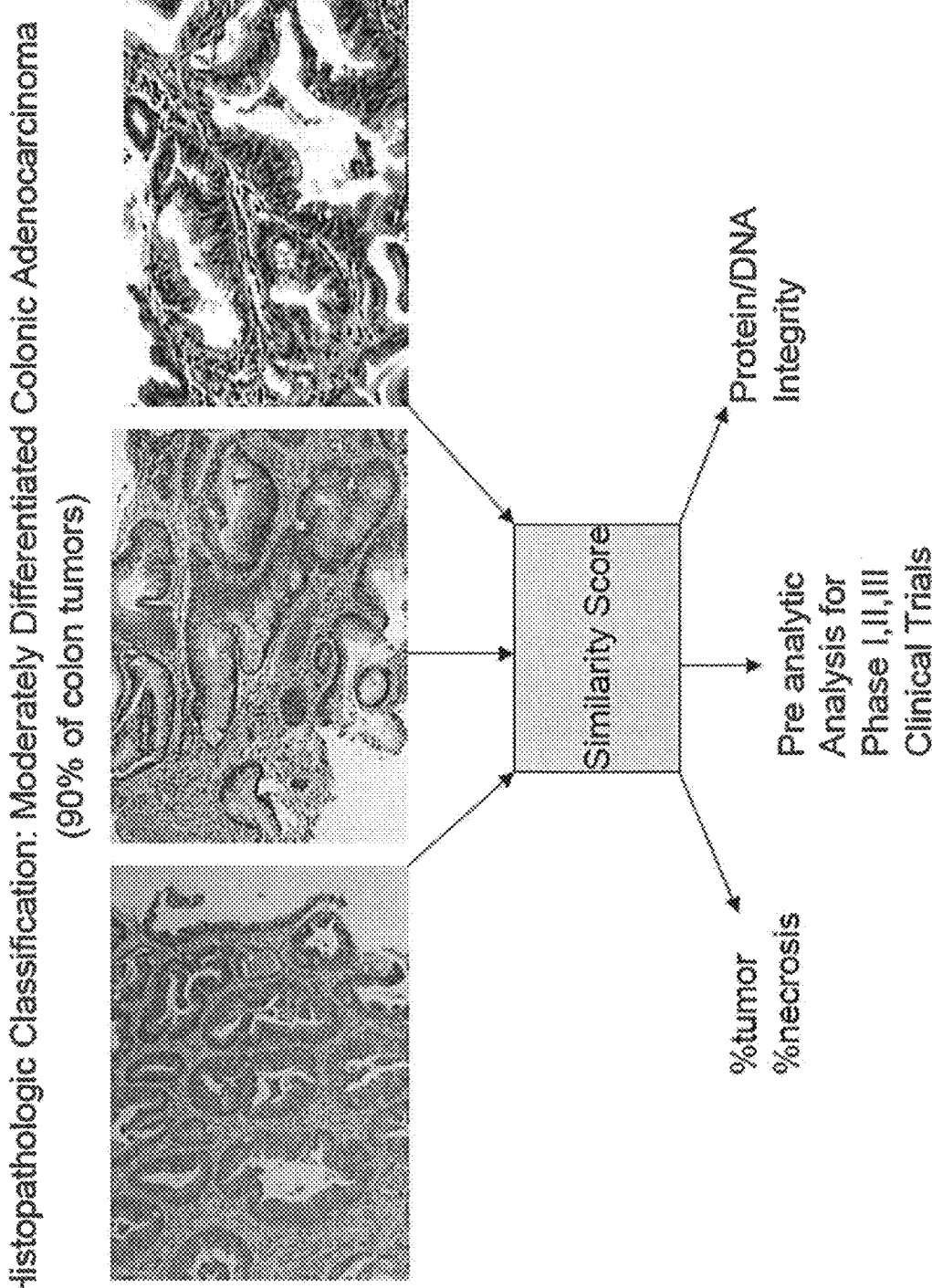
FIG. 17 depicts an example of one embodiment of a method of using hyperspectral imaging and detected waveforms to further classify moderately differentiated colonic adenocarcinoma according to histopathologic classifications.

FIG. 17 depicts an example of one embodiment of a method of using hyperspectral imaging and detected waveforms to further classify moderately differentiated colonic adenocarcinoma according to histopathologic classifications. In the depicted embodiment, electromagnetic radiation is directed at multiple tissue samples with moderately differentiated colonic adenocarcinoma. Given that 90% of colon tumors fall into this category, further classification can be useful. Once the waveforms associated with pixels of initial images of these samples are identified by the methods described above, the detected waveforms can be compared to known, pre-stored waveforms associated with various kinds of tissues. These pre-stored waveforms can comprise those associated with tissues with tumor or necrosis, with varying levels of protein/DNA integrity, those that are acceptable for clinical trials or molecular diagnosis, or those that are responsive or susceptible to a particular treatment, among others. The system can be configured to match the detected waveforms to one or more of the aforementioned pre-stored waveforms when the waveforms are sufficiently similar. For example, this threshold level can be set at about 50%, about 60%, about 70%, about 80%, about 90%, about 91%, about 92%, about 93%, about 94%, about 95%, about 96%, about 97%, about 98%, about 99%, about 100%, or any other value.

In an embodiment, the system can be further configured to calculate and report a numerical similarity score of the detected waveform to one or more pre-stored waveforms. Depending on the type of pre-stored waveform used as a point of comparison, the system can sub-classify or characterize the tissue sample according to a number of metrics. For example, the system can determine the percentage of tumor or necrosis present in the tissue sample by comparing the detected waveforms to waveforms associated with tumor or necrosis. In addition, the system can determine whether the tissue sample is appropriate for clinical trial or molecular diagnosis by comparing the detected waveforms to waveforms associated with tissues that are known to be appropriate for a particular clinical trial or molecular diagnosis. Further, the system can determine the protein/DNA integrity of the tissue sample by comparing its waveforms to those associated with differing protein/DNA integrity. Using such further characterization or classification of the tissue sample, either the system or a medical professional can determine an appropriate treatment.

Figure 18:
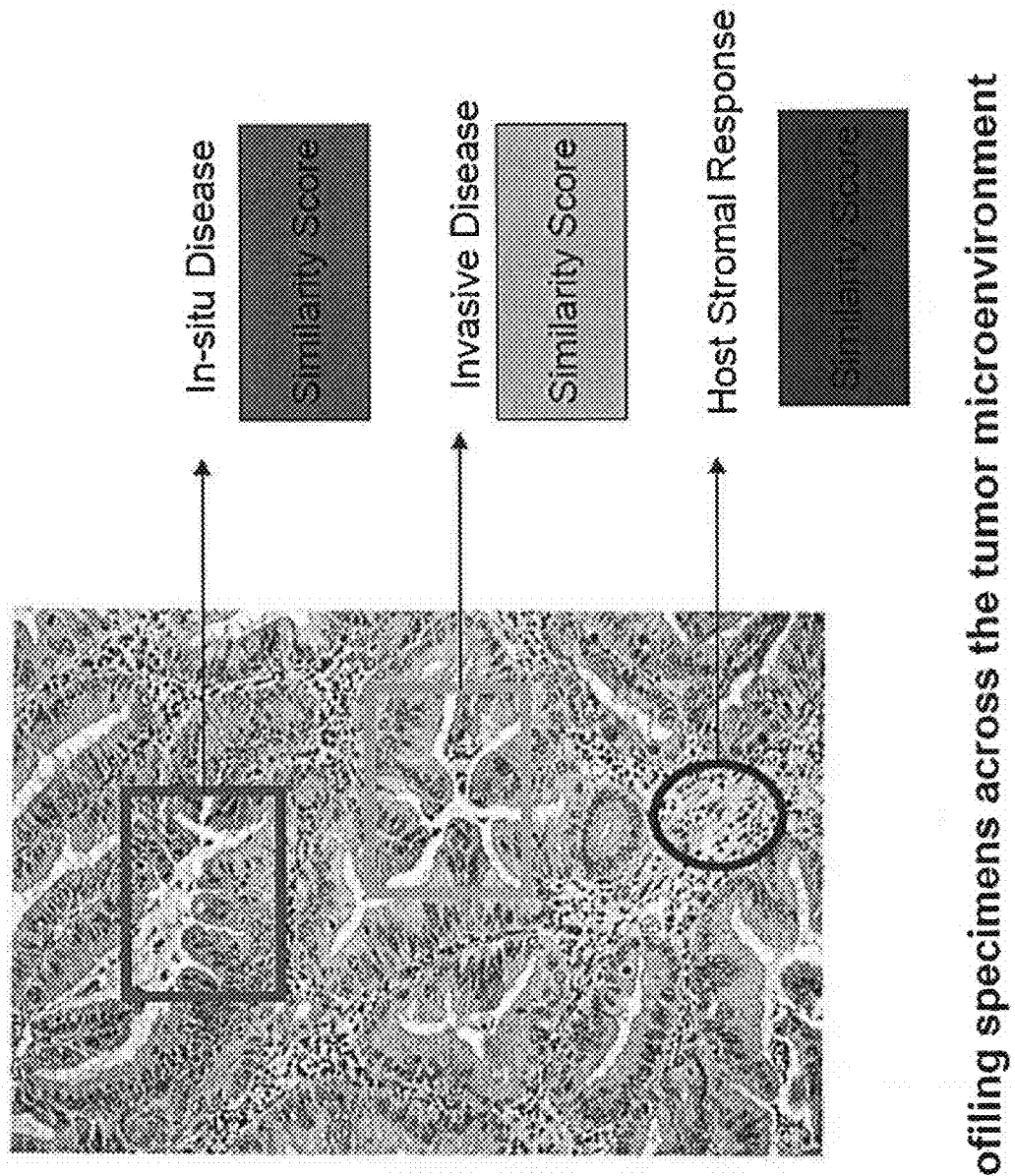
FIG. 18 depicts an example of one embodiment of a method of using hyperspectral imaging and detected waveforms to profile specimens across a microenvironment.

FIG. 18 depicts an example of one embodiment of a method of using hyperspectral imaging and detected waveforms to profile specimens across a microenvironment. In the depicted embodiment, waveforms associated with different regions of a single tissue sample are compared to pre-stored waveforms associated with tissues with in-situ diseases, invasive diseases, and host stromal responses. The system can be further configured to calculate a numerical similarity score based on each of the aforementioned comparisons. Depending on the calculated similarity score, a medical professional or the system can further determine an appropriate treatment or further testing.

Figure 19:
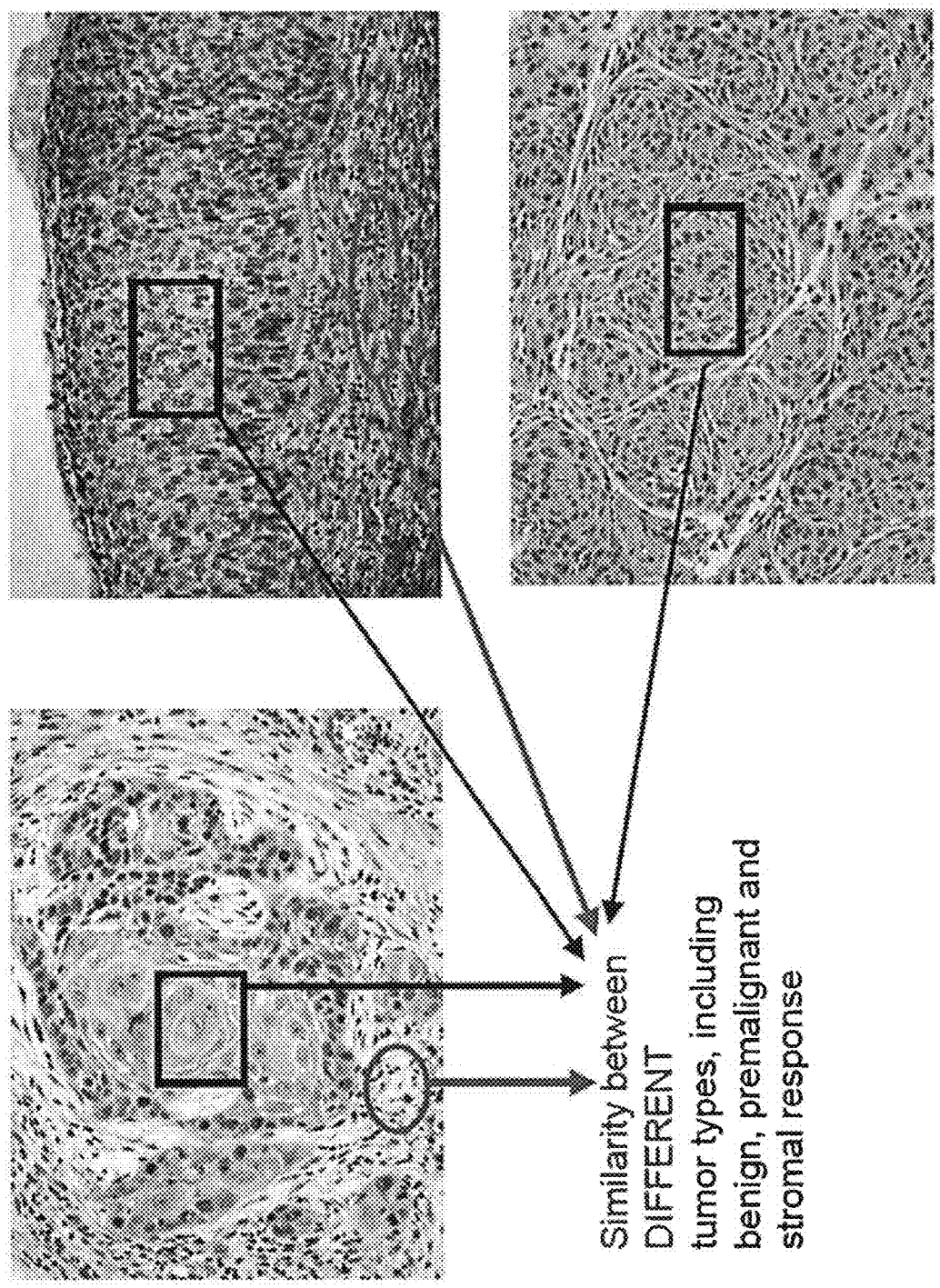
FIG. 19 depicts an example of one embodiment of a method of using hyperspectral imaging and detected waveforms to further classify and compare different tumor types.

FIG. 19 depicts an example of one embodiment of a method of using hyperspectral imaging and detected waveforms to further classify and compare different tumor types. Tissues with certain types of diseases can have similar associated waveforms with tissues of different types of diseases. For example, tissues with certain types of pancreatic cancers can have similar associated waveforms with tissues with certain types of colon cancer. Tissues with these types of pancreatic cancers can be responsive to the same type of treatment or should be included in the same clinical trials as tissues with these types of colon cancer. The systems and methods described herein can be employed to determine which types of pancreatic cancer are associated with similar waveforms to colon cancer and thus should be treated with the same means or included in the same clinical trials.

In the depicted example, waveform signatures associated with a tissue sample with a particular disease or type of cancer are identified. The detected waveforms are compared to pre-stored waveforms associated with different tumor types, including benign, premalignant, and stromal response. In some embodiments, the system is further configured to calculate a numerical similarity score based on the comparison. For example, the waveform associated with a tissue with type 1 of cancer A can have a similarity score of 90 when compared to the waveform associated with a tissue with type 2 of cancer B. If a similarity score of 90 is above a set threshold, the system can further be configured to put type 1 of cancer A and type 2 of cancer B in the same category for clinical trials or for a particular treatment. This threshold value can be set at about 50%, about 60%, about 70%, about 80%, about 90%, about 91%, about 92%, about 93%, about 94%, about 95%, about 96%, about 97%, about 98%, about 99%, about 100%, or any other value.

Figure 20:
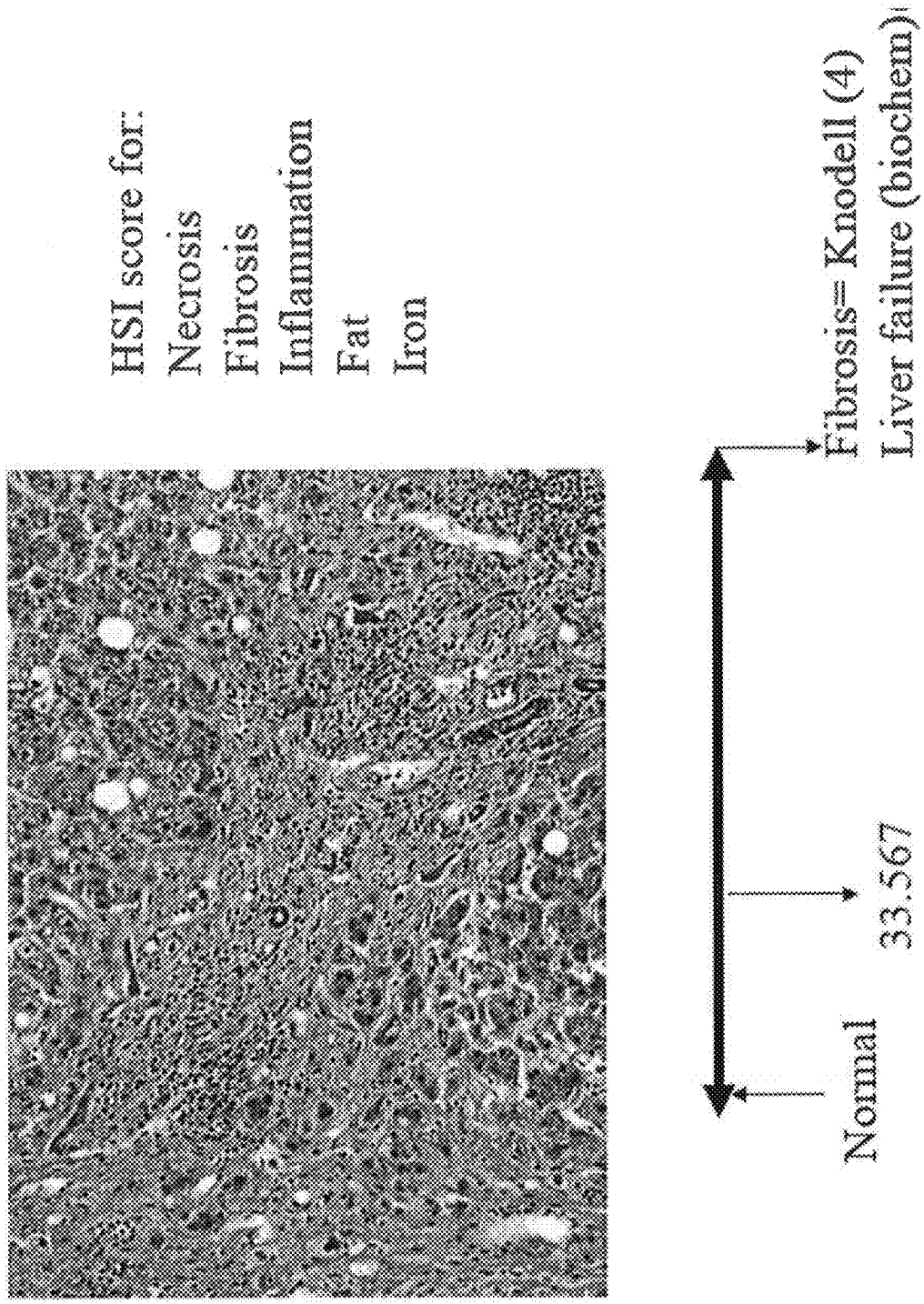
FIG. 20 depicts an example of one embodiment of a method of using hyperspectral imaging and detected waveforms to quantitatively grade a pathological disease or condition.

FIG. 20 depicts an example of one embodiment of a method of using hyperspectral imaging and detected waveforms to quantitatively grade a pathological disease or condition. Existing methods of grading or diagnosing the severity or procedural state of a particular disease, condition, or subtypes thereof, such as the grading system for hepatitis, are generally subjective. Different medical professionals can have different opinions as to the severity or procedural state of a tissue sample diagnosed with a particular disease, condition, or subtypes thereof. The methods and systems described herein can provide a uniform system of assigning a numerical value to the severity or procedural state of a particular disease, condition, or subtypes thereof. The disease, condition, or subtype thereof can be anything, including necrosis, fibrosis, inflammation, fat, or iron.

In an embodiment, waveforms associated with tissue samples with varying stages or severity of a particular disease, condition, or subtype thereof can be identified and stored in a database. These pre-stored waveforms can be used as milestones for determining the severity or procedural stage of a tissue with a disease, condition, or subtype thereof to be examined. For example, the waveform associated with a healthy or normal tissue can be identified and stored. The waveform associated with a tissue with the worst known case of a particular disease, condition, or subtype thereof can also be identified and stored as a standard for the worst case. The waveforms associated with any number of tissues with the same disease, condition, or subtype thereof but in different stages or severity can also be identified and stored based on the need. Such stored waveforms can act as points of comparison for the tissue sample to be tested. For example, a waveform associated the tissue sample to be tested can be detected and compared to one or more of such standard pre-stored waveforms. Based on the similarity of the detected waveform(s) to the pre-stored standard waveforms, the system can be configured to calculate a numerical score for the tissue sample, which can be used to determine the severity or procedural stage of the particular disease, condition, or subtype thereof of the tissue sample. The method described above can be applied to any disease, In the depicted embodiment, one end of the grading spectrum is a waveform associated with a normal tissue. The other end of the grading spectrum is a waveform associated with a tissue with the worst known case of fibrosis. Waveforms associated with a tissue sample to be examined are obtained and are compared to these two standard waveforms. In other embodiments, the detected waveforms are compared to additional standard waveforms associated with tissues with less severe fibrosis as well. Based on such comparisons, the system calculates a numerical score of the severity of fibrosis in the tissue sample according to a pre-determined algorithm. For example, in the depicted embodiment, the tested tissue sample was determined to have a numerical score of 33.567. A medical professional can use this numerical score to objectively diagnose the state of the pathological disease, condition, or subtype thereof of the tested tissue sample. In some embodiments, the system or a medical professional can use this numerical score to determine an appropriate treatment or drug for the patient as well. In certain embodiments, the system comprises a database with appropriate treatments and drugs according to the severity or procedural stage of a particular disease, condition, or subtype thereof. In some embodiments, the same treatment or drug can correspond to a range of numerical scores obtained by the methods described above. From this database, the system can suggest a particular drug or treatment to the user.

Vector Signature Analysis

Figure 21:
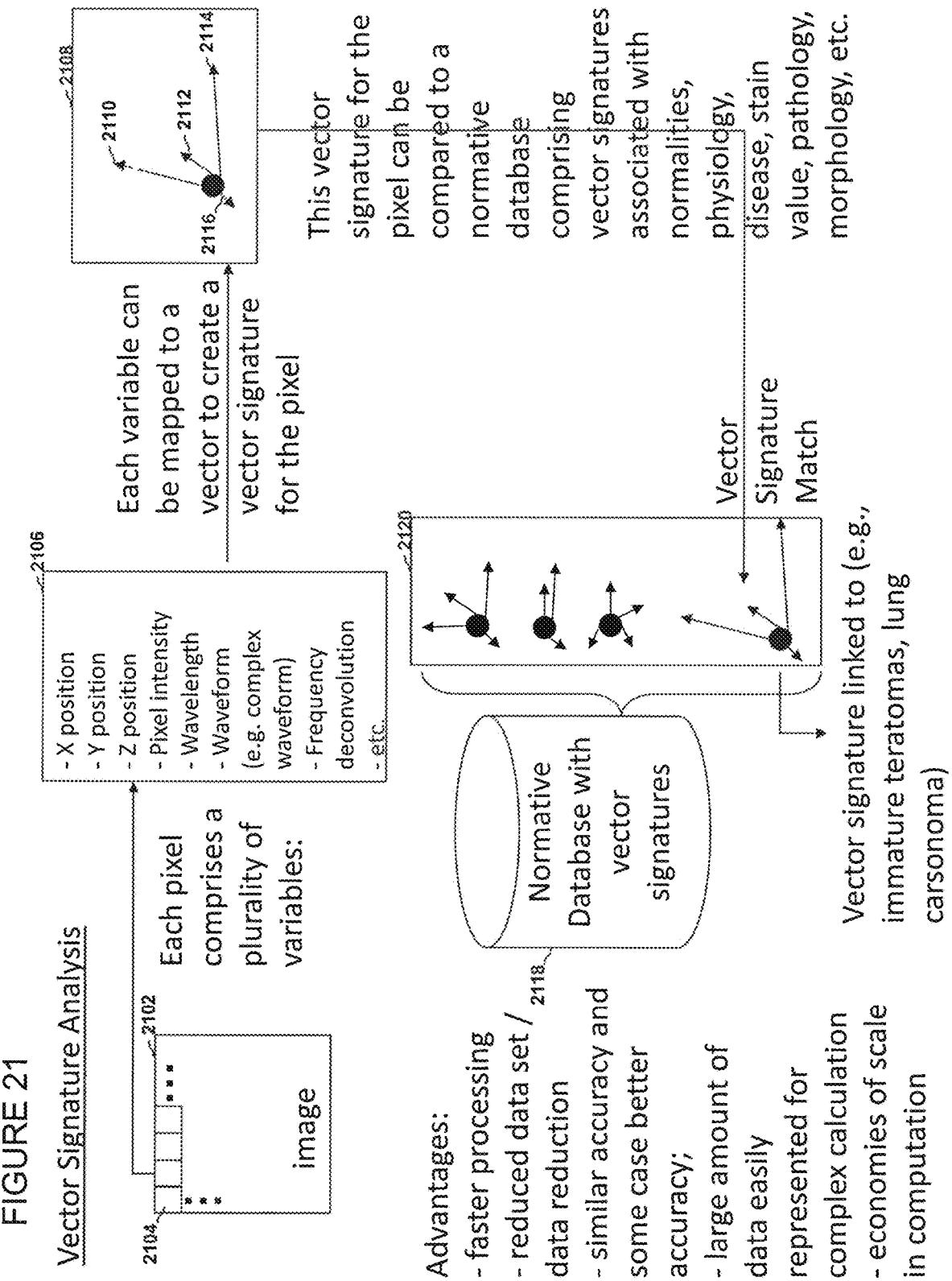
FIG. 21 is a block diagram depicting an overview of one embodiment of using vector signature analysis to analyze each pixel of a detected image of a tissue sample.

The methods discussed above, including but not limited to developing a virtual staining transform, virtually staining a sample, and using hyperspectral imaging for clinical diagnostics, generally involved analyzing waveform signatures associated with each pixel or group of pixels. In an embodiment, vector signature analysis can be used, either concurrently or as an alternative to waveform signature analysis, to analyze a tissue sample or other sample. Vector signature analysis can provide faster processing and/or a reduced data set while maintaining similar accuracy to waveform signature analysis. Vector signature can further allow representation of a large amount of data for complex calculations and can achieve economies of scale in computation. FIG. 21 is a block diagram depicting an overview of one embodiment of using vector signature analysis to analyze each pixel of a detected image of a tissue sample.

In the depicted embodiment, an image 2102 obtained from a tissue sample to be analyzed comprises a plurality of pixels 2104. Each pixel further comprises a plurality of variables 2106. Such variables 2106 can comprise but is not limited to the x position, y position, z position, pixel intensity, wavelength of the pixel, waveform, complex waveform, frequency deconvolution, waveform deconvolution, among others. Any number of such variables can be mapped to a vector to create a vector signature 2108 for each pixel position or pixel 2104. For example, the vector 2108 of a particular pixel can comprise a first component 2110 that corresponds to the pixel's x position, a second component 2112 that corresponds to the pixel's y position, a third component 2114 that corresponds to the pixel's z position, a fourth component 2116 that corresponds to the pixel's intensity level, and a fifth component that corresponds to the pixel's wavelength. In other embodiments, a vector 2108 associated with each pixel 2104 can comprise a subset of these variables 2106 or can comprise additional variables as well.

In an embodiment, vector signatures associated with pixels obtained from images of tissue samples to be used as standards 2120 can be determined and stored in a normative database 2118. For example, when developing a virtual staining transform, vector signatures associated with pixels comprising images of unstained and stained tissue samples 2120 can be determined and stored in the database 2118. Data of vector signatures associated with different stain values can be used to determine how pixels obtained from an image of another tissue sample are to be transformed to output pixels after virtually staining the tissue sample. Also, vector signatures associated with pixels obtained from images of normal or healthy tissue samples or those with particular diseases, conditions, physiology, pathology, morphology, subtypes thereof, or of a particular stage or severity can be determined and stored in the database as well. These vector signatures can be used by the system as points of comparison to match or substantially match vector signatures obtained from another tissue sample 2108 to classify, sub-classify, or diagnose the another tissue sample. The system can also determine a level of similarity between vector signatures obtained from another tissue sample 2108 and one or more stored vector signatures 2120. For example, the system can identify that a detected vector signature of a tissue sample matches or is sufficiently similar to a vector signature linked to immature teratomas, lung carcinoma, or any other disease, condition, physiology, pathology, or morphology, among others.

In Vivo Applications of Virtual Staining

As described herein, in some embodiments, virtual staining can be performed on a target biological tissue sample in vivo. A device having virtual staining capability may be used in vivo as part of an exploratory and/or surgical procedure. A virtual staining device can be delivered into a human or other body to facilitate use of hyperspectral imaging in vivo to provide objective analysis of biological tissue without surgical removal and/or isolation of the tissue. In some embodiments, virtual staining can be advantageously applied in vivo to facilitate real-time delivery of appropriate medical treatment to target sites within the human body.

Figure 22:
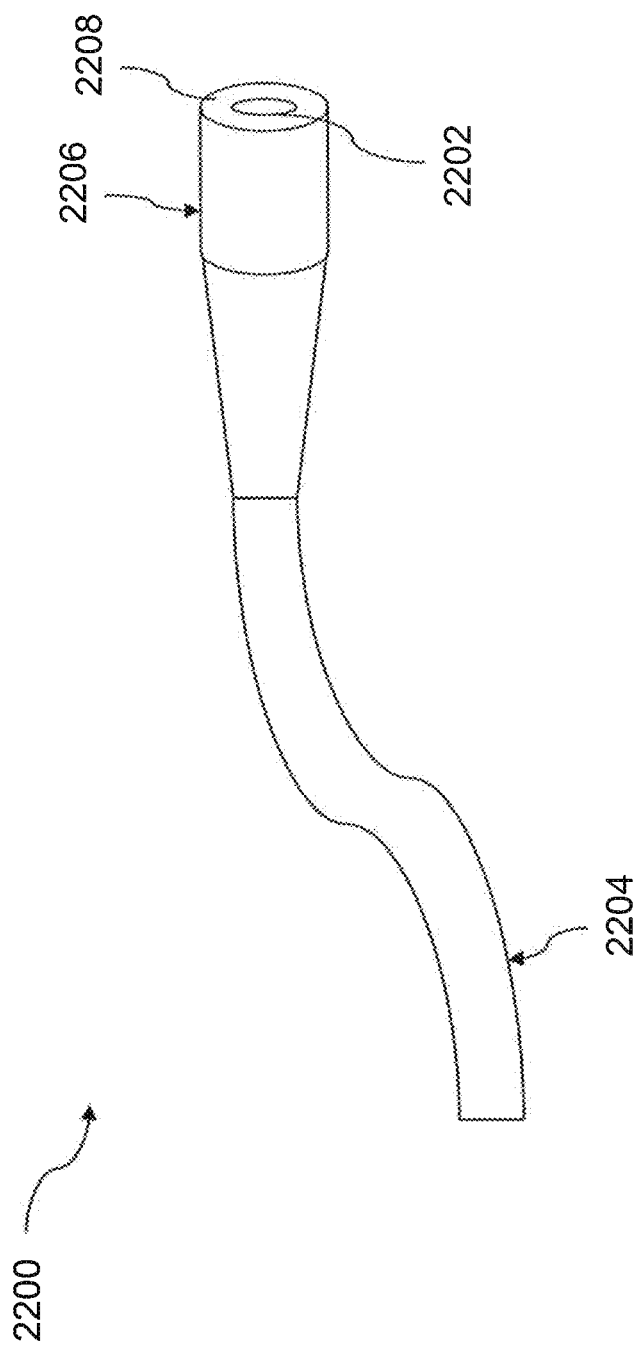
FIG. 22 depicts an example medical probe into which a virtual staining device may be incorporated.

Referring to FIG. 22, in some embodiments, a virtual staining capability can be provided to a tissue sample within a human body by integrating a virtual staining device 2202 into a medical probe 2200 which can be inserted into the human body. FIG. 22 shows a portion of an example medical probe 2200 into which a virtual staining device 2202 can be integrated. The medical probe 2200 can have a proximal portion 2204 and a distal portion 2206. In some embodiments, the virtual staining device 2202 can be integrated into a distal portion 2206 of the medical probe 2200, for example to facilitate positioning of the virtual staining device 2202 at or near a target tissue sample within the human body. The virtual staining device 2202 may include an electromagnetic radiation emitting source and an electromagnetic radiation detector, and/or any other suitable component, to facilitate directing of an electromagnetic radiation having a bandwidth within desired ranges at a tissue sample to be virtually stained and detecting electromagnetic radiation reflected and/or transmitted from the tissue sample. Exposure of examined tissue to an electromagnetic radiation source and/or an electromagnetic radiation detector may be at a distal surface 2208 of the probe 2200. In some embodiments, the probe could be part of an endoscope, laparoscope, or other medical instrument. An electromagnetic radiation source and/or detector may be exposed to investigated tissue along other surfaces of the distal portion 2206, and/or other portions of the medical probe 2200. Hyperspectral imaging information gathered by the virtual staining device 2202 may be provided to a computing system for analysis, including real-time analysis of the information.

In some embodiments, the probe may be adapted for direct access to a target site, without the use of a distinct tubular access catheter. In general, whether used with an access sheath or as a stand alone device, the dimensions of the probe can be optimized by persons of skill in the art in view of the present disclosure to suit any of a wide variety of target sites. For example, the probe can be used to obtain hyperspectral and other images and data from large and small arteries and veins throughout the cardiovascular system, as well as other lumens, potential spaces, hollow organs and surgically created pathways. Data collection may be accomplished in blood vessels, body lumens or cavities, such as the lymphatic system, esophagus, trachea, urethra, ureters, fallopian tubes, intestines, colon, biliary ducts, spinal canal and any other locations accessible by a flexible or rigid probe. The probe may also be adapted for direct advance through solid tissue, such as soft tissue or through bone, for site specific diagnosis and treatment.

In some embodiments, a probe generally comprises an elongate body extending between a proximal end and a distal functional end. The length of the body depends upon the desired access site and the desired placement site for the distal end. For example, lengths in the area of from about 1 cm to about 20 or 30 cm may be useful in applications that require the catheter to be advanced down a relatively short tubular access sheath. Longer lengths may be used as desired, such as on the order of from about 120 cm to about 140 cm for use in percutaneous access at the femoral artery for placement of the distal end in the vicinity of the coronary artery. Intracranial applications may call for a different catheter shaft length depending upon the vascular access site, as will be apparent to those of skill in the art.

In some embodiments, at least the proximal section of body may be produced in accordance with any of a variety of known techniques for manufacturing catheter bodies, depending upon the desired clinical performance. For example, the body may be formed by extrusion of any of a variety of appropriate biocompatible polymeric materials. Known materials for this application include high density polyethylene, polytetrafluoroethylene, nylons, PEEK, PEBAX and a variety of others. Alternatively, at least a proximal portion or all of the length of body 16 may comprise a spring coil, solid walled hypodermic needle tubing, or braided reinforced wall, as is understood in the catheter and guidewire arts. Whether metal or polymeric or a hybrid, the body may be hollow or solid depending upon the nature of the binding system and other desired capabilities.

In one example, the body is provided with an approximately circular cross-sectional configuration. Alternatively, generally rectangular, oval or triangular cross-sectional configurations can also be used, as well as other noncircular configurations, depending upon the method of manufacture, desired surface area, flexibility, access pathway and other design considerations that may be relevant for a particular application.

Dimensions outside of the ranges identified above may also be used, provided that the functional consequences of the dimensions are acceptable for the intended purpose of the catheter. For example, the lower limit of the cross section for any portion of body in a given application will be a function of the number of fluid or other functional lumens, if any, contained in the probe, together with the desired surface area to be available for the binding partner, as will be discussed.

Probe body in some embodiments should also have sufficient structural integrity (e.g., column strength or "pushability") to permit the probe to be advanced to a desired target site without buckling or undesirable bending.

The distal end of the probe may be provided with an atraumatic distal tip which may include a guidewire exit port in a guidewire lumen embodiment as is known in the art. A radiopaque marker may be provided on the probe body in the case of relatively long probes to facilitate positioning of the probe as is known in the art. Suitable marker bands can be produced from a variety of materials, including platinum, gold, and tungsten/rhenium alloy.

In some embodiments, the probe 2200 can include a plurality of virtual staining devices 2202. In some embodiments, a virtual staining device 2202 can be integrated into a distal portion 2206 and/or one or more other portions of the medical probe 2200 to facilitate collection of hyperspectral imaging information from target tissue sample within the human body. In some embodiments, the probe 2200 can be delivered to a target site within one or more other delivery apparatuses to facilitate positioning of the virtual staining device 2202. For example, the probe 2200 may be delivered to a target site through a catheter inserted into a body lumen, such as an artery or vein, for example. In some embodiments, the medical probe and/or any other delivery device through which the virtual staining device is positioned into the human body can have a flexible and/or rigid portion, and/or other suitable characteristics. The probe 2200 and/or any other delivery device may have other characteristics common to delivery devices, including but not limited to features to allow control and/or manipulation of the virtual staining device, such as curvable and/or steerable in some embodiments, e.g., via the use of pullwires operably connected to a control.

The virtual staining device 2202 may be inserted into a human body through a natural orifice and/or through an incision, such as surgically, laparoscopically, or percutaneously for example. The virtual staining device 2202 may be inserted into any number of body cavities, including for example the thoracic cavity, the abdominal cavity and/or the pelvic cavity, for examination of tissue accessible within the cavities. In some embodiments, the virtual staining device may be used for analysis of a digestive tract lining. For example, a virtual staining device may be introduced orally (e.g., swallowed) for investigation of a tissue region along the digestive tract (e.g., tissue lining an esophageal tract, the stomach, and/or the intestines).), and can be configured in some embodiments similar to a capsule endoscopy, wirelessly communicating hyperspectral information to a computer. In some embodiments, the virtual staining device can be inserted to investigate the respiratory tract, including but not limited to tissue lining a nasal cavity, oral mucosa, or portion of the bronchial tree. The virtual staining device may be inserted into other natural orifices for analysis of target tissue lining the orifice. In some embodiments, the virtual staining device may be inserted into a biological space through an incision made near a target site or distal from a target site. In some embodiments, the device need not even enter the body. For example, in some embodiments, a device comprising a hyperspectral imaging apparatus can be in the form of a wand-like or other configuration and waved or otherwise positioned in proximity to the skin, eyes, or other externally accessible anatomical structures in order to screen for or diagnose medical conditions. For example, a wand-like hyperspectral imaging apparatus can be positioned in proximity to the skin to screen for or diagnose in real-time (without necessarily a need for surgical biopsy) a cancerous or pre-cancerous lesion such as melanoma, squamous cell carcinoma, or basal cell carcinoma, for example.

The virtual staining device 2202 may be part of an exploratory medical procedure to investigate a particular region of tissue using hyperspectral imaging. In vivo application of the virtual staining technique may provide a mode of in vivo tissue visualization. In vivo virtual staining may be used to visualize an extended region and/or a targeted region of tissue. In vivo analysis of biological tissue may facilitate a minimally invasive method of identifying suspicious tissue. In some embodiments, in vivo analysis can facilitate identification of suspicious tissue before the diseased tissue can be identified through other means of detection. For example, tissue of interest may be identified for future monitoring, and/or for examination through another method of analysis. In some embodiments, in vivo hyperspectral analysis can be used to identify a benign tissue mass, avoiding unnecessary surgical procedures. The virtual staining device 2202 may be positioned in locations otherwise difficult to access. The virtual staining device 2202 can be used to visualize various tissues in the human body, including tissues lining various body cavities, and/or tissue on and/or within internal organs (e.g., epithelial cells, including or endothelial cells for example).

In some embodiments, the virtual staining device 2302 can be used in conjunction with another diagnostic imaging modality to facilitate placement of the virtual staining device. For example, the imaging modality may be used to provide three-dimensional (3-D) visualization of surrounding biological tissue, to facilitate placement of the virtual staining device to a desired location within the biological space. Image guided placement of a virtual staining device may facilitate targeted application of the virtual staining device. For example, once inserted at and/or near the target region within the biological space, the virtual staining device may then begin to provide analysis of the tissue. Any number of traditional imaging modalities may be advantageously used in conjunction with a virtual staining device. Suitable imaging modalities can include, but are not limited to, acoustic microscopy (e.g., ultrasound), radiography (e.g., plain film X-rays, fluoroscopy, mammography), computed tomography, magnetic resonance imaging (MRI), and/or endoscopyPET, and others.

In some embodiments, ultrasound-based technology can be used to facilitate placement of a virtual staining device into the human body. For example, an ultrasound transducer may be placed on an exterior skin surface over a region of the body in which virtual staining of tissue is desired, such that an ultrasound scanner can provide real-time visualization of surrounding tissue to aide positioning of the virtual staining device (e.g., the virtual staining device 2202 integrated onto the probe 2200, as shown in FIG. 22, and/or any other suitable delivery device through which a virtual staining device can be delivered). In some embodiments, a patient and/or a portion of the patient being examined may be positioned in a radiography, and/or magnetic resonance imaging tool, to provide real-time images of internal tissue to guide insertion of the virtual staining device. For example, fluoroscopy may be used to collect real time moving images of the digestive system by introducing a substance which is opaque to X-ray (e.g., barium sulfate) into the digestive system (e.g., through swallowing by the patient, and/or as an enema). For example, magnetic resonance imaging technology may be used to provide real-time visualization of tissue within reproductive organs and/or breast tissue.

Figure 23:
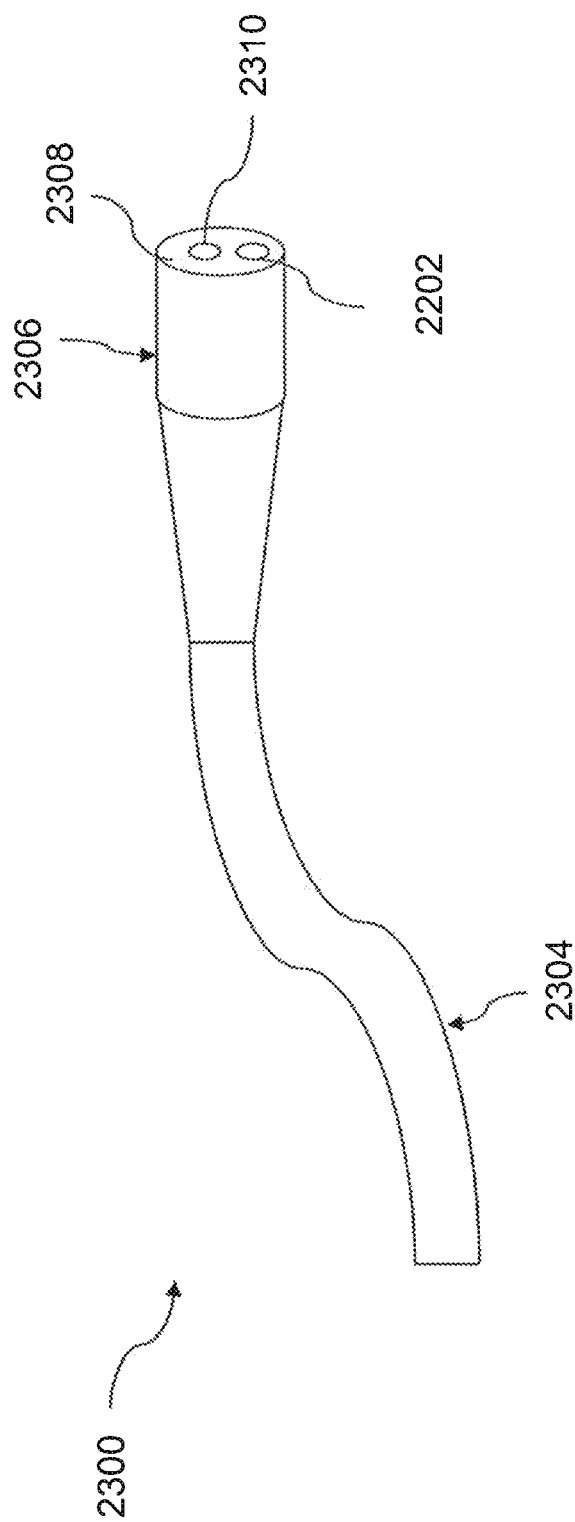
FIG. 23 depicts another example medical probe into which a virtual staining device may be incorporated.

In some embodiments, an additional imaging modality may be integrated into a medical probe to use in conjunction with a virtual staining device. Referring to FIG. 23, in some embodiments, a virtual staining device 2302 can be integrated into a medical probe 2300 for use in conjunction with one or more other diagnostic imaging modalities 2310 for insertion of both the virtual staining device 2302 and an additional imaging modality 2310 into the human body. The diagnostic imaging modality 2310 may facilitate placement of the virtual staining device 2302. For example, the imaging modality may be used to provide three-dimensional (3-D) visualization of surrounding biological tissue, to facilitate placement of the virtual staining device to a desired location within the biological space, facilitating targeted application of the virtual staining device.

Referring to FIG. 23, one or more additional diagnostic imaging modalities can be integrated into a medical probe 2300 for insertion into the human body, for example together with a virtual staining device 2302. For example, the probe 2300 may include a proximal portion 2304 and a distal portion 2306. The additional diagnostic imaging modalities can be exposed to tissue at the distal portion 2306 of the probe 2300 (e.g., the additional diagnostic imaging modality being exposed to tissue samples at a distal surface 2308 of the probe 2300). The virtual staining device 2302 and/or the additional diagnostic imaging modalities may be exposed to surrounding tissue along surfaces on other portions of the probe 2300. In some embodiments, an additional diagnostic imaging modality may not be integrated onto a probe 2300 but may be delivered into the human body through a delivery catheter, the delivery catheter may or may not be a catheter through which the virtual staining device 2302 is delivered. In some embodiments, the additional diagnostic imaging modality may be delivered through a different delivery device and/or through a different incision and/or natural orifice.

In some embodiments, a suitable imaging modality 2310 for delivery into a body cavity to facilitate placement of a virtual staining device 2302 can include providing a light source to the region under inspection to illuminate surrounding tissue. In some embodiments, a fiber optic technology can be used. For example, an additional imaging modality 2310 may include endoscopy, using an endoscope for visualization within a biological space to facilitate positioning of the virtual staining device 2302. Endoscopy may be used to facilitate positioning of the virtual staining device 2302 in a variety of spaces within the human body, including for example within the digestive tract, the respiratory tract, the urinary tract, a reproductive organ, and/or any other organ into which an endoscope may be inserted.

In some embodiments, a virtual staining device can be used together with one or more surgical instruments to provide both in vivo real-time hyperspectral analysis and treatment of biological tissue. The surgical instrument and a virtual staining device may be incorporated into a common medical probe (e.g., 2300) and/or may be delivered through a shared delivery catheter. Various configurations of the medical probe and/or other deliver device may be suitable to facilitate access of the virtual staining device and the surgical tool to the target tissue. In some embodiments, the one or more surgical instruments may not be integrated onto a shared probe and/or be delivered through a shared delivery catheter. In some embodiments, the one or more surgical instruments may be delivered through a different delivery device and/or through a different incision and/or natural orifice. In some embodiments, the probe is configured such that the hyperspectral or other diagnostic component is operably connected to a processor that the patient has a particular medical condition. The processor could then alert the operator to manually activate the therapeutic component of the probe, or automatically activate the therapeutic portion of the probe.

For example, a virtual staining device may be inserted into the human body together with a surgical tool capable of performing real-time operation on a target tissue site and/or delivery of medical therapy to the target tissue site, facilitating minimally invasive operations. In some embodiments, a virtual staining device can be inserted into a biological space along with surgical tools to facilitate removal of tissue from target sites (e.g., a mechanical cutter, a needle, and/or a vacuum-assisted device). Tissue may be sampled for further analysis (e.g., for a biopsy of the tissue sample) and/or may be removed for disposal (e.g., excision of diseased tissue). In some embodiments, a virtual staining device may be used to identify tissue for in vivo delivery of medical therapy. For example, a virtual staining device and a cryoprobe be inserted into the human body to identify tissue for application of cryosurgery in disposing of diseased tissue, and to deliver cryotherapy to the diseased tissue, (e.g., suitable for treatment of liver cancer, prostate cancer, lung cancer, oral cancers, cervical disorders, and/or hemorrhoids). In some embodiments, a virtual staining device can be used in conjunction with a laser source and/or an energy delivery or other therapeutic agent, such as, for example, microwave, radio-frequency ablation, high-intensity focused ultrasound source, laser, infrared, incoherent light, thermal (heat and/or cold, ablative or non-ablative), use of vacuum or suction, and the like. In vivo hyperspectral imaging may be used to facilitate delivery of other suitable therapies.

The probe may further comprise an optional therapeutic reservoir capable of retaining and releasing one or more therapeutic agents, such as drug compounds, antibodies, stem cells, or other substances. In some embodiments, the drug could be a chemotherapeutic agent, an anti-inflammatory agent, an antibiotic, an anti-thrombotic agent, a combination of the foregoing, or others.

In some embodiments, a virtual staining device may be applied in vivo together with both one or more additional imaging modalities, and one or more surgical instruments for operating on target tissue. For example, an additional imaging modality may facilitate positioning of the virtual staining device and the surgical instruments may facilitate removal of and/or treatment of identified suspicious tissue samples. The one or more surgical instruments and/or additional imaging modalities may or may not be integrated onto a shared probe and/or are delivered through a shared delivery catheter. The one or more surgical instruments and/or additional imaging modalities may be delivered through a different delivery device and/or through a different incision and/or natural orifice from that used for inserting the virtual staining device. The virtual staining device can be utilized to diagnose and treat a variety of medical conditions, including but not limited to cancer, hyperplasia, pregnancy (including prenatal diagnosis), infectious disease, autoimmune diseases, or inflammatory diseases.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Although the embodiments of the inventions have been disclosed in the context of a certain preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been illustrated and described in detail, other modifications, which are within the scope of the inventions, will be readily apparent to those of skill in the art based upon this disclosure. It is also contemplated that various combinations or subcombinations of the specific features and aspects of the embodiments may be made and still fall within one or more of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above.

What is claimed is:

1. A system for virtually staining a tissue sample, the system comprising:
    at least one hardware processor; and
    at least one non-transitory memory storing instructions which, when executed by the at least one hardware processor, cause the system to:
        access an electronic medical image of the tissue sample, the electronic medical image of the tissue sample comprising a plurality of pixels generated based on electromagnetic radiation detected by a detector, wherein the plurality of pixels comprises a first pixel and a second pixel;
        determine that a first waveform signature associated with the first pixel of the plurality of pixels is based on a combination of a first plurality of waveform signatures corresponding to multiple substances in the tissue sample at a location associated with the first pixel;
        determine the first plurality of waveform signatures;
        apply transformation data to the first plurality of waveform signatures in order to obtain a first plurality of outputs;
        determine a first single output pixel by volume averaging the first plurality of outputs;
        generate a virtually stained first input image of the tissue sample, wherein the virtually stained first input image comprises at least a first single output pixel;
        determine that a second waveform signature associated with the second pixel of the plurality of pixels is based on a combination of a second plurality of waveform signatures corresponding to multiple substances in the tissue sample at a location associated with the second pixel;
        determine the second plurality of waveform signatures;
        apply transformation data to the second plurality of waveform signatures in order to obtain a second plurality of outputs;
        determine a second single output pixel by volume averaging the second plurality of outputs;
        generate a virtually stained second input image of the tissue sample, wherein the virtually stained second input image comprises at least a second single output pixel;
        generate a combined virtually stained image of the tissue sample comprising the virtually stained first input image and the virtually stained second input image; and
        display the combined virtually stained image of the tissue sample, wherein the combined virtually stained image is substantially identical to an image of the tissue sample when the tissue sample is treated with an actual stain that corresponds to a virtual stain defined by a virtual staining transform.

2. The system for virtually staining a tissue sample of claim 1, wherein the detector is a multi-spectrum detector.

3. The system for virtually staining a tissue sample of claim 1, wherein the tissue sample is in vitro.

4. The system for virtually staining a tissue sample of claim 1, wherein the determining based on the combination of the first plurality of waveform signatures corresponding to multiple substances in the tissue sample at the location associated with the first pixel and the determining based on the combination of the second plurality of waveform signatures corresponding to multiple substances in the tissue sample at the location associated with the second pixel is based at least in part on a first identified vector signature associated with the first pixel of the plurality of pixels and a second identified vector signature associated with the second pixel of the plurality of pixels.

5. The system for virtually staining a tissue sample of claim 1, wherein the tissue sample is a three-dimensional tissue sample.

6. The system for virtually staining a tissue sample of claim 5, wherein the detector is configured to change a focal depth to obtain two-dimensional electromagnetic radiation data at varying z depths of the three-dimensional tissue sample.

7. The system for virtually staining a tissue sample of claim 1, wherein the detector is incorporated into a medical probe.

8. The system for virtually staining a tissue sample of claim 1, wherein the actual stain is a dye configured to color certain portions of the tissue sample.

9. The system for virtually staining a tissue sample of claim 1, wherein the actual stain is a tag.

10. The system for virtually staining a tissue sample of claim 9, wherein the tag is at least one of an antibody, an aptamer, or a fluorescent protein.

11. A method for virtually staining a tissue sample, the method comprising:
    accessing an electronic medical image of the tissue sample, the electronic medical image of the tissue sample comprising a plurality of pixels generated based on electromagnetic radiation detected by a detector, wherein the plurality of pixels comprises a first pixel and a second pixel;

determining that a first waveform signature associated with the first pixel of the plurality of pixels is based on a combination of a first plurality of waveform signatures corresponding to multiple substances in the tissue sample at a location associated with the first pixel;

determining the first plurality of waveform signatures;

applying transformation data to the first plurality of waveform signatures in order to obtain a first plurality of outputs;

determining a first single output pixel by volume averaging the first plurality of outputs;

generating a virtually stained first input image of the tissue sample, wherein the virtually stained first input image comprises at least the first single output pixel;

determining that a second waveform signature associated with the second pixel of the plurality of pixels is based on a combination of a second plurality of waveform signatures corresponding to multiple substances in the tissue sample at a location associated with the second pixel;

determining the second plurality of waveform signatures;

applying transformation data to the second plurality of waveform signatures in order to obtain a second plurality of outputs;

determining a second single output pixel by volume averaging the second plurality of outputs;

generating a virtually stained second input image of the tissue sample, wherein the virtually stained second input image comprises at least the second single output pixel;

generating a combined virtually stained image of the tissue sample comprising the virtually stained first input image and the virtually stained second input image; and displaying the combined virtually stained image of the tissue sample, wherein the combined virtually stained image is substantially identical to an image of the tissue sample when the tissue sample is treated with an actual stain that corresponds to a virtual stain defined by a virtual staining transform.

12. The method of claim 11, wherein the detector is a multi-spectrum detector.

13. The method of claim 11, wherein the tissue sample is in vitro.

14. The method of claim 11, wherein the determining based on the combination of the first plurality of waveform signatures corresponding to multiple substances in the tissue sample at the location associated with the first pixel and the determining based on the combination of the second plurality of waveform signatures corresponding to multiple substances in the tissue sample at the location associated with the second pixel is based at least in part on a first identified vector signature associated the first pixel of the plurality of pixels and a second identified vector signature associated with the second pixel of the plurality of pixels.

15. The method of claim 11, wherein the tissue sample is a three-dimensional tissue sample.

16. The method of claim 15, wherein the detector is configured to change a focal depth to obtain two-dimensional electromagnetic radiation data at varying z depths of the three-dimensional tissue sample.

17. The method of claim 11, wherein the detector is incorporated into a medical probe.

18. The method of claim 11, wherein the actual stain is at least one of a dye configured to color certain portions of the tissue sample.

19. The method of claim 11, wherein the actual stain is a tag.

20. The method of claim 19, wherein the tag is at least one of an antibody, an aptamer, or a fluorescent protein.

* * * * *